(12) United States Patent
Albadawi et al.

(10) Patent No.: US 10,467,510 B2
(45) Date of Patent: Nov. 5, 2019

(54) INTELLIGENT ASSISTANT

(71) Applicant: Microsoft Technology Licensing, LLC, Redmond, WA (US)

(72) Inventors: Haithem Albadawi, Redmond, WA (US); Zongyi Liu, Issaquah, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 10 days.

(21) Appl. No.: 15/636,559

(22) Filed: Jun. 28, 2017

(65) Prior Publication Data

US 2018/0232563 A1    Aug. 16, 2018

Related U.S. Application Data

(60) Provisional application No. 62/459,020, filed on Feb. 14, 2017, provisional application No. 62/482,165, filed on Apr. 5, 2017.

(51) Int. Cl.
*G06K 9/72* (2006.01)
*G06K 9/00* (2006.01)
(Continued)

(52) U.S. Cl.
CPC ............ *G06K 9/726* (2013.01); *A61B 5/0205* (2013.01); *A61B 5/0507* (2013.01); *A61B 5/117* (2013.01);
(Continued)

(58) Field of Classification Search
CPC ..... A61B 5/0205; A61B 5/0507; G01S 11/14; G01S 13/38; G01S 13/726; G01S 13/867;
(Continued)

(56) References Cited

U.S. PATENT DOCUMENTS 6,067,673 A    5/2000  Paese et al.
6,119,088 A    9/2000  Ciluffo
(Continued)

FOREIGN PATENT DOCUMENTS

EP    2947476 A1    11/2015
GB    2522922 A    8/2015
(Continued)

OTHER PUBLICATIONS

Wheeler, et al., "Face Recognition at a Distance", In Publication of Springer, 2011, pp. 353-381.
(Continued)

*Primary Examiner* — Manuchehr Rahmjoo
(74) *Attorney, Agent, or Firm* — Alleman Hall Creasman & Tuttle LLP

(57) ABSTRACT

Examples are disclosed herein that relate to entity tracking. One examples provides a computing device comprising a logic processor and a storage device holding instructions executable by the logic processor to receive image data of an environment including a person, process the image data using a face detection algorithm to produce a first face detection output at a first frequency, determine an identity of the person based on the first face detection output, and process the image data using another algorithm that uses less computational resources of the computing device than the face detection algorithm. The instructions are further executable to track the person within the environment based on the tracking output, and perform one or more of updating the other algorithm using a second face detection output, and updating the face detection algorithm using the tracking output.

20 Claims, 23 Drawing Sheets

(51) Int. Cl.

| | |
|---|---|
| *G06T 7/70* | (2017.01) |
| *G06K 9/62* | (2006.01) |
| *G06F 3/16* | (2006.01) |
| *G10L 15/18* | (2013.01) |
| *G06N 20/00* | (2019.01) |
| *G06T 7/73* | (2017.01) |
| *G06T 7/246* | (2017.01) |
| *G01S 5/18* | (2006.01) |
| *G06T 7/60* | (2017.01) |
| *G10L 15/22* | (2006.01) |
| *G10L 15/28* | (2013.01) |
| *H04R 1/40* | (2006.01) |
| *H04R 3/00* | (2006.01) |
| *H04N 5/33* | (2006.01) |
| *H04N 7/18* | (2006.01) |
| *G10L 15/02* | (2006.01) |
| *G06N 5/02* | (2006.01) |
| *G06N 5/04* | (2006.01) |
| *G10L 15/06* | (2013.01) |
| *G10L 15/24* | (2013.01) |
| *G06F 17/27* | (2006.01) |
| *G10L 15/26* | (2006.01) |
| *G10L 15/19* | (2013.01) |
| *G10L 15/08* | (2006.01) |
| *G10L 15/32* | (2013.01) |
| *G10L 25/51* | (2013.01) |
| *H04L 29/06* | (2006.01) |
| *A61B 5/0205* | (2006.01) |
| *A61B 5/05* | (2006.01) |
| *G01S 13/72* | (2006.01) |
| *G06F 21/35* | (2013.01) |
| *G07C 9/00* | (2006.01) |
| *G08B 13/14* | (2006.01) |
| *G06F 3/01* | (2006.01) |
| *G06F 3/0482* | (2013.01) |
| *G06F 3/0484* | (2013.01) |
| *H04N 21/231* | (2011.01) |
| *G01S 5/28* | (2006.01) |
| *G06F 1/3206* | (2019.01) |
| *G06F 1/3231* | (2019.01) |
| *G06F 1/324* | (2019.01) |
| *G06F 3/03* | (2006.01) |
| *G06F 21/32* | (2013.01) |
| *H04L 12/58* | (2006.01) |
| *G10L 17/04* | (2013.01) |
| *G10L 17/08* | (2013.01) |
| *G06T 7/292* | (2017.01) |
| *H04L 29/08* | (2006.01) |
| *H04N 21/422* | (2011.01) |
| *H04N 21/442* | (2011.01) |
| *H04N 5/232* | (2006.01) |
| *H04W 4/029* | (2018.01) |
| *H04W 4/33* | (2018.01) |
| *A61B 5/00* | (2006.01) |
| *A61B 5/11* | (2006.01) |
| *A61B 5/117* | (2016.01) |
| *G06F 3/0488* | (2013.01) |
| *G06F 16/70* | (2019.01) |
| *H04N 5/247* | (2006.01) |
| *G01S 13/38* | (2006.01) |
| *G01S 13/88* | (2006.01) |
| *G01S 5/16* | (2006.01) |
| *G01S 11/14* | (2006.01) |
| *G10L 17/00* | (2013.01) |
| *G01S 13/86* | (2006.01) |
| *G06N 3/04* | (2006.01) |
| *G08B 29/18* | (2006.01) |

(52) U.S. Cl.
CPC .......... *A61B 5/1113* (2013.01); *A61B 5/7475* (2013.01); *G01S 5/18* (2013.01); *G01S 5/28* (2013.01); *G01S 13/726* (2013.01); *G06F 1/324* (2013.01); *G06F 1/3206* (2013.01); *G06F 1/3231* (2013.01); *G06F 3/011* (2013.01); *G06F 3/017* (2013.01); *G06F 3/0304* (2013.01); *G06F 3/0482* (2013.01); *G06F 3/04842* (2013.01); *G06F 3/167* (2013.01); *G06F 17/271* (2013.01); *G06F 17/279* (2013.01); *G06F 21/32* (2013.01); *G06F 21/35* (2013.01); *G06K 9/00214* (2013.01); *G06K 9/00255* (2013.01); *G06K 9/00261* (2013.01); *G06K 9/00288* (2013.01); *G06K 9/00295* (2013.01); *G06K 9/00342* (2013.01); *G06K 9/00362* (2013.01); *G06K 9/00711* (2013.01); *G06K 9/00973* (2013.01); *G06K 9/6254* (2013.01); *G06K 9/6255* (2013.01); *G06K 9/6289* (2013.01); *G06K 9/6296* (2013.01); *G06N 5/025* (2013.01); *G06N 5/047* (2013.01); *G06N 20/00* (2019.01); *G06T 7/248* (2017.01); *G06T 7/292* (2017.01); *G06T 7/60* (2013.01); *G06T 7/70* (2017.01); *G06T 7/74* (2017.01); *G07C 9/00111* (2013.01); *G08B 13/1427* (2013.01); *G10L 15/02* (2013.01); *G10L 15/063* (2013.01); *G10L 15/08* (2013.01); *G10L 15/18* (2013.01); *G10L 15/1815* (2013.01); *G10L 15/1822* (2013.01); *G10L 15/19* (2013.01); *G10L 15/22* (2013.01); *G10L 15/24* (2013.01); *G10L 15/26* (2013.01); *G10L 15/28* (2013.01); *G10L 15/32* (2013.01); *G10L 17/04* (2013.01); *G10L 17/08* (2013.01); *G10L 25/51* (2013.01); *H04L 51/02* (2013.01); *H04L 63/102* (2013.01); *H04L 67/12* (2013.01); *H04L 67/22* (2013.01); *H04N 5/23219* (2013.01); *H04N 5/332* (2013.01); *H04N 7/181* (2013.01); *H04N 7/188* (2013.01); *H04N 21/231* (2013.01); *H04N 21/42203* (2013.01); *H04N 21/44218* (2013.01); *H04N 21/44222* (2013.01); *H04R 1/406* (2013.01); *H04R 3/005* (2013.01); *H04W 4/029* (2018.02); *H04W 4/33* (2018.02); *A61B 5/05* (2013.01); *A61B 5/1118* (2013.01); *G01S 5/16* (2013.01); *G01S 11/14* (2013.01); *G01S 13/38* (2013.01); *G01S 13/867* (2013.01); *G01S 13/888* (2013.01); *G06F 3/0488* (2013.01); *G06F 16/70* (2019.01); *G06F 2203/0381* (2013.01); *G06F 2221/2111* (2013.01); *G06K 2209/09* (2013.01); *G06N 3/0445* (2013.01); *G06T 2207/10016* (2013.01); *G06T 2207/10024* (2013.01); *G06T 2207/20101* (2013.01); *G06T 2207/30196* (2013.01); *G06T 2207/30201* (2013.01); *G06T 2207/30204* (2013.01); *G06T 2207/30232* (2013.01); *G07C 9/00134* (2013.01); *G08B 29/186* (2013.01); *G10L 17/00* (2013.01); *G10L 2015/0635* (2013.01); *G10L 2015/088* (2013.01); *G10L 2015/223* (2013.01); *G10L 2015/225* (2013.01); *G10L 2015/228* (2013.01); *H04N 5/247* (2013.01); *Y02D 10/126* (2018.01); *Y02D 10/173* (2018.01)

(58) Field of Classification Search
CPC . G01S 13/888; G01S 5/16; G01S 5/18; G01S 5/28; G06F 17/271; G06F 17/279; G06F 17/30781; G06F 1/3206; G06F 1/3231; G06F 1/324; G06F 21/32; G06F 21/35; G06F 2203/0381; G06F 3/011; G06F 3/017; G06F 3/0304; G06F 3/0482; G06F 3/04842; G06F 3/0488; G06F 3/167; G06K 2209/09; G06K 9/00214; G06K 9/00255; G06K 9/00261; G06K 9/00288; G06K 9/00295; G06K 9/00342; G06K 9/00711; G06K 9/00973; G06K 9/6254; G06K 9/6255; G06K 9/6289; G06K 9/6296; G06K 9/726; G06N 3/0445; G06N 5/025; G06N 5/047; G06N 99/005; G06T 2207/10016; G06T 2207/10024; G06T 2207/20101; G06T 2207/30196; G06T 2207/30201; G06T 2207/30204; G06T 2207/30232; G06T 7/248; G06T 7/292; G06T 7/60; G06T 7/70; G06T 7/74; G07C 9/00111; G07C 9/00134; G08B 13/1427; G10L 15/02; G10L 15/063; G10L 15/08; G10L 15/18; G10L 15/1815; G10L 15/1822; G10L 15/19; G10L 15/22; G10L 15/24; G10L 15/26; G10L 15/28; G10L 15/32; G10L 17/00; G10L 17/04; G10L 17/08; G10L 2015/0635; G10L 2015/088; G10L 2015/223; G10L 2015/225; G10L 2015/228; G10L 25/51; H04L 51/02; H04L 63/102; H04N 21/231; H04N 5/247; H04N 5/332; H04N 7/181; H04N 7/188; H04R 1/406; H04R 3/005; Y02D 10/126; Y02D 10/173; Y04S 10/54

See application file for complete search history.

(56) References Cited

U.S. PATENT DOCUMENTS

| | | |
|---|---|---|
| 6,332,122 B1 | 12/2001 | Ortega et al. |
| 6,442,524 B1 | 8/2002 | Ecker et al. |
| 6,477,500 B2 | 11/2002 | Maes |
| 6,496,799 B1 | 12/2002 | Pickering |
| 6,574,601 B1 | 6/2003 | Brown et al. |
| 6,728,679 B1 | 4/2004 | Strubbe et al. |
| 6,816,730 B2 | 11/2004 | Davies et al. |
| 6,873,953 B1 | 3/2005 | Lennig |
| 7,019,749 B2 | 3/2006 | Guo et al. |
| 7,050,110 B1 | 5/2006 | Lienhart et al. |
| 7,330,566 B2 | 2/2008 | Cutler |
| 7,475,010 B2 | 1/2009 | Chao |
| 7,610,365 B1 | 10/2009 | Kraft et al. |
| 7,716,056 B2 | 5/2010 | Weng et al. |
| 7,803,050 B2 | 9/2010 | Mao et al. |
| 8,139,945 B1 | 3/2012 | Amir et al. |
| 8,165,087 B2 | 4/2012 | Panabaker |
| 8,170,875 B2 | 5/2012 | Hetherington et al. |
| 8,213,689 B2 | 7/2012 | Yagnik et al. |
| 8,265,252 B2 | 9/2012 | Ducheneaut et al. |
| 8,326,627 B2 | 12/2012 | Kennewick et al. |
| 8,340,975 B1 | 12/2012 | Rosenberger |
| 8,374,879 B2 | 2/2013 | Falcon et al. |
| 8,453,402 B2 | 6/2013 | Huang |
| 8,457,959 B2 | 6/2013 | Kaiser |
| 8,543,402 B1 | 9/2013 | Ma |
| 8,639,762 B2 | 1/2014 | Rasmussen et al. |
| 8,644,842 B2 | 2/2014 | Arrasvuori et al. |
| 8,712,758 B2 | 4/2014 | Crouch et al. |
| 8,752,145 B1 | 6/2014 | Dotan et al. |
| 8,762,150 B2 | 6/2014 | Edgington et al. |
| 8,762,156 B2 | 6/2014 | Chen |
| 8,779,965 B2 | 7/2014 | Sentelle et al. |
| 8,805,691 B2 | 8/2014 | Genly |
| 8,861,924 B2 | 10/2014 | Meads et al. |
| 8,862,156 B2 | 10/2014 | Bell et al. |
| 8,903,128 B2 | 12/2014 | Shet et al. |
| 8,913,103 B1 | 12/2014 | Sargin et al. |
| 8,942,986 B2 | 1/2015 | Cheyer et al. |
| 8,949,359 B2 | 2/2015 | Rasmussen et al. |
| 9,037,601 B2 | 5/2015 | Palay |
| 9,085,303 B2 | 7/2015 | Wolverton et al. |
| 9,119,512 B2 | 9/2015 | Martins, Jr. et al. |
| 9,171,542 B2 | 10/2015 | Gandrabur et al. |
| 9,230,544 B2 | 1/2016 | Kwon et al. |
| 9,268,406 B2 | 2/2016 | Geisner et al. |
| 9,300,925 B1 | 3/2016 | Zhang |
| 9,307,355 B2 | 4/2016 | Nehrenz et al. |
| 9,311,932 B2 | 4/2016 | Carter |
| 9,318,105 B1 | 4/2016 | Khosla |
| 9,348,990 B2 | 5/2016 | Chuaprasert et al. |
| 9,368,114 B2 | 6/2016 | Larson et al. |
| 9,378,740 B1 | 6/2016 | Rosen et al. |
| 9,380,177 B1 | 6/2016 | Rao et al. |
| 9,389,681 B2 | 7/2016 | Sankar et al. |
| 9,412,392 B2 | 8/2016 | Lindahl |
| 9,424,840 B1 | 8/2016 | Hart et al. |
| 9,495,331 B2 | 11/2016 | Govrin et al. |
| 9,495,613 B2 | 11/2016 | Holz et al. |
| 9,507,977 B1 | 11/2016 | Mor et al. |
| 9,508,341 B1 | 11/2016 | Parlikar et al. |
| 9,514,227 B1 | 12/2016 | Garrett et al. |
| 9,558,749 B1 | 1/2017 | Secker-Walker et al. |
| 9,576,574 B2 | 2/2017 | van Os |
| 9,622,059 B2 | 4/2017 | Bouzid et al. |
| 9,626,352 B2 | 4/2017 | Allen et al. |
| 9,633,652 B2 | 4/2017 | Kumiawati et al. |
| 9,749,583 B1 | 8/2017 | Fineberg et al. |
| 9,761,055 B2 | 9/2017 | Miller |
| 9,767,616 B2 | 9/2017 | Miller |
| 9,842,299 B2 | 12/2017 | Stolarz et al. |
| 9,898,250 B1 | 2/2018 | Williams et al. |
| 9,965,247 B2 | 5/2018 | Jarvis et al. |
| 10,178,301 B1 | 1/2019 | Welbourne et al. |
| 2003/0103647 A1 | 6/2003 | Rui et al. |
| 2003/0131064 A1 | 7/2003 | Bell et al. |
| 2005/0182627 A1 | 8/2005 | Tanaka et al. |
| 2005/0216264 A1 | 9/2005 | Attwater et al. |
| 2005/0225427 A1 | 10/2005 | Bell et al. |
| 2005/0285774 A1 | 12/2005 | Wittenberg et al. |
| 2006/0028552 A1 | 2/2006 | Aggarwal et al. |
| 2007/0024487 A1 | 2/2007 | Zemany et al. |
| 2007/0100480 A1 | 5/2007 | Sinclair et al. |
| 2007/0152157 A1 | 7/2007 | Page |
| 2007/0198245 A1 | 8/2007 | Kamatani et al. |
| 2007/0271086 A1 | 11/2007 | Peters et al. |
| 2008/0030345 A1 | 2/2008 | Austin et al. |
| 2008/0071547 A1 | 3/2008 | Prieto et al. |
| 2008/0077015 A1 | 3/2008 | Boric-Lubecke et al. |
| 2008/0195387 A1 | 8/2008 | Zigel et al. |
| 2008/0288251 A1 | 11/2008 | Cooper et al. |
| 2009/0066690 A1 | 3/2009 | Harrison |
| 2009/0303342 A1* | 12/2009 | Corcoran ........... G06K 9/00228 348/222.1 |
| 2009/0319269 A1 | 12/2009 | Aronowitz |
| 2010/0100851 A1 | 4/2010 | Clark et al. |
| 2010/0179813 A1 | 7/2010 | Summerfield et al. |
| 2010/0195906 A1 | 8/2010 | Uliyar et al. |
| 2011/0010170 A1 | 1/2011 | Burns et al. |
| 2011/0184735 A1 | 7/2011 | Flaks et al. |
| 2011/0298967 A1 | 12/2011 | Clavin et al. |
| 2012/0026335 A1 | 2/2012 | Brown et al. |
| 2012/0265535 A1 | 10/2012 | Bryant-rich et al. |
| 2012/0268604 A1 | 10/2012 | Tree |
| 2013/0110519 A1 | 5/2013 | Cheyer et al. |
| 2013/0117377 A1 | 5/2013 | Miller |
| 2013/0212501 A1 | 8/2013 | Anderson et al. |
| 2013/0253936 A1 | 9/2013 | Harvey |
| 2013/0342568 A1 | 12/2013 | Ambrus et al. |
| 2014/0033071 A1 | 1/2014 | Gruber et al. |

(56) References Cited

U.S. PATENT DOCUMENTS

| | | |
|---|---|---|
| 2014/0067679 A1 | 3/2014 | O'reilly et al. |
| 2014/0180629 A1 | 6/2014 | Dokmanic et al. |
| 2014/0214421 A1 | 7/2014 | Shriberg et al. |
| 2014/0214429 A1 | 7/2014 | Pantel |
| 2014/0222422 A1 | 8/2014 | Sarikaya et al. |
| 2014/0244263 A1 | 8/2014 | Pontual et al. |
| 2014/0330569 A1 | 11/2014 | Kolavennu et al. |
| 2014/0341440 A1 | 11/2014 | Walch |
| 2015/0016642 A1 | 1/2015 | Walsh et al. |
| 2015/0019714 A1 | 1/2015 | Shaashua et al. |
| 2015/0025887 A1 | 1/2015 | Sidi et al. |
| 2015/0032456 A1 | 1/2015 | Wait |
| 2015/0102996 A1 | 4/2015 | Yim et al. |
| 2015/0138332 A1 | 5/2015 | Cheng et al. |
| 2015/0149179 A1 | 5/2015 | Korbecki |
| 2015/0149182 A1 | 5/2015 | Kalns et al. |
| 2015/0162000 A1 | 6/2015 | Di censo et al. |
| 2015/0172285 A1 | 6/2015 | Lo et al. |
| 2015/0249664 A1 | 9/2015 | Talhami et al. |
| 2015/0279368 A1 | 10/2015 | Contolini et al. |
| 2015/0340033 A1 | 11/2015 | Di fabbrizio et al. |
| 2015/0347114 A1 | 12/2015 | Yoon |
| 2015/0382047 A1 | 12/2015 | Van os et al. |
| 2016/0019889 A1 | 1/2016 | Alvarez guevara et al. |
| 2016/0086018 A1 | 3/2016 | Lemoff |
| 2016/0088043 A1 | 3/2016 | Jiang et al. |
| 2016/0092732 A1 | 3/2016 | Black |
| 2016/0138247 A1 | 5/2016 | Conway et al. |
| 2016/0148417 A1 | 5/2016 | Kim et al. |
| 2016/0155443 A1 | 6/2016 | Khan et al. |
| 2016/0173293 A1 | 6/2016 | Kennedy |
| 2016/0179831 A1 | 6/2016 | Gruber et al. |
| 2016/0187961 A1 | 6/2016 | Elibol et al. |
| 2016/0203002 A1 | 7/2016 | Kannan et al. |
| 2016/0210411 A1 | 7/2016 | Mentis |
| 2016/0217783 A1 | 7/2016 | Konuma et al. |
| 2016/0225373 A1 | 8/2016 | Casado et al. |
| 2016/0234595 A1 | 8/2016 | Goran et al. |
| 2016/0234616 A1 | 8/2016 | Gateau |
| 2016/0283185 A1 | 9/2016 | Mclaren et al. |
| 2016/0342702 A1 | 11/2016 | Barve et al. |
| 2016/0358598 A1 | 12/2016 | Williams et al. |
| 2016/0360336 A1 | 12/2016 | Gross et al. |
| 2016/0380929 A1 | 12/2016 | Katis et al. |
| 2017/0013409 A1 | 1/2017 | Cerchio et al. |
| 2017/0025124 A1* | 1/2017 | Mixter ............... G10L 15/32 |
| 2017/0032021 A1 | 2/2017 | Watanachote |
| 2017/0032787 A1 | 2/2017 | Dayal |
| 2017/0039423 A1 | 2/2017 | Cork et al. |
| 2017/0039602 A1 | 2/2017 | Shi-nash et al. |
| 2017/0068423 A1 | 3/2017 | Napolitano et al. |
| 2017/0078573 A1 | 3/2017 | Chen et al. |
| 2017/0133011 A1 | 5/2017 | Chen et al. |
| 2017/0140760 A1 | 5/2017 | Sachdev |
| 2017/0185375 A1 | 6/2017 | Martel et al. |
| 2017/0194000 A1 | 7/2017 | Itani et al. |
| 2017/0230705 A1 | 8/2017 | Pardue et al. |
| 2017/0236512 A1 | 8/2017 | Williams et al. |
| 2017/0242651 A1 | 8/2017 | Lang et al. |
| 2017/0249309 A1 | 8/2017 | Sarikaya |
| 2017/0262472 A1 | 9/2017 | Goldenberg |
| 2017/0278480 A1 | 9/2017 | Sung et al. |
| 2017/0287490 A1 | 10/2017 | Biswal et al. |
| 2017/0315208 A1 | 11/2017 | Sadr |
| 2017/0359666 A1 | 12/2017 | Lyren et al. |
| 2018/0047394 A1 | 2/2018 | Tian et al. |
| 2018/0048768 A1 | 2/2018 | Spittle et al. |
| 2018/0074785 A1 | 3/2018 | Ohmura |
| 2018/0091782 A1 | 3/2018 | Bashkin |
| 2018/0096696 A1 | 4/2018 | Mixter |
| 2018/0158454 A1 | 6/2018 | Campbell et al. |
| 2018/0199123 A1 | 7/2018 | Rao et al. |
| 2018/0218080 A1 | 8/2018 | Krishnamurthy et al. |
| 2018/0231653 A1 | 8/2018 | Pradeep et al. |
| 2018/0232201 A1 | 8/2018 | Holtmann |
| 2018/0232571 A1 | 8/2018 | Bathiche et al. |
| 2018/0232608 A1 | 8/2018 | Pradeep et al. |
| 2018/0232645 A1 | 8/2018 | Finkelstein et al. |
| 2018/0232662 A1 | 8/2018 | Solomon et al. |
| 2018/0232902 A1 | 8/2018 | Albadawi et al. |
| 2018/0233132 A1 | 8/2018 | Herold et al. |
| 2018/0233139 A1 | 8/2018 | Finkelstein et al. |
| 2018/0233140 A1 | 8/2018 | Koishida et al. |
| 2018/0233141 A1 | 8/2018 | Solomon et al. |
| 2018/0233142 A1 | 8/2018 | Koishida et al. |
| 2018/0233145 A1 | 8/2018 | Bathiche et al. |
| 2018/0260680 A1 | 9/2018 | Finkelstein et al. |
| 2018/0293221 A1 | 10/2018 | Finkelstein et al. |
| 2019/0057703 A1 | 2/2019 | Zeinstra |

FOREIGN PATENT DOCUMENTS

| | | |
|---|---|---|
| KR | 1020070016280 A | 2/2007 |
| WO | 2007018523 A2 | 2/2007 |
| WO | 2010104772 A1 | 9/2010 |
| WO | 2013061268 A2 | 5/2013 |
| WO | 2015012449 A1 | 1/2015 |
| WO | 2016114922 A1 | 7/2016 |
| WO | 2016162678 A1 | 10/2016 |
| WO | 2016205419 A1 | 12/2016 |

OTHER PUBLICATIONS

"Train the Natural Language Processing Classifiers", Retrieved From <<https://www.mindmeld.com/docs/train_the_natural_language_processing_classifiers.html>>, Retrieved on: May 2, 2017, 10 Pages.

"Using Multiple Alexa Devices", Retrieved From <<https://www.amazon.com/gp/help/customer/display.html?nodeId=202013740>>, Apr. 24, 2017, 2 Pages.

"Application Filed in U.S. Appl. No. 15/173,349", filed Jun. 3, 2016, 34 Pages.

"Application Filed in U.S. Appl. No. 15/395,961", filed Dec. 30, 2016, 79 Pages.

Ballan, et al., "Event Detection and Recognition for Semantic Annotation of Video", In Journal of Multimedia Tools and Applications, vol. 51, Issue 1, Nov. 10, 2010, pp. 279-302.

Beltagy, et al., "Improved Semantic Parsers for If-Then Statements", In Proceedings of the 54th Annual Meeting of the Association for Computational Linguistics, vol. 1, Aug. 7, 2016, pp. 726-736.

Cho, et al., "A Multi-Sensor Fusion System for Moving Object Detection and Tracking in Urban Driving Environments", In IEEE International Conference on Robotics & Automation, May 31, 2014, 8 Pages.

Fossard, et al., "Between Anaphora and Deixis . . . The Resolution of the Demonstrative Noun Phrase that N", In Journal of Language and Cognitive Processes, vol. 27, Issue 9, Nov. 2, 2011, 3 Pages.

Gebhart, Andrew, "How to bring Alexa into every room of your home", Retrieved From <<https://www.cnet.com/how-to/how-to-install-alexa-in-every-room-of-your-home/>>, Feb. 2, 2017, 8 Pages.

Goncalves, et al., "Assessing Users' Emotion At Interaction Time: A Multimodal Approach With Multiple Sensors", In Proceedings of Soft Computing, vol. 21, Issue 18, Mar. 21, 2016, 8 Pages.

Goswami, et al., "A Reviewon Low Light Image Enhancement Using Image Processing Technique", In International Journal of Technical Research, vol. 5, Issue 1, Mar. 2016, pp. 60-62.

He, et al., "Sensor scheduling for target tracking: A Monte Carlo sampling approach", In Journal of Digital Signal Processing, vol. 16, Issue 5, Sep. 2006, pp. 533-545.

Kabadjov, Mijail Alexandrov., "A Comprehensive Evaluation of Anaphora Resolution and Discourse—new Classification", In thesis of University of Essex, May 2007, 266 Pages.

Kang, et al., "Detection and Tracking of Moving Objects from Overlapping EO and IR Sensors", In Conference on Computer Vision and Pattern Recognition Workshop, Jun. 27, 2004, 6 Pages.

Liu, et al. "Reliable Multiple Object Tracking under Heavy Occlusions", In Intelligence Information Processing and Trusted Computing (IPTC), 2010 International Symposium., Oct. 28, 2010, 3 Pages.

(56) References Cited

OTHER PUBLICATIONS

Mk, et al., "Ambiguities in Natural Language Processing", In International Journal of Innovative Research in Computer and Communication Engineering, vol. 2, Special Issue 5, Oct. 2014, pp. 392-394.

Pan, et al., "Robust Occlusion Handling in Object Tracking", In IEEE Conference on Computer Vision and Pattern Recognition, Jun. 17, 2007, 8 Pages.

Quirk, et al., "Language to Code: Learning Semantic Parsers for If-This-Then-That Recipes", In Proceedings of the 53rd Annual Meeting of the Association for Computational Linguistics, Jul. 26, 2015, pp. 878-888.

Rizwan, et al., "Local Enhancement for Robust Face Detection in Poor SNR Images", In International Journal of Computer Science and Network Security, vol. 9, Issue 6, Jun. 2009, pp. 93-96.

Sinha, et al., "An Analysis Engine for Dependable Elicitation on Natural Language Use Case Description and its Application to Industrial Use Cases", In IBM Research Report, RC242712, Dec. 18, 2008, 12 Pages.

Toutanova, et al., "Compositional Learning of Embeddings for Relation Paths in Knowledge Bases and Text", In Proceedings of the 54th Annual Meeting of the Association for Computational Linguistics, Aug. 7, 2016, pp. 1434-1444.

Wagner, Martin, "Tracking with Multiple Sensors", by Faculty of Computer Science at the Technical University of Munich, Sep. 12, 2004, 202 Pages.

Boakye, et al., "Overlapped Speech Detection for Improved Speaker Diarization in Multiparty Meetings", In Proceedings of IEEE International Conference on Acoustics, Speech and Signal Processing, Mar. 31, 2008, 4 Pages.

Huijbregts, et al., "Speech Overlap Detection in a Two-Pass Speaker Diarization System", In Proceedings of 10th Annual Conference of the International Speech Communication, Sep. 6, 2009, pp. 1063-1066.

Zotkin, et al., "Joint Audio-Visual Tracking Using Particle Filters", In EURASIP Journal on Applied Signal Processing, vol. 2002, Issue 1, Jan. 2002, pp. 1154-1164.

"Amazon Alexa's 'Follow-Up Mode' enables successive requests without trigger word", Retrieved from: https://appleinsider.com/articles/18/03/09/amazon-alexas-follow-up-mode-enables-successive-requests-without-trigger-word, Mar. 9, 2018, 7 Pages.

"Multiple Agents (each trained for different domain) for One Chat Bot?", Retrieved from: https://discuss.api.ai/t/multiple-agents-each-trained-for-different-domain-for-one-chat-bot/1002, Jul. 1, 2016, 1 Page.

"SARA: The Socially Aware Robot Assistant", Retrieved from: https://web.archive.org/web/20160707141922/http:/articulab.hcii.cs.cmu.edu:80/projects/sara/, Jul. 7, 2017, 10 Pages.

Arsikere, et al., "Computationally-efficient Endpointing Features for Natural Spoken Interaction with Personal-assistant Systems", In Proceedings of IEEE International Conference on Acoustics, Speech and Signal Processing, May 4, 2014, pp. 3241-3245.

Ferrer, et al., "Is the Speaker Done Yet? Faster and More Accurate End-of-Utterance Detection using Prosody", In the proceedings of Seventh International Conference on Spoken Language Processing, Sep. 16, 2002, pp. 2061-2064.

Kalal, et al., "Face-TLD: Tracking-Learning-Detection Applied to Caces", In Proceedings of 17th IEEE International Conference on Image Processing, Sep. 26, 2010, pp. 3789-3792.

Kozhaya, Joe, "10 Steps to Train an Effective Chatbot and its Machine Learning Models", Retrieved from: https://developer.ibm.com/dwblog/2016/10-steps-train-chat-bot-chatbot-machine-learning/, Dec. 12, 2016, 7 Pages.

Lacharite, Noelle, "Updated: Alexa Skills Kit Fact Template: Step-by-Step Guide to Build a Fact Skill", Retrieved from: https://developer.amazon.com/blogs/post/Tx3DVGG0K0TPUGQ/New-Alexa-Skills-Kit-Template:-Step-by-Step-Guide-to-Build-a-Fact-Skill, Mar. 29, 2016, 33 Pages.

Li, Bo, "A Multiple-Camera System Calibration Toolbox Using a Feature Descriptor-based Calibration Pattern", In Proceedings of IEEE International Conference on Intelligent Robots and Systems, Nov. 3, 2013, pp. 1301-1307.

Mengusoglu, Erhan, "Confidence Measures for Speech/Speaker Recognition and Applications on Turkish LVCSR", Retrieved from https://web.archive.org/web/20040619044603/http://www.tcts.fpms.ac.be/publications/phds/mengusoglu/thesis_mengus.pdf, Apr. 20, 2004, 143 Pages.

Mikolajczyk, K, et al., "Face Detection and Tracking in a Video by Propagating Detection Probabilities", In Proceedings of IEEE Transactions on Pattern Analysis and Machine Intelligence, vol. 25, Issue 10, Oct. 1, 2003, pp. 1215-1228.

Panzarino, Matthew, "Here's an Actual 3D Indoor Map of a Room Captured With Google's Project Tango Phone", Retrieved From: https://techcrunch.com/2014/02/21/heres-an-actual-3d-indoor-map-of-a-room-captured-with-googles-project-tango-phone/, Feb. 21, 2014, 6 Pages.

"International Search Report and Written Opinion Issued in PCT Application No. PCT/US2018/017139", dated May 8, 2018, 13 Pages.

"International Search Report and Written Opinion Issued in PCT Application No. PCT/US2018/017140", dated May 18, 2018, 12 Pages.

"International Search Report and Written Opinion Issued in PCT Application No. PCT/US2018/017506", dated May 4, 2018, 13 Pages.

"International Search Report and Written Opinion Issued in PCT Application No. PCT/US2018/017508", dated May 8, 2018, 13 Pages.

"International Search Report and Written Opinion Issued in PCT Application No. PCT/US2018/017509", dated May 11, 2018, 11 Pages.

"International Search Report and Written Opinion Issued in PCT Application No. PCT/US2018/017510", dated Apr. 20, 2018, 14 Pages.

"International Search Report and Written Opinion Issued in PCT Application No. PCT/US2018/017511", dated May 17, 2018, 12 Pages.

"International Search Report and Written Opinion Issued in PCT Application No. PCT/US2018/017512", dated May 4, 2018, 15 Pages.

"International Search Report and Written Opinion Issued in PCT Application No. PCT/US2018/017513", dated Apr. 12, 2018, 15 Pages.

"International Search Report and Written Opinion Issued in PCT Application No. PCT/US2018/017514", dated May 17, 2018, 12 Pages.

"International Search Report and Written Opinion Issued in PCT Application No. PCT/US2018/017515", dated May 9, 2018, 12 Pages.

"International Search Report and Written Opinion Issued in PCT Application No. PCT/US2018/017517", dated May 11, 2018, 12 Pages.

Porcheron, et al., "Do Animals Have Accents?": Talking with Agents in Multi-Party Conversation, In Proceedings of 20th ACM Conference on Computer-Supported cooperative Work and Social Computing, Feb. 25, 2017, 14 Pages.

Pullen, John Patrick., "Amazon Echo Tip: How to Add Multiple Users ! Time", Retrieved from http://time.com/4668359/amazon-echo-alexa-multiple-accounts/, Feb. 13, 2017., 3 Pages.

Xiang, Li, "Improving Knowledge Base Population With Information Extraction", A Thesis Submitted in Partial fulfillment of the Requirements of the University of New York for the Degree of Doctor of Philosophy, May 2016, 131 Pages.

Yamamoto, S, et al., "Algorithm Optimizations for Low-Complexity Eye Tracking", In Proceedings of IEEE International Conference on Systems, Man, and Cybernetics, Oct. 2009, pp. 18-22.

Yun-Nung, Chen, "Unsupervised Learning and Modeling of Knowledge and Intent for Spoken Dialogue Systems", In Proceedings of the 53rd Annual Meeting of the Association for Computational Linguistics, Jul. 28, 2015, 8 Pages.

(56) References Cited

OTHER PUBLICATIONS

Zhang, et al., "A Joint Model of Intent Determination and Slot Filling for Spoken Language Understanding", In Proceedings of the Twenty-Fifth International Joint Conference on Artificial Intelligence, Jul. 9, 2016, pp. 2993-2999.
"Non Final Office Action Issued in U.S. Appl. No. 15/636,422", dated Sep. 4, 2018, 11 Pages.
"Non Final Office Action Issued in U.S. Appl. No. 15/640,251", dated Oct. 15, 2018, 22 Pages.
"Non Final Office Action Issued in U.S. Appl. No. 15/646,871", dated Dec. 19, 2018, 22 Pages.
"Non Final Office Action Issued in U.S. Appl. No. 15/656,994", dated Jan. 22, 2019, 8 Pages.
"Non Final Office Action Issued in U.S. Appl. No. 15/657,031", dated Oct. 5, 2018, 16 Pages.
"Non-Final Office Action Issued in U.S. Appl. No. 15/657,822", dated Feb. 21, 2019, 25 Pages.
"Non Final Office Action Issued in U.S. Appl. No. 15/832,656", dated Feb. 7, 2019, 8 Pages.
"Non Provisional Application Filed in U.S. Appl. No. 15/885,518", filed Jan. 31, 2018, 40 Pages.
"Final Office Action Issued in U.S. Appl. No. 15/640,251", dated Apr. 2, 2019, 22 Pages.
Yu, et al., "Smart Meeting Systems: A Survey of State of the Art and Open Issues", In the Proceedings of ACM Computing Surveys, vol. 42, No. 2, Mar. 5, 2010, 20 Pages.
"International Search Report & Written Opinion for PCT Patent Application No. PCT/US2018/062384", dated Feb. 15, 2019, 12 Pages.
Moattar, et al., "A Review on Speaker Diarization Systems and Approaches", In the Publication of Speech communication, vol. 54, Issue 10, Dec. 12, 2010, 39 Pages.
Miro, et al., "Speaker Diarization: A review of Recent Research", In the Proceedings of IEEE Transactions on Audio, Speech and Language Processing, vol. 20, Issue 2, Feb. 1, 2012, 15 Pages.
"Final Office Action Issued in U.S. Appl. No. 15/646,871", dated Apr. 19, 2019, 22 Pages.
"Non Final Office Action Issued in U.S. Appl. No. 15/682,425", dated May 6, 2019, 12 Pages.
"Non Final Office Action Issued in U.S. Appl. No. 15/682,407", dated Jun. 26, 2019, 15 Pages.
"International Search Report and Written Opinion Issued in PCT Application No. PCT/US2019/022836", dated Jun. 24, 2018, 15 Pages.
Constine, "Instagram launches selfie filters, copying the last big snapchat feature", Retrieved from https://techcrunch.com/May 16, 2019/instagram-face-filters/, May 16, 2017, 10 Pages.
"International Search Report and Written Opinion Issued in PCT Application No. PCT/US2019/029558", dated Jun. 28, 2019, 10 Pages.

\* cited by examiner

INTELLIGENT ASSISTANT

CROSS REFERENCE TO RELATED APPLICATIONS

This application claims priority to U.S. Provisional Patent Application No. 62/459,020 filed Feb. 14, 2017, and to U.S. Provisional Patent Application No. 62/482,165 filed Apr. 5, 2017, the entirety of which are hereby incorporated herein by reference.

BACKGROUND

Interacting with computing systems via natural interactions, such as one or more of voice recognition, text, gesture recognition, motion detection, gaze detection, intent recognition, brain activity assessment, text, the state of a home automated device, etc., enables natural user interface experiences. As the volume of digital information and the number of computing devices increases, managing such natural user interaction interfaces to provide positive user experiences can prove challenging.

SUMMARY

Figure 1:
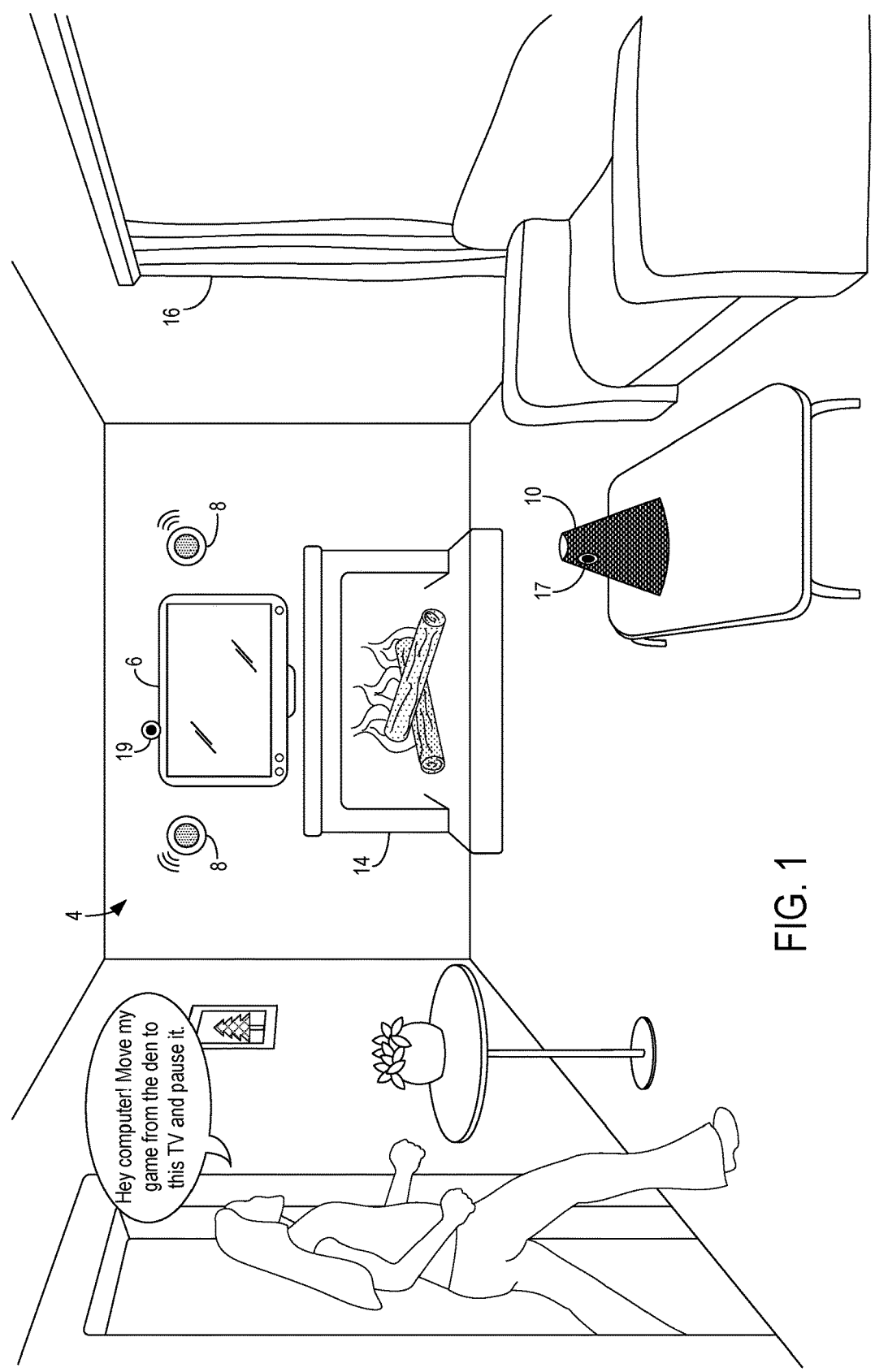
FIG. 1 shows an example environment with an intelligent assistant system in the form of an all-in-one computing device according to an example of the present disclosure.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

Computing devices and methods are disclosed that relate to entity tracking. In one example, a computing device comprises a logic processor and a storage device holding instructions executable by the logic processor to receive image data of an environment including a person, process the image data using a face detection algorithm to produce a first face detection output at a first frequency, determine an identity of the person based on the first face detection output, and process the image data using another algorithm that uses less computational resources of the computing device than the face detection algorithm. The instructions are further executable to track the person within the environment based on the tracking output, and perform one or more of updating the other algorithm using a second face detection output, and updating the face detection algorithm using the tracking output.

DETAILED DESCRIPTION

Overview

The present disclosure relates generally to systems, methods and logical constructs for providing intelligent assistance to users. In some examples, a variety of sensor data may be utilized to intelligently determine the content and/or timing of messages communicated to users and/or the performance of actions. In some examples natural language inputs, such as user commands and other utterances, may be received and processed. In some examples, a natural language input may be parsed and analyzed to generate an indication of one or more user intentions associated with the input. In some examples, data from one or more sensors also may be utilized to process the natural language inputs and/or user intentions. Such data may be processed to generate identity, location/position, status/activity, and/or other information related to one or more entities within range of a sensor. Statistical probabilities based on current and past data may be utilized to generate confidence values associated with entity information.

User intentions may be processed to at least partially resolve linguistic, semantic and/or other ambiguities. Using the resulting clarified intention, a commitment for carrying out the intention may be generated and either executed or stored. In determining whether and when to execute a commitment, one or more factors may be examined. In some examples, factors related to the importance of the commitment to a particular user, the receptivity of the user to receiving input, and/or the user's current context may be estimated. Machine learning techniques may be applied to such factors and other data to learn and make predictions from such information.

Following are descriptions of example implementations and use cases of an intelligent assistant system for processing natural language inputs. Additional details of various aspects of the system are provided below.

Example Environment

FIG. 1 shows an example of a living room 4 with one example of an intelligent assistant system in the form of an all-in-one computing device 10. As described in more detail below, in some examples computing device 10 may be configured to receive and process natural language inputs. A user may utilize the intelligent assistant system for myriad functions. For example, the user may provide natural language input to ask the intelligent assistant system to perform a variety of tasks, such as transferring an instance of a computer game from one device to another. In another example, such a transfer may be performed programmatically without input from the user. For example, computing device 10 may utilize sensor data, such as audio and/or video data, to detect when the user moves to another room and is looking at or "engaged" with another device. Using this data, computing device 10 may automatically transfer the instance of the computer game to the other device.

The user may ask the system for information about a wide range of topics, such as the weather, personal calendar events, movie show times, etc. In some examples, the intelligent assistant system also may be configured to control elements in the living room 4, such as a television 6, speakers 8 of a music system, a gas fireplace 14, or motorized curtains 16.

The intelligent assistant system also may be utilized to receive and store messages and/or reminders to be delivered at an appropriate future time. Using data received from sensors, the intelligent assistant system may track and/or communicate with one or more users or other entities.

In some examples, the intelligent system may utilize image data received from one or more image sensors integrated in computing device 10 in performing user-related tasks. To this end, FIG. 1 shows an image sensor 17 integrated in computing device 10 that is configured to capture image data of the surrounding environment including the user. However, two or any other suitable number of image sensors may be integrated in the computing device. One or more other image sensors remotely located from computing device 10 may be used in addition to or instead of image sensor 17 to collect image data of the user. As an example, FIG. 1 shows an image sensor 19 mounted at the top of television 6 (e.g., integrated within the television housing or provided as a separate device such as a webcam). Computing device 10 may be communicatively coupled to image sensor 19 via a suitable network described below. Further, image data collected by image sensor 19 may be used by one or more computing devices remotely located from the environment in examples in which the intelligent assistant system is implemented on such remote computing device(s) in lieu of or in addition to computing device 10.

Once the user is identified, the intelligent system may track the location of the user by processing image data using different tracking algorithms. The intelligent system may select from among the different tracking algorithms in determining a manner in which to track the user that reduces the computational expense associated with user tracking. Moreover, output from one tracking algorithm may be used as input to another tracking algorithm—and/or to non-user-tracking algorithm(s)—to increase computational efficiency and tracking robustness. Detail regarding the use of different tracking algorithms is described below with reference to FIGS. 7 and 8.

In some examples, the computing device 10 may be operatively connected with one or more other computing devices and/or sensors using a wired connection, or may employ a wireless connection via Wi-Fi, Bluetooth, or any other suitable wireless communication protocol. For example, the computing device 10 may be communicatively coupled to one or more other computing devices via a network. The network may take the form of a local area network (LAN), wide area network (WAN), wired network, wireless network, personal area network, or a combination thereof, and may include the Internet. Additional details regarding components and computing aspects of the computing device 10 are described in more detail below with reference to FIG. 23.

It will be appreciated that the computing device 10 of FIG. 1 is merely one example implementation of the intelligent assistant system of the present disclosure. Additional example implementations across two or more devices are illustrated in FIGS. 17-22 and described in more detail below.

Architecture

Figure 2:
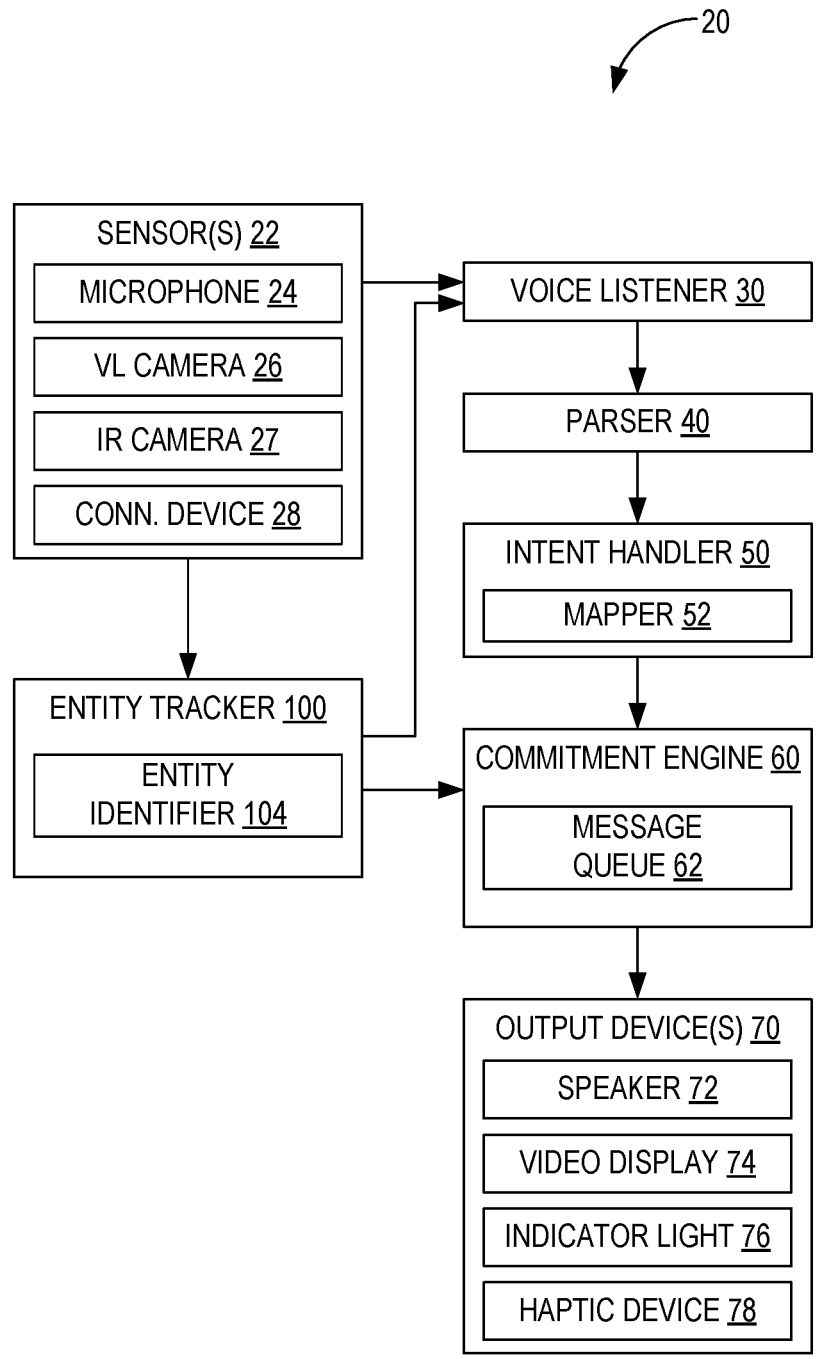
FIG. 2 schematically shows an example logical architecture for implementing an intelligent assistant system according to an example of the present disclosure.

FIG. 2 shows an example logical architecture for implementing an intelligent assistant system 20 capable of recognizing and responding to natural language inputs according to examples of the present disclosure. As described in more detail below, in various examples the system 20 may be implemented in a single computing device, across two or more devices, in a cloud-supported network, and in combinations of the foregoing.

In this example the intelligent assistant system 20 includes at least one sensor 22, an entity tracker 100, a voice listener 30, a parser 40, an intent handler 50, a commitment engine 60, and at least one output device 70. In some examples the sensors 22 may include one or more microphones 24, visible light cameras 26 (e.g., image sensor 19), infrared cameras 27 (e.g., image sensor 17), and connectivity devices 28, such as Wi-Fi or Bluetooth modules. In some examples sensor(s) 22 may comprise stereoscopic and/or depth cameras, head trackers, eye trackers, accelerometers, gyroscopes, gaze detection devices, electric-field sensing componentry, GPS or other location tracking devices, temperature sensors, device state sensors, and/or any other suitable sensor.

The entity tracker 100 is configured to detect entities and their activities, including people, animals, or other living things, as well as non-living objects. Entity tracker 100 includes an entity identifier 104 that is configured to recognize individual users and/or non-living objects. Voice listener 30 receives audio data and utilizes speech recognition functionality to translate spoken utterances into text. Voice listener also may assign confidence value(s) to the translated text, and may perform speaker recognition to determine an identity of the person speaking, as well as assign probabilities to the accuracy of such identifications. Parser 40 analyzes text and confidence values received from voice listener 30 to derive user intentions and generate corresponding machine-executable language.

Intent handler 50 receives the machine-executable language representing user intentions from the parser 40, and resolves missing and ambiguous information to generate commitments. Commitment engine 60 stores commitments from the intent handler 50. At a contextually appropriate time, the commitment engine may deliver one or more messages and/or execute one or more actions that are associated with one or more commitments. Commitment engine 60 may store messages in a message queue 62 or cause one or more output devices 70 to generate output. The output devices 70 may comprise one or more of speaker(s) 72, video display(s) 74, indicator light(s) 76, haptic device(s) 78, and/or other suitable output devices. In other examples, output devices 70 may comprise one or more other devices or systems, such as home lighting, thermostats, media programs, door locks, etc., that may be controlled via actions executed by the commitment engine 60.

In different examples the voice listener 30, parser 40, intent handler 50, commitment engine 60, and/or entity tracker 100 may be embodied in software that is stored in memory and executed by one or more processors of a computing device. Additional details regarding the components and computing aspects of computing devices that may store and execute these modules are described in more detail below with reference to FIG. 23.

Additional descriptions of the components of intelligent assistant system 20 will now be provided. In some examples, voice listener 30 may receive audio data from the surrounding environment. In some examples, such as in computing device 10 of FIG. 1, the voice listener 30 may comprise a software module that is embodied in a standalone device that comprises one or more microphones. In other examples, the voice listener 30 software module may be stored in memory of a computing device that is located remotely from the user's environment, such as in a cloud-based service. In some examples, additional data from one or more other sensors may be received and utilized by the voice listener 30 in performing its functions that are described in more detail below.

Figure 3:
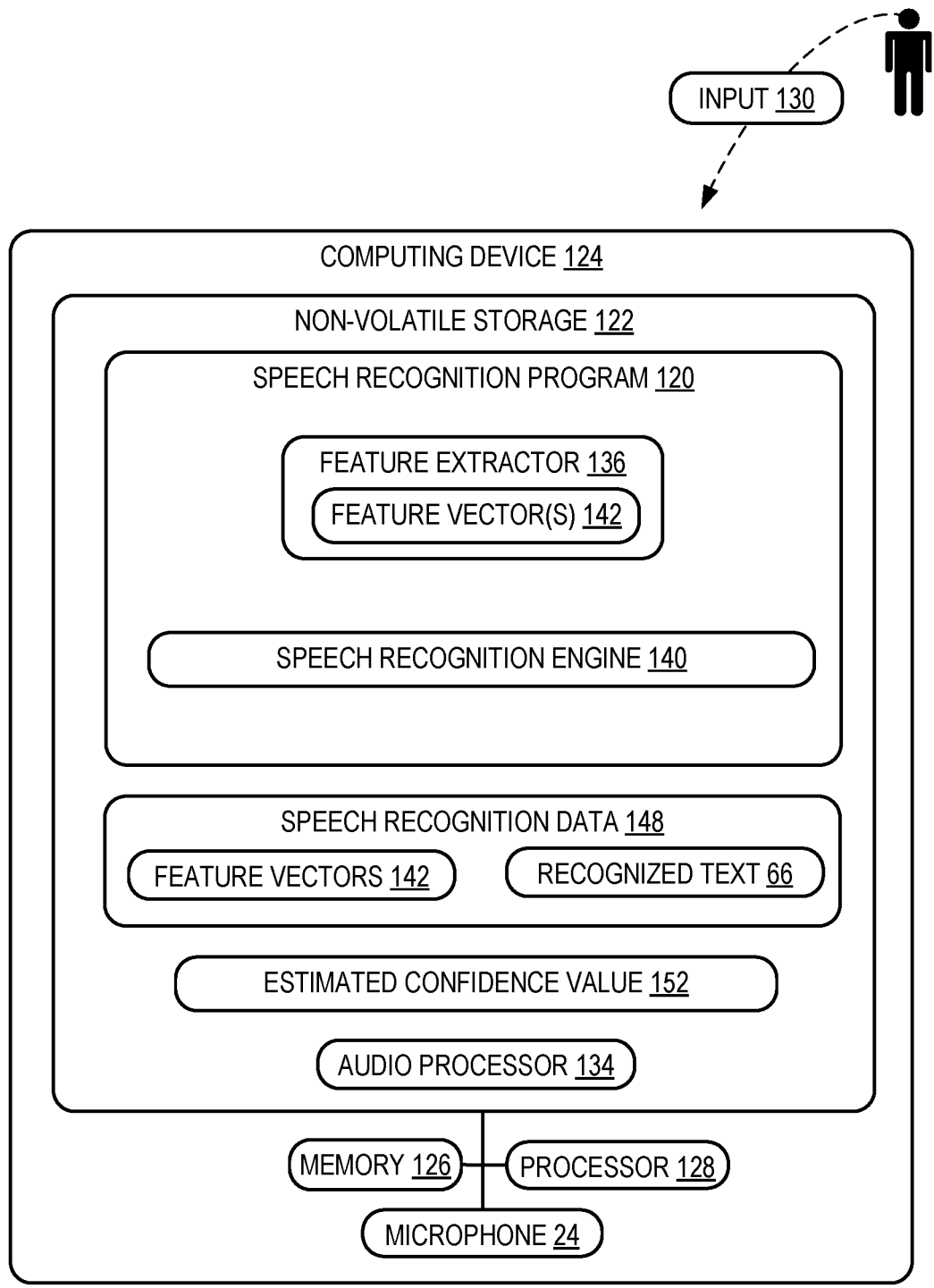
FIG. 3 schematically shows a speech recognition program that may be utilized by a voice listener according to an example of the present disclosure.

The voice listener 30 may comprise speech recognition functionality that translates audio data of spoken utterances into text. As described in more detail below, the voice listener 30 also may assign a confidence value to one or more portions of translated text, such as individual speech components, words, phrases, etc. With reference now to FIG. 3, in some examples the voice listener 30 may comprise a speech recognition program 120 stored in non-volatile storage 122 of a computing device 124. The speech recognition program 120 may be loaded into memory 126 and executed by a processor 128 of computing device 124 to perform one or more of the methods and processes for speech recognition described in more detail below.

Audio input 130 in the form of natural language speech may be captured by microphone 24 and processed by audio processor 134 to create audio data. Audio data from the audio processor 134 may be transformed by feature extractor 136 into data for processing by a speech recognition engine 140 of the speech recognition program 120.

Using the feature extractor 136 and speech recognition engine 140, the speech recognition program 120 may process feature vectors 142 and other speech recognition data 148 to generate recognized text 66. In other examples, any suitable techniques for matching feature vectors 142 to phonemes and/or other speech components may be utilized.

In some examples, the speech recognition program 120 may determine estimated confidence values 152 for one or more portions of the speech recognition data 148, such as individual speech components, words and phrases. An estimated confidence value 152 may define a statistical likelihood that the corresponding recognized text is accurate. As described in more detail below, the parser 40 of intelligent assistant system 20 may utilize such confidence values 152 in processing recognized text and determining a user's intent.

It will be appreciated that the foregoing descriptions of speech recognition techniques are merely examples, and that any suitable speech recognition technologies and processes may be utilized and are contemplated within the scope of the present disclosure.

With reference again to FIG. 2, in some examples the voice listener 30 may receive context information including associated confidence values from entity tracker 100. As described in more detail below, entity tracker 100 may determine an identity, position, and/or current status of one or more entities within range of one or more sensors, and may output such information to one or more other modules, such as voice listener 30, commitment engine 60, etc. In some examples, entity tracker 100 may interpret and evaluate sensor data received from one or more sensors, and may output context information based on the sensor data. Context information may include the entity tracker's guesses/predictions as to the identity, position, and/or status of one or more detected entities based on received sensor data. In some examples, the guesses/predictions may additionally include a confidence value defining the statistical likelihood that the information is accurate.

Additional details regarding components and computing aspects that may be used to implement voice listener 30 are described in more detail below with respect to FIG. 23.

With continued reference to FIG. 2, the voice listener 30 may send recognized text and corresponding confidence values to the parser 40. As described in more detail below, the parser 40 analyzes the text and confidence values to determine an intent of the user in speaking the received utterance. The parser 40 may translate the natural language text received from the voice listener 30 into a machine-executable language that represents a user's intention underlying the natural language.

In some examples the parser 40 may utilize a plurality of intent templates that each contain a plurality of slots that may be filled with words or terms received from the voice listener 30, or with words or terms that are based on other words received from the voice listener. In some examples where one or more slots are not filled, the parser 40 may fill these slots by examining a semantic meaning of one or more other words. For example, the intelligent assistant system 20 may tell a user, "You have 15 emails." The user may respond with an utterance, "OK, I'll go through them when I'm in the car." In response to the user's utterance, the parser 40 may fill a "commitment type" slot with the type "reminder", even though the word "reminder" itself was not in the user's utterance.

Taken together, the plurality of slots of an intent template define or otherwise characterize the intent of the user in speaking an utterance. In various different examples, the slots may comprise an action slot, a trigger slot, a commitment slot, a subject slot, a content slot, an identity slot, and various other types of slots. In some examples, each slot may embody one of three states: (1) missing information, (2) information present with unresolved ambiguity, and (3) information present with any ambiguity resolved.

Figure 4:
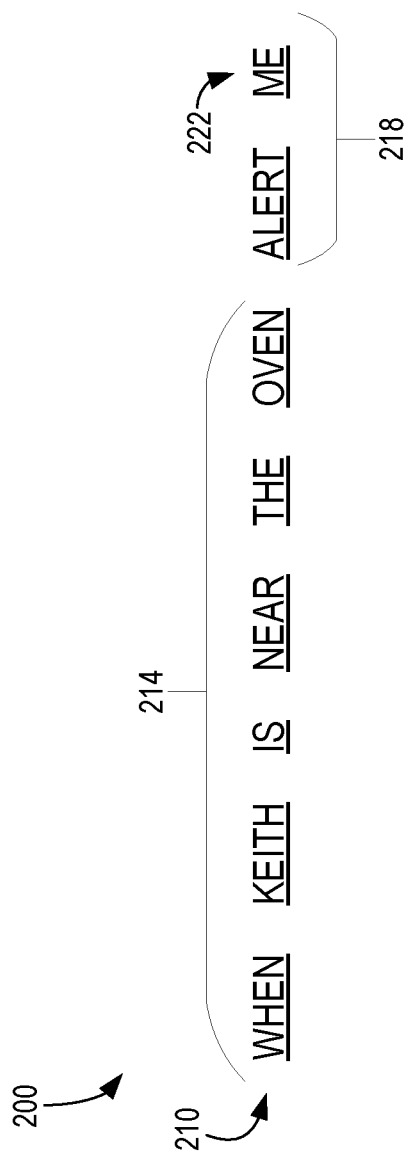
FIG. 4 shows an intent template according to an example of the present disclosure.

One example of an intent template is a commitment intent template that corresponds to an add commitment intent. With reference now to FIG. 4, one example of a commitment intent template 200 is illustrated. In this example, the parser 40 may receive text phrase 210 from the voice listener 30 that reads "When Keith is near the oven alert me." The phrase "When Keith is near the oven" may be identified as a trigger 214. The phrase "alert me" may be identified as an action 218 that is to be carried out when the trigger is detected. As described in more detail below, in some examples the parser 40 may translate this text phrase 210 into machine-executable language that is passed to the intent handler 30 for further processing.

As noted above, the parser 40 may receive accuracy confidence values from the voice listener 30 that denote a likelihood that corresponding text is accurate. In some examples and as described in more detail below, the intent handler 50 also may receive entity confidence values that are associated with entity information. In some examples, such entity confidence values and other context information may be received via the entity tracker 100.

In the present example, the word "me" in phrase 210 fills a subject slot 222. In this example, the subject slot 222 corresponds to the person or other entity to be alerted when the trigger is detected. The word "me" may be received by the parser 40 with context information that associates this word to a particular person named Joe, and with an entity confidence value, such as 90%, that denotes a level of certainty that "me" is the person "Joe."

In some examples, the intended meaning of one or more words in an intent template may not be readily apparent. For example, in phrase 210 the meaning of the word "near" may be ambiguous, as "near" is a relative term. A variety of contextual factors may influence the intended meaning of "near" and the corresponding distance contemplated in this phrase. For example, where "Keith" is an infant, the intended meaning of "near" may be based on important safety concerns of the user speaking the phrase. Where "Keith" is the husband of the user, the intended meaning of "near" may be influenced less by safety concerns and more by convenience factors, which may lead to an associated distance that is different from the case where "Keith" is an infant. In another example, the distance intended to be conveyed in the phrase "near the oven" is likely different from the distance intended to be conveyed in the phrase "near the Statue of Liberty."

Accordingly, one or more words in an intent template may be ambiguous as passed to the intent handler 50. As described in more detail below, the intent handler 50 may utilize a plurality of techniques to resolve ambiguities and to fill in slots with missing information in an intent template.

In another example, the parser 40 may receive the text phrase "Play music with Fred" from the voice listener 30. In some examples, the phrase "Play music" is often interpreted to mean that a user wants to play digital music files via a media player. However, the use of the phrase "with Fred" following "Play music" is unusual, as people typically would not use this phrasing when their intent is to play music via a media player. The parser 40 may recognize this ambiguity and may generate a list of N-best intent templates that it determines are the statistically most probable intent templates corresponding to the user's actual intent. In some examples, the intent handler 50 may use additional context information to select an intent template from the list of N-best intent templates.

In some examples, the parser 40 may analyze received text to form a decision tree of the user's intent. In some examples, the parser 40 may generate If-Then statements (or rules) from the received text. Each If-Then statement may comprise a corresponding trigger and an action. Whenever the conditions of the trigger are satisfied, the action is performed. The resulting If-Then statements can perform a wide variety of tasks, such as home security ("text me if the motion detector in the back yard is activated"), home automation ("turn on the fireplace when I arrive home"), personal organization ("collect my email receipts for charitable donations into a spreadsheet"), health-related tasks ("remind me to eat protein if I run more than 7 miles"), and many others.

In some examples, the parser 40 may use an ensemble of two techniques to generate If-Then statements and/or derive an intent from the text received from the voice listener 30: (1) a recurrent neural network (RNN) architecture in the form of a long short-term memory (LSTM) network, and (2) a logistic regression model. In some examples, a graph long short term memory (graph LSTM) neural network may be utilized to extract from received text semantic meanings and relationships between words that are inherent to natural language. For example, text may be parsed using a graph LSTM neural network to extract cross-sentence n-ary relationships using several graph LSTM units arranged according to the syntactic relations of terms in the segment of text. These syntactic relationships between words may be tracked in the graph LSTM neural network to allow artificial intelligence and machine learning techniques to identify entities and their context within the text and from the grammatical structure in which they exist.

For example, context that identifies the nouns to which pronouns refer, the adverbs that modify given verbs, the prepositional phrases that affect a given word, etc., may be incorporated into the various words to enable more accurate searches of the contents of natural language documents. Additional descriptions of and examples of using graph LSTM neural networks to extract semantic meanings and relationships between words are provided in U.S. patent application Ser. No. 15/395,961, entitled GRAPH LONG SHORT TERM MEMORY FOR SYNTACTIC RELATIONSHIP DISCOVERY, filed on Dec. 30, 2016, the entire contents of which are incorporated herein by reference.

In some examples, the parser 40 may receive and process text to graph nodes (e.g., words, phrases, characters, etc.) and edges (e.g., dependency links between nodes) in individual phrases and across boundaries of phrases. In various examples, the graphing may include identifying one or more links (e.g., syntactic, semantic, co-reference, discourse, etc.) between nodes in the text. The links can include intra-phrase and inter-phrase links between nodes. For example, a link can represent a relationship between the root of one phrase and the root of an adjacent phrase. For another example, a link can represent a relationship between two words in a phrase, such as the modifier "Annie's" to the word "lunch." Additional details regarding graphing nodes and edges in phrases and across boundaries of phrases is disclosed in U.S. patent application Ser. No. 15/173,349, entitled RELATION EXTRACTION ACROSS SENTENCE BOUNDARIES, filed on Jun. 3, 2016, the entire contents of which are incorporated herein by reference.

Additional details regarding components and computing aspects that may be used to implement parser 40 are described in more detail below with respect to FIG. 23.

As described above, in some examples the parser 40 passes an intent template to the intent handler 50 for further processing. The intent handler 50 comprises a multi-step pipeline that may resolve ambiguous information and/or information that is missing from an intent template. As described in more detail below, the intent handler 50 may utilize a plurality of techniques to resolve ambiguities and fill in missing information slots with respect to an intent template. In some examples, the intent handler 50 may utilize domain-specific information and domain-specific reasoning to resolve ambiguities, complete missing information, and otherwise clarify an intent template to more closely correspond to the actual intent of the user.

In some examples, the intent handler 50 may glean knowledge regarding the user's intent by analyzing prior utterances of the user in a conversation history, and may utilize such insights to resolve ambiguities and add missing information to an intent template. Once the intent handler 50 has sufficiently clarified ambiguities and completed missing information, a corresponding commitment may be generated and passed to the commitment engine 60 for execution.

The intent handler 50 may be configured to process multiple intent templates that may comprise a conversation. For purposes of the present disclosure and as described in more detail below, a conversation may comprise a plurality of information and other data related to one or more exchanges between the user and the intelligent assistant system 20. In different examples, such information and data may comprise words and/or phrases spoken by a user, queries presented to the user by the intelligent assistant system 20, sensor data received from one or more sensors, context information such as person and/or identity information, etc.

As described in the use case examples provided below, the intent handler 50 may comprise a plurality of resolvers that translate intent templates and their associated data received from the parser 40 into internal data references. To address slots that comprise missing and/or unresolved information in an intent template, the intent handler 50 may utilize the plurality or resolvers in a multi-stage process. In some examples, each of the resolvers may be specifically programmed to handle issues associated with a particular intent template that may be received from the parser 40.

Examples of resolvers may include lookup resolvers that translate proper names, aliases, and other identifiers into internal representation data (for example, "Bob" is translated to an internal representation of the person "Bob", such as Bob's contact information). Examples of resolvers may include anaphoric resolvers that address expressions having an interpretation that depends upon an antecedent or postcedent expression in context (for example, "she" is translated to a slot representing "a personal identity of the pronoun 'she'"), and deixis resolvers that address words and phrases, such as "here" or "there", that cannot be fully understood without additional contextual information (for example, "there" may translated to a slot representing "where is there?"). In other examples, many other forms and types of resolvers may be utilized.

Figure 5:
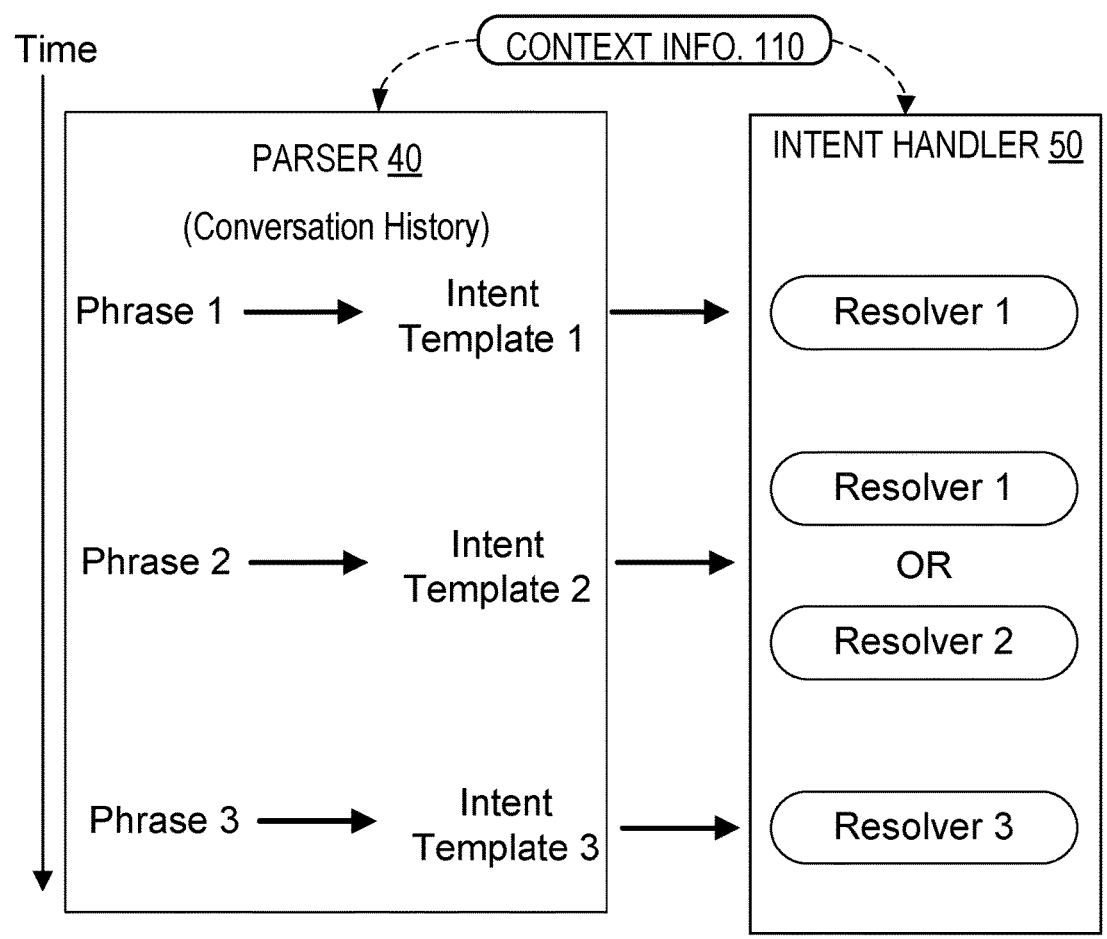
FIG. 5 schematically shows a parser and an intent handler processing a portion of a conversation according to an example of the present disclosure.

With reference now to FIG. 5, one example of the parser 40 and intent handler 50 processing a portion of a conversation is schematically illustrated. In this example, a first phrase 1 is parsed by the parser 40 into an intent template 1. The parser 40 provides intent template 1 to the intent handler 50, which utilizes a first resolver 1 to resolve ambiguities and/or missing information in this intent template. A second intent template 2 corresponding to a second phrase 2 is received from the parser 40. As described in more detail below, the intent handler 50 may analyze the intent template 2 along with context information 110 to determine whether to utilize first resolver 1 or second resolver 2 to resolve the intent template 2. A third intent template 3 based on a third parsed phrase 3 may then be received by the intent handler 50. The intent handler 50 may utilize a third resolver 3 to resolve intent template 3. Additional details and use case examples of analyzing intent templates with resolvers are provided below.

In some examples the intent handler 50 may determine whether two or more intent templates should be fused or merged together to continue with an existing conversation path. If the intent handler 50 determines that the two or more intent templates should be fused together, then the intent handler may fuse the data associated with the two or more intent templates and continue following the existing conversation path with the fused data. If the intent handler 50 determines that the two or more intent templates should not be fused together, then a new topic may be started using the most recently received intent template.

As described in more detail below, where a slot of an intent template has missing information, the intent handler 50 may perform data gathering operations (such as to ask the user to clarify or provide information, or try to gather the information in another way) in order to populate information in the slot. Once each slot contains information, the intent handler 50 may determine if the information in each slot is unambiguous. For information identified as ambiguous, the intent handler 50 may apply one or more of a variety of techniques to resolve the ambiguity.

With reference again to FIG. 2, in some examples the intent handler 50 may comprise a mapper 52 that maps one or more system goals to a corresponding user intent(s). Examples of system goals may include clarifying ambiguities, acquiring additional information from a user, etc. In some examples, mapper 52 may internally rephrase system goals as user intents or goals. For example, mapper 52 may map information the system needs, such as information to resolve an ambiguous intent, to a user intent that the user would have triggered in providing that information. In other words, mapper 52 may map information to the intent that would have been resolved from an utterance that a user would have spoken in order to generate the intent. In some examples, mapper 52 may map a system goal to a word or phrase the user would have said to generate the same outcome.

In some examples, where the system needs information from a user to resolve a user intent, the system may internally cue a state that is equivalent to the state the system would have been in if the user had provided input (such as an utterance) containing all the components of the intent except for the needed information. In other words and in some examples, the system may assume that the user has already provided more input, with that input missing only one or more specific slot(s) corresponding to the needed information. In this manner, the intent handler 50 may continually utilize whatever user input is provided. In some examples, this allows the system to reuse components, such as intent templates. Accordingly and in these examples, by causing the intent handler 50 to assume that user intents (versus system goals) are driving its operation, the system may internally reuse corresponding logic and may understand such user intents with greater depth and richness.

In some examples, the system may have a goal of acquiring information from a user to proceed with deriving a user intent. In a first example, a user may speak two utterances: "Book me a flight to California tomorrow; The flight needs to be to San Francisco." In the first utterance, the user indicates an intent to book a flight, and in the second utterance the user narrows the intent to a flight to San Francisco. In both utterances, a user intent is specified.

In another example, the user speaks a first utterance "Book me a flight tomorrow." The system may respond with a query "Where do you want to fly to?" The user may then respond, "To San Francisco." Upon generating the system query, the mapper 52 may map the intent handler's goal (acquiring information of the user's destination) to a user intent. For example, the mapper 52 may presume that the user is about to provide this information as if it were the user's intent.

In some examples, by configuring the mapper 52 to presume that a user intent is driving its operation, the system may minimize the code to perform these operations and reuse corresponding logic. In this manner, the system may understand such user intents with greater depth and richness. Accordingly, in these examples the system may utilize code for the intent handler 50 and mapper 52 that comprises a user-intent only system, as opposed to utilizing multiple specialized pieces of code to manage all ambiguities and otherwise handle multiple corresponding tasks and discrete situations.

Additional details regarding components and computing aspects that may be used to implement intent handler 50 are described in more detail below with respect to FIG. 23.

Figure 6A:
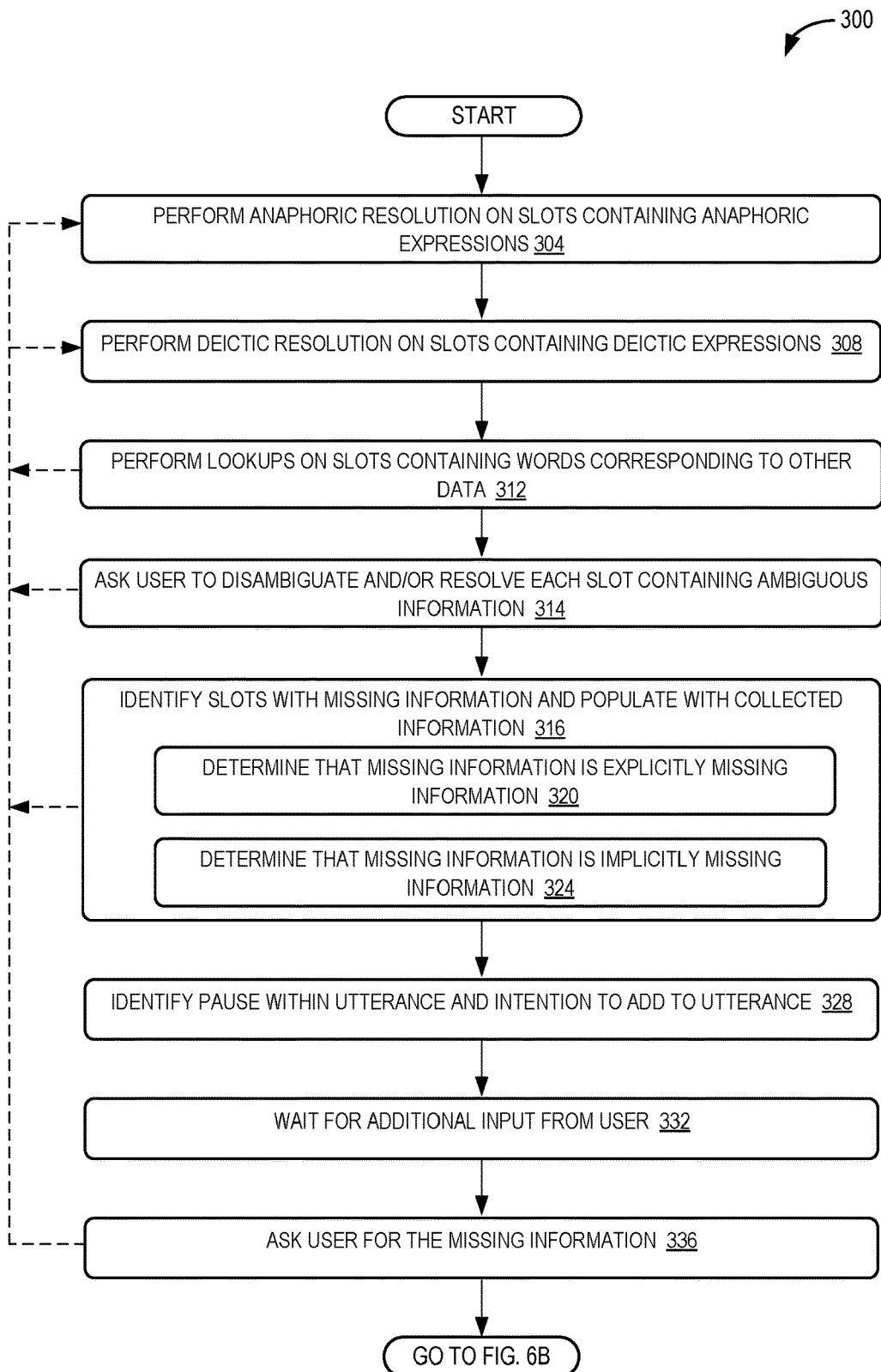
FIGS. 6A and 6B show a method for addressing missing and/or unresolved information in an intent template according to examples of the present disclosure.
Figure 6B:
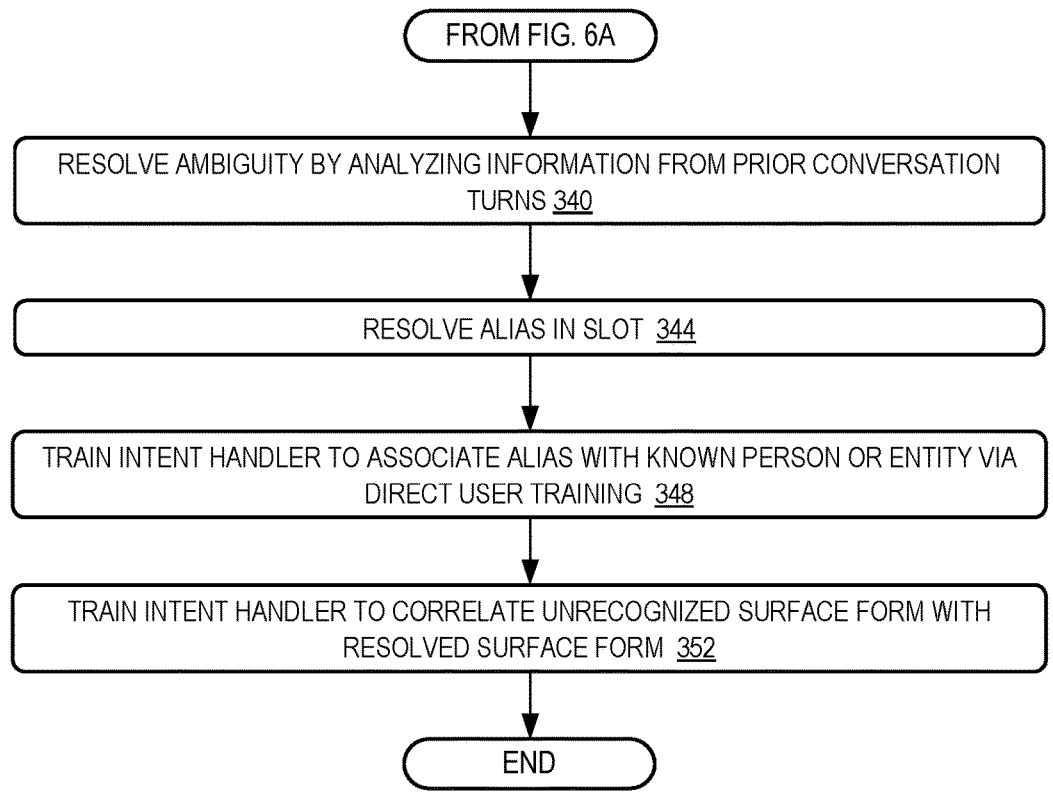

With reference now to FIGS. 6A and 6B, a flow chart of a method 300 for addressing missing and/or unresolved information in an intent template according to examples of the present disclosure is provided. The following description of method 300 is provided with reference to the software and hardware components described herein. It will be appreciated that method 300 also may be performed in other contexts using other suitable hardware and software components.

Additionally, while the blocks of method 300 are described and illustrated in a particular sequence, in different examples the order of execution may vary. In some examples one or more of the blocks may not be performed. In some examples, context information 110 from the entity tracker 100 may be utilized to determine an order of execution and/or which block to execute next.

With reference to FIG. 6A, at 304 the method 300 may include performing anaphoric resolution on slots that contain an anaphor or a cataphor. For example, in the phrase "When he is near the oven alert me", the word "he" is an anaphoric expression that refers to a person who was referenced earlier in the conversation. Additionally and as described in more detail below, by understanding and resolving the intent of the user via intent template(s) received from the parser 40, the intent handler 50 may augment this anaphoric resolution process with one or more other techniques, such as grounding and repair techniques described in more detail below, to more accurately determine the person who corresponds to an anaphoric expression.

At 308 the method 300 may include performing deictic resolution on slots that contain words that cannot be fully understood without additional contextual information. Examples of deictic expressions include words having a fixed semantic meaning and a denotational meaning that varies depending on time and/or place. For example, in the phrase "When he is near the oven alert me", the word "near" is a deictic expression whose meaning depends on contextual information. Additionally and as with anaphoric expressions, the intent handler 50 may augment its deictic resolution process with one or more other techniques, such as grounding and repair techniques, to clarify the intended meaning of the deictic expression.

In some examples, deictic resolution may be performed using data from one or more sensors, such as captured image data, audio data, position information, etc. For example, when a user points at an oven, image data showing the user's finger pointing at the oven may utilized by the entity tracker 100 to identify the oven and to determine that the user is pointing at the oven. While pointing the user may speak the utterance "Let me know when this gets hot." Using this information, the intent handler 50 may resolve the word "this" into "oven", and more particularly into the oven at which the user is pointing.

In another example, a user may speak "If my child comes in here let me know." The system may use location data of the user to resolve the word "here" into the current location of the user. In another example, two people walk into the room, and one person asks the system: "Do we have any messages?" Using sensory information, such as image data and/or audio data to identify both people, the system may perform deictic resolution to resolve "we" to the identities of the two people in the room.

At 312 the method 300 may include performing lookups for slots containing words that correspond to other data available to the intent handler 50. Examples of other data that may be available to the intent handler 50 include contact information, social graph data, calendar information, email data, photo metadata, and the like. Information accessed in performing such lookups may be populated in a slot to replace the word(s) presently occupying the slot. For example, in the phrase "Tomorrow remind me to drop the car at autodealer1", the word "autodealer1" may correspond to the auto repair shop where the user regularly has her car repaired. "Autodealer1" may be represented by a contact entry in the user's contact database. Accordingly, the intent handler 50 may locate such contact entry and may utilize the "Autodealer1" contact data for the word "autodealer1" in the intent template.

At this point, the method 300 may return to 304 and/or 308 to perform anaphoric resolution and/or deictic resolution, as needed, on information populated in a slot. Additionally, the intent handler 50 may augment its lookup process with one or more other techniques, such as grounding and repair techniques, to clarify the intended person or entity that corresponds to the information currently present in the slot.

At 314 the method 300 may include asking the user to disambiguate and/or resolve one or more slots containing ambiguous information. For example, where a user asks the system to "Call Patrick", and the user's contacts database includes a Patrick Doe and a Patrick Smith, the system may ask the user, "Which Patrick would you like to call, Patrick Smith or Patrick Doe?"

At 316 the method 300 may include identifying slots with missing information and populating these slots with collected information. Various techniques may be utilized to generate and/or retrieve such information. For example and as described in more detail below, slots with missing information may be treated differently depending upon whether the information is determined to be explicitly missing or implicitly missing.

For example, at 320 the method 300 may include determining that the missing information is explicitly missing information. In one example, by analyzing a text phrase the intent handler 50 may determine that the user's utterance suggests that information for a particular slot should be provided in the utterance. Where such information is missing, the information may be determined to be explicitly missing information. For example, consider the phrase "When Gary comes into the room with the others introduce." The intent handler 50 may determine that this phrase comprises a content slot corresponding to the subject of the verb "introduce", and that this content slot is missing information. In this example, the context of the phrase comprises the words that precede "introduce", these words' order and meaning, the factor that the phrase ends with the word "introduce" without naming the subject of the introduction, and the factor that the phrase constitutes a grammatically incomplete sentence.

The intent handler 50 may determine that this context does not resolve the ambiguity associated with this missing information. For example, while the user may be intending to introduce Gary to the others, other intentions are also possible (such as introducing one of the others to Gary). Accordingly, the intent handler 50 determines that the ambiguity associated with this missing information cannot be presently resolved. Given this ambiguity and as described in more detail below, the intent handler 50 may use one or more other techniques (such as querying the user, "Whom do you want to introduce?") to collect the missing information. In some examples as described in more detail below, the intent handler 50 may wait for the receipt of additional user input before querying the user. In some examples, additional information from the entity tracker 100 may be utilized to resolve the ambiguity and collect the missing information.

In some examples, where information for a trigger slot or an action slot of a commitment is missing, and based at least in part on context information 110 generated by the entity tracker 100, the intent handler 50 may proactively propose an action to the user. In one example, a user may speak the utterance "Alice." The intent handler 50 may receive an intent template with an empty action slot and a trigger slot partially completed with the name "Alice." The context information 110 may include an identity prediction with 85% confidence that "Alice" corresponds to the "Alice Jones" in the user's contact database. The context information 110 also may include a location prediction with 95% confidence that Alice Jones is located in the basement laundry room of the user's house. Based at least in part on this context information 110, the intent handler 50 may proactively ask if the user would like to communicate with Alice Jones, such as via an in-home intercom system.

At 324 the method 300 may include determining that the missing information is implicitly missing information. In one example, the intent handler 50 may determine that a user did not intend to provide information that is missing from a particular slot. Such missing information may be determined to be implicitly missing information. For example, consider the phrase "When Gary walks into the kitchen say Hello." The intent handler 50 may determine that the command "say Hello" corresponds to the user saying Hello to another person. Accordingly, the intent template corresponding to this phrase may comprise a content slot that follows the words "say Hello" and which normally contains the name or other identifier of the person the user intends to say Hello to (e.g., "Say Hello to Suzanne").

In this example, because the phrase ended with the word "Hello", such content slot is missing information that identifies the person intended. The context of this phrase comprises the words that precede "Hello", these words' order and meaning, and the factor that the phrase constitutes a grammatically complete sentence. Given this context, the intent handler 50 infers that the user intends for the command "say Hello" to apply to Gary. In other words, the context associated with this phrase indicates that the content slot following the words "say Hello" should be filled with "Gary." In this manner, the intent handler 50 may resolve this particular ambiguity associated with the missing information without querying the user for additional input. After populating a slot with missing information as described above, the method 300 may return to 304 and 308 to perform anaphoric resolution and/or deictic resolution, as needed, on the information populated in the slot.

In some examples and as noted above, the intent handler 50 may query the user for information that is missing from a slot. For example, the intent handler 50 may broadcast a spoken word query to the user via a speaker of a mobile phone. In some examples, however, information missing from a slot may be the result of an intended or unintended pause by the user that interrupts the user before the user completes her utterance. Accordingly and at 328, in some examples the method 300 may include identifying a pause within an utterance from a user along with an intent of the user to continue speaking and add to the utterance.

For example, a user may pause mid-utterance to think about what she should say next. In other examples, a user may be interrupted mid-utterance by an external event, such as another person speaking, distracting activity from the user's environment such as a loud noise or bright light, or a variety of other external activities.

In one example and with reference to the description above for identifying explicitly missing information, the phrase "When Gary comes into the room with the others introduce" may be determined to comprise a content slot that corresponds to the subject of the verb "introduce" and is missing information. Based on the empty content slot, other aspects of the phrase, and/or the context in which it is spoken, the intent handler 50 may identify a pause at the end of this phrase along with a predicted intent of the user to continue speaking and to add a subject to the verb "introduce."

At 332 and in response to identifying the pause, the method 300 may include waiting for additional input from the user before asking the user for more information. In some examples, the intent handler 50 may wait for a predetermined period of time, such as 1 second, 2 seconds, or other length of time that does not create a negative user experience for the user. In this manner, the system may avoid interrupting the user mid-utterance where the user intends to begin speaking again and to add to the utterance.

In some examples, an engagement timer may be started whenever a user starts speaking. The engagement timer may run for a predetermined period of time during which the user may be designated as "engaged." The predetermined period of time may be 1 second, 2 seconds, or other duration. If the system needs to ask for input or otherwise audibly converse with the user before the predetermined period of time expires, the system may use interruption language constructs that may provide for a more gentle interruption of the user's current potential engagement. Examples of interruption language constructs include "by the way" and "additionally". In some examples, such language constructs may be used even where the user has stopped speaking and/or the current conversation has "timed out," and the system is not presently listening to the user.

At 336 the method 300 may include querying the user for information missing from a slot. In some examples, the intent handler 50 may ask the user for information missing from one or more slots of an intent template. For example, regarding the phrase "When Gary comes into the room with the others introduce" and its explicitly missing information in the content slot following the word "introduce," the intent handler 50 may broadcast a spoken word query to the user asking "Whom do you want to introduce?" In other examples, the intent handler 50 may query the user via other interfaces, such as by displaying a query on a display device.

When the intent handler 50 receives a response to its query from the user (via the voice listener 30 and parser 40), the intent handler may populate the slot with the response. At this point, the method 300 may return to 304 and the steps following to analyze this newly-added information for any ambiguities as described above.

With reference now to FIG. 6B, at 340 the method 300 may include resolving an ambiguity by analyzing information from a prior conversation turn. In different examples, the method may analyze both utterances as a single or combined utterance, and/or may use one or more elements from a prior utterance to generate one or more slots in an intent template for a current utterance.

In some examples, the intent handler 50 may analyze content from a previous intent template and/or one or more slots of the template. In some examples, the intent handle 50 may determine that a current utterance is additive to a previous utterance. For example, consider the phrase "When Justin is near the oven, alert Erich." Justin may be a toddler, Erich the toddler's father, and the user speaking the phrase may be Justin's mother. The intent handler 50 may receive a first intent template for this phrase. A first resolver may resolve the template and establish a commitment that broadcasts a warning to Erich via Erich's mobile phone when Justin is within 1 meter of the oven in Erich's kitchen.

After speaking this first phrase, Justin's mother may pause for a brief period of time, such as 3 or 4 seconds. After this pause, she may speak a second phrase "and me" which is received by the parser 40. As this phrase contains no action component, the parser 40 may generate a second intent template that has an unknown or unresolved intent. In this example, and because the intent associated with this second phrase is presently unknown, the intent handler 50 may select a second, different resolver to address this second intent template.

Based at least in part on this second phrase beginning with the conjunction "and" followed by the pronoun "me", the second resolver may determine that Justin's mother intends to refer to a prior utterance. The second resolver may utilize an anaphoric resolution technique to associate the word "me" to Justin's mother. By using this data and analyzing the previously-established commitment, the second resolver may determine that the intent associated with the second phrase "and me" is related to the intent associated with the prior phrase "When Justin is near the oven, alert Erich." Accordingly, the second resolver may modify the previously-established commitment to broadcast a warning to both Erich and Justin's mother when Justin is within 1 meter of the oven in the kitchen.

As another example, consider again the phrase "When Justin is near the oven, alert Erich." After speaking this first phrase, Justin's mother may pause for a few seconds and then speak a second phrase "and also if he's close to the pool." As this phrase contains a trigger ("if he's close to the pool") and no action component, the parser 40 may generate a second intent template that has an unknown or unresolved intent. Also, in this example the anaphoric expression "he's" could refer to either of the two names in the preceding phrase (Justin or Erich).

A resolver may determine that it is most probable that the reference to "he" in the trigger of the second phrase is intended to refer to a male person mentioned in another, prior trigger. Based at least in part on this second phrase beginning with the conjunction "and" followed by the words "also" and "if", the second resolver may determine that Justin's mother intends to refer to a prior utterance and to modify a trigger or add another trigger to an action of the previously-established commitment. By using this data and analyzing the previously-established commitment, the second resolver may determine that the intent associated with the second phrase "And also if he's close to the pool" is related to the intent associated with the prior phrase "When Justin is near the oven, alert Erich." Accordingly, the second resolver may modify the previously-established commitment to broadcast a warning to Erich when Justin is either within 1 meter of the oven in the kitchen or within 3 meters of the pool.

In some examples, the intent handle 50 may determine that a current utterance is intended to amend one or more previous utterances. For example, consider the phrase "Please remind me to call Jeff at six o'clock." After speaking this first phrase, the user may pause for a brief moment and then speak a second phrase "I mean Mike." As this phrase contains an ambiguous phrase without a clear trigger or action component, the parser 40 may generate another intent template that has an unresolved intent.

By analyzing the immediately preceding commitment associated with the prior utterance "Please remind me to call Jeff at six o'clock," a resolver may determine that the intent associated with the second phrase "I mean Mike" is most likely related to the intent associated with the prior phrase "Please remind me to call Jeff at six o'clock." Accordingly, this resolver may modify the previously-established commitment to replace the reference to "Jeff" in the action component of this phrase with "Mike."

In another example, consider the phrase "Please remind me to call Jeff and Mike at six o'clock." After speaking this first phrase, the user may pause for a brief moment and then speak a second phrase "not Mike." As this phrase contains an ambiguous phrase without a clear trigger or action component, the parser 40 may generate another intent template that has an unresolved intent.

By analyzing the immediately preceding commitment associated with the utterance "Please remind me to call Jeff and Mike at six o'clock," a resolver may determine that the intent associated with the second phrase "not Mike" is most likely related to the intent associated with the prior phrase "Please remind me to call Jeff and Mike at six o'clock." Accordingly, this resolver may modify the previously-established commitment to remove the reference to "and Mike" from the action component of this phrase.

In some examples and as described in more detail below, where two or more people are having a conversation, the system may follow the conversation and determine when the active participant (i.e., the person currently speaking) changes in the conversation. In these examples, when the system determines that the current speaker has changed, the system may determine whether the information contained in the new speaker's speech is a continuation of the existing conversation topic/session, or whether a new topic/session has been introduced. Where the new speaker's information is a continuation of the existing conversation topic/session, this determination may be used by the intent handler 50 to resolve ambiguities, complete missing information and/or otherwise clarify the intent of each speaker. For example, such conversation and topic/session tracking may enable the system to assist a team that is working and speaking collaboratively to complete a task. In some examples, the system may track multiple conversations that are occurring simultaneously or otherwise overlapping, and may interact with participants in each conversation as appropriate for each conversation.

In some examples, the intent handler 50 may determine that an intent associated with a newly received phrase is not related to the intent of an immediately preceding commitment. For example, an intent template corresponding to the utterance "Call Justin" may be received and processed by a first resolver into a first commitment. The first resolver may determine that the content slot ("Justin") of the action "Call Justin" is ambiguous because the user has both a Justin Smith and a Justin Doe in the user's contacts database. Accordingly, the first resolver may respond with a query to the user of "Which Justin—Justin Doe or Justin Smith?" In this example, the user responds with an unrelated response, "Please record TV Show A tonight."

The first resolver may analyze this response and its corresponding new intent template by referring to the immediately preceding intent template and its missing content slot. Because the user's response is completely unrelated to the query just presented to the user, the first resolver determines that the new intent template represents a new intent of the user, and thus the new intent template should not be fused with the preceding intent template. Accordingly, the first resolver is replaced by a second resolver that proceeds to analyze the new intent template and establish a new conversation.

At 344 the method 300 may include resolving an alias that refers to a known person or entity by a different name or representation. In one example, a user may refer to "Mimi" in an utterance. The user's contacts database may not contain a contact with the name "Mimi." However, in prior conversations tracked by the intent handler 50, the user's sister may have referred to herself as "Mimi" when speaking with her grandson. A data store accessible to the intent handler 50 may have created an association between the user's sister and the alias "Mimi." By searching the data store for instances of "Mimi" and finding the association between the user's sister and the alias "Mimi", the intent handler 50 may resolve the name "Mimi" in the user's utterance to the user's sister.

At 348 the method 300 may include training the intent handler 50 to associate an alias with a known person or other entity via direct user training input. For example, the user may speak a command, "When I say Mimi I'm referring to my sister Suzanne." The intent handler 50 may create a link between "Mimi" and the user's sister Suzanne, such as by modifying a contacts database file containing information identifying Suzanne.

In a similar manner, at 352 the method 300 may include training the intent handler 50 in a real-time or batch-mode manner to correlate an unrecognized surface form with a newly resolved surface form. For example, the intent handler 50 may be unable to recognize a particular surface form it receives. The intent handler 50 may clarify this surface form via one or more grounding and repairing techniques. In this manner and going forward, the unrecognized surface form subsequently may be correlated with the clarified surface form, whereby the intent handler 50 now may recognize the previously-unrecognized surface form.

In another example, a user may be traveling across New York City in a car for hire. The user may speak a first request to his smartphone, with a middle portion of the phrase unintelligible: "When I get to [unintelligible] call her mobile phone." By analyzing this phrase along with context information, such as motion data indicating the user is traveling in a car, the intent handler 50 may infer that the unintelligible portion of the phrase corresponds to a location slot.

The intent handler 50 may query the user, "Where do you want to do this?" The user may reply with a second response, "Madison." The parser 40 may receive the text "Madison" from the voice listener 30, and may generate a list of the statistically most probable meanings for this word that correspond to the user's actual intent. In this example, the user may have a close friend named Madison, and may have used her name in many spoken requests to the intelligent assistant system 20. Accordingly, the parser 40 may determine that the user's close friend "Madison" is the most probable intention underlying the user's utterance.

However, based its analysis of the user's first request and other context information, such as the motion data, the intent handler 50 determines that the expected user response to the query "Where do you want to do this?" most likely will be location information. The intent handler also may analyze mapping data that indicates the user will arrive at a Madison Avenue address in five minutes. Accordingly and based at least in part on this context information, the intent handler 50 may not select the user's close friend "Madison", despite the parser's prediction that this is the statistically most probable meaning for this word. Instead, the intent handler may use this context information to resolve this ambiguity by selecting Madison Avenue as the intention of the user.

In some examples where the intent handler is unable to resolve an intent from an utterance, the system may still offer to take one or more actions. For example, if a user makes the declarative statement "Silver looks nice", the system may not understand the user's intent underlying this utterance. Instead of ignoring the user because the system doesn't understand what it should do with the utterance, the system may offer to display photos of silver jewelry, play music, or take some other action.

It will be appreciated that method 300 is provided by way of example and is not meant to be limiting. Therefore, it is to be understood that method 300 may include additional and/or alternative steps relative to those illustrated in FIGS. 6A and 6B. Further, it is to be understood that method 300 may be performed in any suitable order. Further still, it is to be understood that one or more steps may be omitted from method 300 without departing from the scope of this disclosure.

As described above, when the intent handler 50 has sufficiently clarified and resolved the user's intent, a corresponding commitment may be generated and passed to the commitment engine 60 for execution. As described in more detail below, the commitment engine 60 may utilize one or more cost functions to determine one or more costs associated with executing or not executing a commitment and, in some examples, with outputting or not outputting a message to the user.

Where the commitment engine 60 receives multiple commitments, the commitment engine may prioritize the commitments for presentation to a user. In one use case example, the commitment engine 60 may be storing seven commitments for user Eddie, with each commitment set to convey a different message to Eddie. Each message also may be staged to be audibly broadcast to Eddie when he arrives home from work today. The commitments and corresponding messages may include task reminders to take out the garbage, fix the leaky faucet and put the roast in the oven, and informational reminders that property taxes are due tomorrow and that he needs to buy eggs. If each of these messages is broadcasted to Eddie when he walks in the door, he may be less likely to effectively manage and/or prioritize the corresponding tasks.

Additionally, in some examples Eddie's current context may make it more difficult for him to comprehend and effectively manage these messages. For example, if Eddie is talking on his phone when he walks in the door, and seven messages are audibly broadcast to him at that time, he may have difficulty hearing or even comprehending the messages.

Accordingly and in some examples, factors related to the receptivity of the user to receiving input, the importance of a commitment to a particular user, and/or the user's current context may be determined. Machine learning techniques may be applied to such factors and other data to learn from such information and make related predictions in the future. As described in more detail below, one or more cost functions may be used to determine costs associated with executing or not executing a commitment. Using these techniques, the commitment engine 60 may intelligently manage the execution of commitments and corresponding messages to align with a particular user's preferences and current context.

In some examples, and in response to changing contexts and/or new data inputs, the commitment engine 60 may modify priorities, timings, and other aspects of commitments, messages and their execution. For example and as described in more detail below, the commitment engine 60 may receive context information 110, such as entity identity, entity position, and entity status information, from the entity tracker 100. Such context information 100 may be used by commitment engine 60 to determine whether a particular message, notification, or commitment should be presented to a user or otherwise executed.

In some examples, one or more previously defined components of a commitment may be updated based on new input received by the commitment engine 60. For example, the intent handler 50 may generate and pass a commitment including a trigger component that refers to a separately-defined term. In one example, a user may speak the utterance: "Please notify my kids to come home 60 minutes before curfew." The term "curfew" may be associated with the user's profile that is stored in a data store, and may currently have a value of 11:00 pm. By accessing the user's profile stored in a data store, the intent handler 50 may resolve the term "curfew" to 11:00 pm, and may pass to the commitment engine 60 a corresponding commitment to send a text message at 10:00 pm (60 minutes before 11:00 pm) to the user's children with instructions to come home.

Subsequently to this utterance, the user may update her kids' curfew time to one hour later, such as by speaking: "Update the kids' curfew to Midnight." The commitment engine 60 may identify this update its modification to the value of "curfew," and may determine that it affects the previously-received commitment. Accordingly, the commitment engine may correspondingly modify the trigger of the previously-received commitment by updating the value of "curfew" to Midnight, which results in the commitment sending the text message at 11:00 pm instead of 10:00 pm. The commitment engine 60 also may modify the value of "curfew" in the user's profile stored in the data store.

Additional details regarding components and computing aspects that may be used to implement commitment engine 60 are described in more detail below with respect to FIG. 23.

Figure 7:
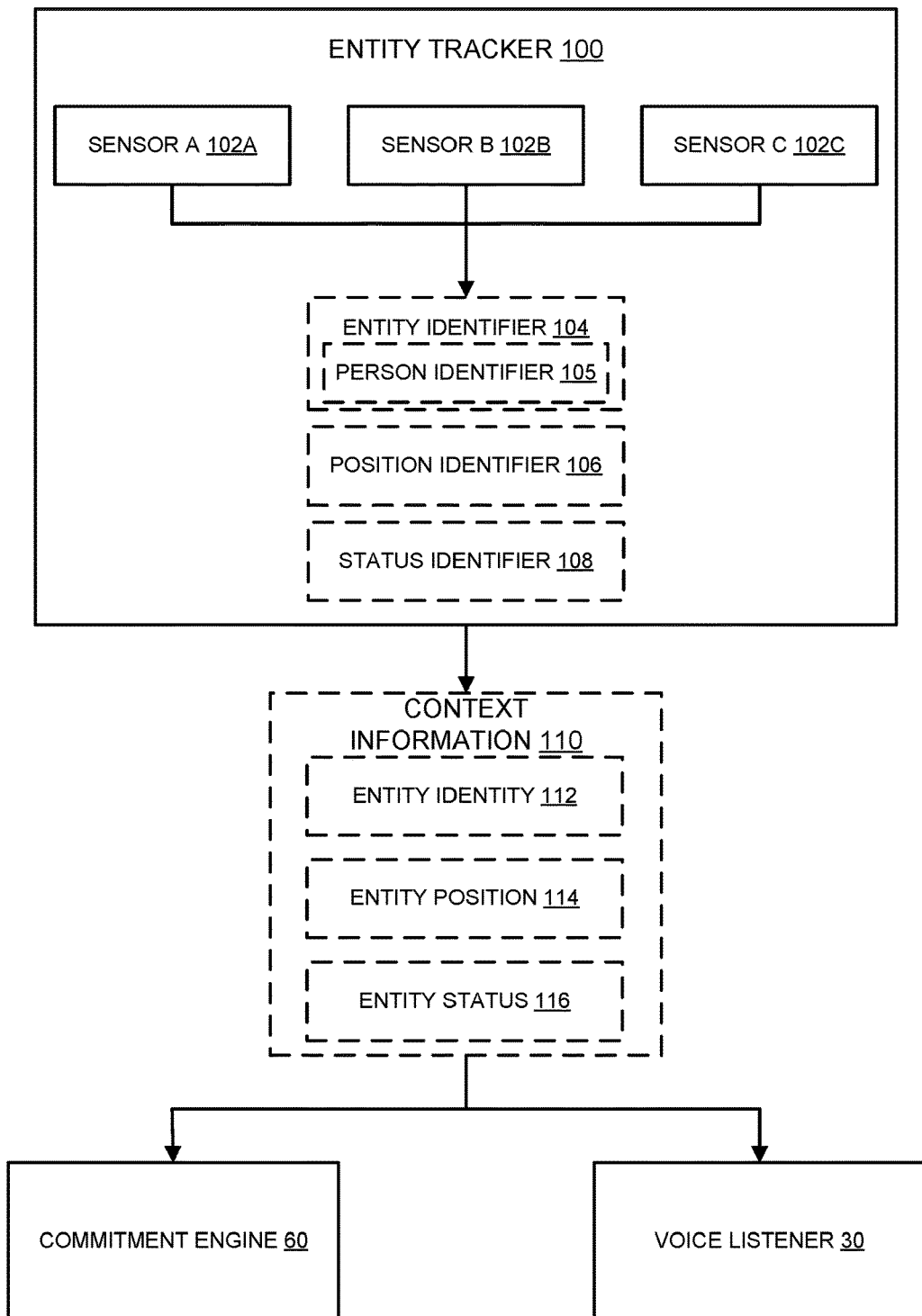
FIG. 7 schematically shows an entity tracker that may determine an identity, position, and/or current status of one or more entities according to examples of the present disclosure.

FIG. 7 schematically illustrates an example entity tracker 100 that may comprise a component of the intelligent assistant system 20. Entity tracker 100 may be used to determine an identity, position, and/or current status of one or more entities within range of one or more sensors. Entity tracker 100 may output such information to one or more other modules of intelligent assistant system 20, such as the commitment engine 60, voice listener 30, etc.

The word "entity" as used in the context of the entity tracker 100 may refer to people, animals, or other living things, as well as non-living objects. For example, the entity tracker may be configured to identify furniture, appliances, structures, landscape features, vehicles, and/or any other physical object, and determine the position/location and current status of such physical objects. In some cases, the entity tracker 100 may be configured to only identify people and not other living or non-living things. In such cases, the word "entity" may be synonymous with the word "person."

Entity tracker 100 receives sensor data from one or more sensors 102, such as sensor A 102A, sensor B 102B, and sensor C 102C, though it will be understood that an entity tracker may be used with any number and variety of suitable sensors. As examples, sensors usable with an entity tracker may include cameras (e.g., visible light cameras, UV cameras, IR cameras, depth cameras, thermal cameras), microphones, pressure sensors, thermometers, motion detectors, proximity sensors, accelerometers, global positioning satellite (GPS) receivers, magnetometers, radar systems, lidar systems, environmental monitoring devices (e.g., smoke detectors, carbon monoxide detectors), barometers, health monitoring devices (e.g., electrocardiographs, sphygmomanometers, electroencephalograms), automotive sensors (e.g., speedometers, odometers, tachometers, fuel sensors), and/or any other sensors or devices that collect and/or store information pertaining to the identity, position, and/or current status of one or more people or other entities. In some examples, the entity tracker 100 may occupy a common device housing with one or more of the plurality of sensors 102, and/or the entity tracker and its associated sensors may be distributed across multiple devices configured to communicate via one or more network communications interfaces (e.g., Wi-Fi adapters, Bluetooth interfaces). As one example with reference to FIG. 1, the entity tracker 100 may be implemented in computing device 10 along with image sensor 17.

As shown in the example of FIG. 7, entity tracker 100 may include an entity identifier 104, a person identifier 105, a position (location) identifier 106, and a status identifier 108. In some examples, the person identifier 105 may be a specialized component of the entity identifier 104 that is particularly optimized for recognizing people, as opposed to other creatures and non-living things. In other cases, the person identifier 105 may operate separately from the entity identifier 104, or the entity tracker 100 may not include a dedicated person identifier. As described in further detail below with reference to FIG. 25, the person identifier 105 may utilize output from a face detection algorithm to perform person identification.

Depending on the specific implementation, any or all of the functions associated with the entity identifier, person identifier, position identifier, and status identifier may be performed by the individual sensors 102A-102C. Though the present description generally describes the entity tracker 100 as receiving data from sensors, this does not require that the entity identifier 104, as well as other modules of the entity tracker, must be implemented on a single computing device that is separate and distinct from the plurality of sensors associated with the entity tracker. Rather, functions of the entity tracker 100 may be distributed amongst the plurality of sensors. For example, rather than sending raw sensor data to the entity tracker, individual sensors may be configured to attempt to identify entities that they detect, and report this identification to the entity tracker 100, and/or other modules of intelligent assistant system 20. In some cases, this identification may include a confidence value.

Each of the entity identifier 104, person identifier 105, position identifier 106, and status identifier 108 is configured to interpret and evaluate sensor data received from the plurality of sensors 102, and to output context information 110 based on the sensor data. Context information 110 may include the entity tracker's guesses/predictions as to an identity, position, and/or status of one or more detected entities based on received sensor data. As will be described in more detail below, each of the entity identifier 104, person identifier 105, position identifier 106, and status identifier 108 may output their predictions/identifications along with a confidence value.

The entity identifier 104 may output an entity identity 112 of a detected entity, and such entity identity may have any suitable degree of specificity. In other words, based on received sensor data, the entity tracker 100 may predict the identity of a given entity, and output such information as entity identity 112. For example, the entity identifier 104 may report that a particular entity is a piece of furniture, a dog, a human male, etc. Additionally, or alternatively, the entity identifier 104 may report that a particular entity is an oven with a particular model number; a pet dog with a specific name and breed; an owner or user of intelligent assistant system 20, with the owner/user having a particular name and profile; etc. In some examples, the degree of specificity with which the entity identifier 104 identifies/classifies detected entities may depend on one or more of user preferences and sensor limitations.

When applied to people, the entity tracker 100 may in some cases collect information about individuals whom it is unable to identify by name. For example, the entity identifier 104 may record images of a person's face, and associate these images with recorded audio of the person's voice. Should the person subsequently speak to or otherwise address the intelligent assistant system 20, the entity tracker 100 will then have at least some information regarding with whom the intelligent assistant system is interacting. In some examples, the intelligent assistant system 20 could also prompt the person to state their name, so as to more easily identify the person in the future.

In some examples, the intelligent assistant system 20 may utilize a person's identity to customize a user interface for the person. In one example, a user may be identified who has limited visual capabilities. In this example and based on this identification, a display of the intelligent assistant system 20 (or other device with which the user is interacting) may be modified to display larger text, or to provide a voice-only interface.

The position identifier 106 may be configured to output an entity position (i.e., location) 114 of a detected entity. In other words, the position identifier 106 may predict the current position of a given entity based on collected sensor data, and output such information as entity position 114. As described below with reference to FIG. 25, the position identifier 106 may utilize output from one or more tracking algorithms that process image data in different manners to persistently track an entity position as the position changes and/or as the status of the entity changes. As with the entity identity 112, the entity position 114 may have any suitable level of detail, and this level of detail may vary with user preferences and/or sensor limitations. For example, the position identifier 106 may report that a detected entity has a two-dimensional position defined on a plane such as a floor or wall. Additionally, or alternatively, the reported entity position 114 may comprise a three-dimensional position of a detected entity within a real world, three-dimensional environment. In some examples an entity position 114 may comprise a GPS position, a location within a mapping system, etc.

The reported entity position 114 for a detected entity may correspond to the entity's geometric center, a particular part of the entity that is classified as being important (e.g., the head of a human), a series of boundaries defining the borders of the entity in three-dimensional space, etc. The position identifier 106 may further calculate one or more additional parameters describing the position and/or orientation of a detected entity, such as a pitch, roll, and/or yaw parameter. In other words, the reported position of a detected entity may have any number of degrees-of-freedom, and may include any number of coordinates defining the position of the entity in an environment. In some examples, an entity position 114 of a detected entity may be reported even if the entity tracker 100 is unable to identify the entity, and/or determine the current status of the entity.

Status identifier 108 may be configured to output an entity status 116 of a detected entity. In other words, the entity tracker 100 may be configured to predict the current status of a given entity based on received sensor data, and output such information as entity status 116. "Entity status" can refer to virtually any measurable or classifiable property, activity, or behavior of a given entity. For example, when applied to a person, the entity status of the person can indicate a posture of the person (e.g., standing, sitting, laying down), a speed at which the person is walking/running, a current activity of the person (e.g., sleeping, watching TV, working, playing a game, swimming, talking on the phone), a current mood of the person (e.g., by evaluating the person's facial expression or tone of voice), biological/physiological parameters of the person (e.g., the person's heart rate, respiration rate, oxygen saturation, body temperature, neurological activity), whether the person has any current or upcoming calendar events/appointments, etc. "Entity status" can refer to additional/alternative properties or behaviors when applied to other creatures or non-living objects, such as a current temperature of an oven or kitchen sink, whether a device (e.g., television, lamp, microwave) is powered on, whether a door is open, etc.

In some examples, the status identifier 108 may use sensor data to calculate a variety of different biological/physiological parameters of a human. This may be done in a variety of suitable ways. For example, the entity tracker 100 may be configured to interface with an optical heart rate sensor, a pulse oximeter, a sphygmomanometer, electrocardiograph, etc. Additionally or alternatively, the status identifier 108 may be configured to interpret data from one or more cameras and/or other sensors in an environment, and process the data in order to calculate a human's heart rate, respiration rate, oxygen saturation, etc. For example, the status identifier 108 may be configured to utilize Eulerian magnification and/or similar techniques to amplify miniscule movements or changes captured by the cameras, thereby allowing the status identifier to visualize the flow of blood through a human's circulatory system and calculate associated physiological parameters. Such information can be used, for example, to determine when the person is asleep, working out, in distress, experiencing health problems, etc.

Upon determining one or more of the entity identity 112, entity position 114, and entity status 116, such information may be sent as context information 110 to any of a variety of external modules or devices, where it may be used in a variety of ways. For example, context information 110 may be used by commitment engine 60 to manage commitments and associated messages and notifications. In some examples and as described in more detail below, context information 110 may be used by commitment engine 60 to determine whether a particular message, notification, or commitment should be executed and/or presented to a user. Similarly, context information 110 may be utilized by voice listener 30 when interpreting human speech or activating functions in response to a keyword trigger.

As noted above, in some examples the entity tracker 100 may be implemented in a single computing device. In other examples, one or more functions of the entity tracker 100 may be distributed across multiple computing devices working cooperatively. For example, one or more of the entity identifier 104, person identifier 105, position identifier 106, and status identifier 108 may be implemented on different computing devices, while still collectively comprising an entity tracker configured to perform the functions described herein. As indicated above, any or all of the functions of the entity tracker may be performed by individual sensors 102. Further, in some examples entity tracker 100 may omit one or more of the entity identifier 104, person identifier 105, position identifier 106, and status identifier 108, and/or include one or more additional components not described herein, while still providing context information 110. Additional details regarding components and computing aspects that may be used to implement entity tracker 100 are described in more detail below with respect to FIG. 23.

Each of entity identity 112, entity position 114, and entity status 116 may take any suitable form. For example, each of the entity identity 112, position 114, and status 116 may take the form of a discrete data packet including a series of values and/or labels describing the information gathered by the entity tracker. Each of the entity identity 112, position 114, and status 116 may additionally include a confidence value defining a statistical likelihood that the information is accurate. For example, if the entity identifier 104 receives sensor data that strongly indicates that a particular entity is a human male named "John Smith," then entity identity 112 may include this information along with a corresponding relatively high confidence value, such as 90% confidence. If the sensor data is more ambiguous, then the confidence value included in entity identity 112 correspondingly may be relatively lower, such as 62%. In some examples, separate predictions may be assigned separate confidence values. For example, the entity identity 112 may indicate with 95% confidence that a particular entity is a human male, and indicate with a 70% confidence that the entity is John Smith.

As described in more detail below, such confidence values (or probabilities) may be utilized by a cost function in generating cost calculations for providing messages or other notifications to a user and/or performing action(s).

Figure 24:
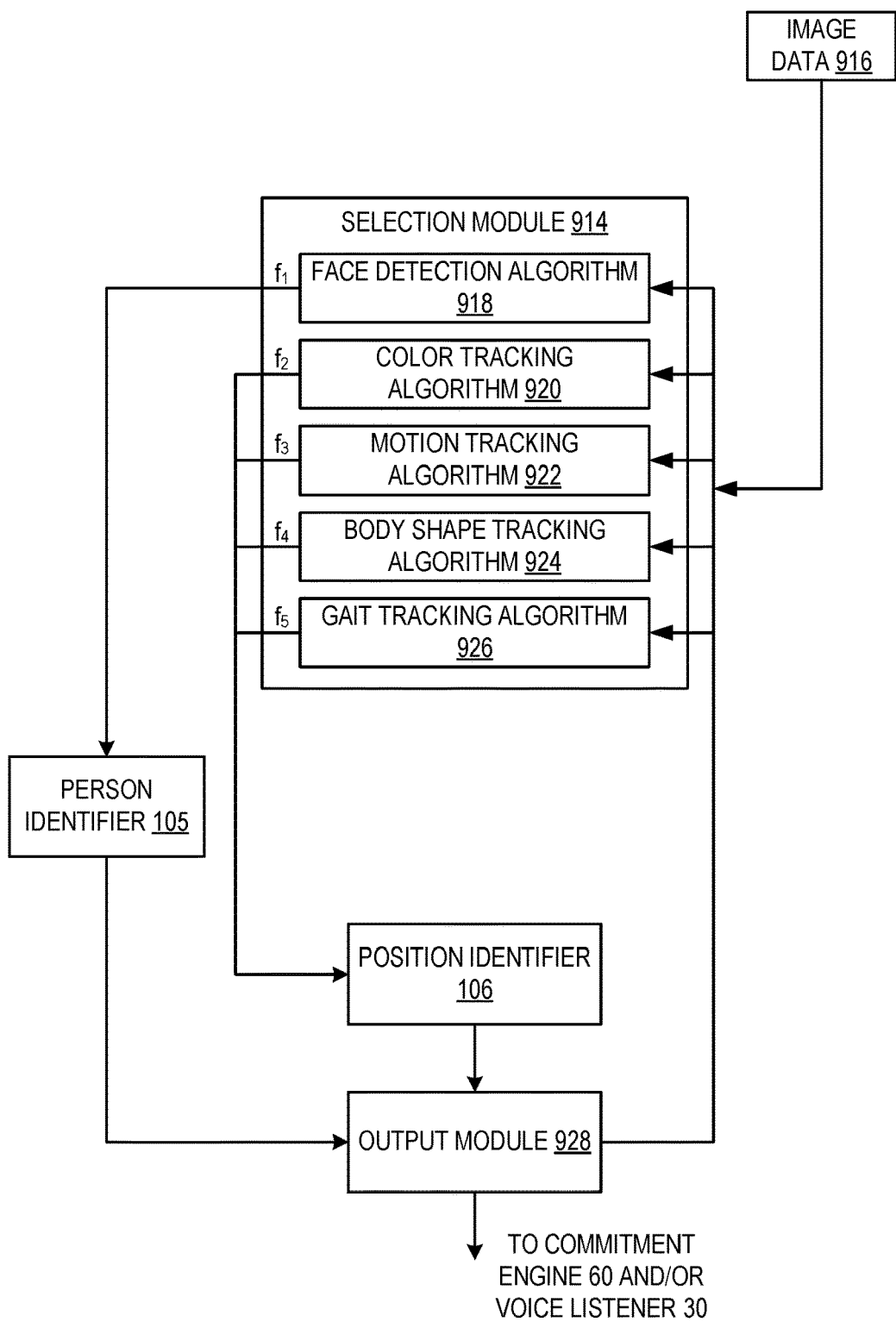
FIG. 24 schematically shows a portion of an entity tracker that may select from among different image processing algorithms.

In some implementations, the entity tracker 100 may employ different algorithms for identifying an entity and tracking the location of the entity, respectively. Moreover, the entity tracker 100 may select from among multiple algorithms to track the entity. To this end, FIG. 24 schematically illustrates an example implementation of a portion of an entity tracker 100 that comprises a selection module 914 configured to select from among multiple image processing algorithms.

In this example, the image processing algorithms are configured to receive image data 916 of an environment including a person. The image data 916 may include visible light image data (e.g., received from a visible light camera), infrared image data (e.g., received from an infrared camera), greyscale image data, depth data, images, video, two-dimensional image data, three-dimensional image data, and/or any other suitable type of image data. The distribution of the image data 916 to the various image processing algorithms may enable different insights into the image data and the person(s) captured therein to be obtained, as each image processing algorithm is configured to produce output having a corresponding datatype. As described in further detail below, this may increase the robustness of entity tracking and reduce its computational expense.

The selection module 914 may select a face detection algorithm 918 for detecting the face of the person captured in the image data 916. The face detection algorithm 918 is configured to produce a face detection output, which is fed to the person identifier 105, described above with reference to FIG. 2. The person identifier 105 may determine an identity of the person by comparing the face detection output to other face detection data and identifying a match. The face detection output may include a feature vector, for example, and may be produced using any suitable face detection techniques. In some examples, one or more portions of the selection module 914 may be implemented as part of the person identifier 105.

Face detection using face detection algorithm 918 may be triggered in various manners. Triggers may include but are not limited to a new appearance of a face in image data; a reappearance of a previously-imaged face in image data; and a trigger initiated by a person, such as a request to identify oneself or another person, a request for a computing device action, and/or a request for which identification of the requester is generally desired (e.g., to personalize a resulting action to the requester). In other examples, face detection may be desired at regular intervals that are not triggered by external influences—e.g., to maintain a persistent identification of a person in the presence of changes to the location and status of the person.

However, the computational expense associated with face detection may render its performance at frequent intervals undesirable and/or impracticable given the computing resources available to perform the face detection. Long processing times, finite computing resources (e.g., constrained by the mere availability of a single computing device), and the allocation of resources to tasks other than face detection may contribute to such undesirability and/or impracticability. Accordingly, algorithms that use less computational resources than the face detection algorithm 918 may be used to track a person at higher frequencies than those at which face detection is possible or desirable. Accordingly and in some examples, over a given interval of time the image data 916 may be processed with at least one tracking algorithm while the image data is not processed using the face detection algorithm 918.

To track the person captured in the image data 916, the selection module 914 may select from among a color tracking algorithm 920, a motion tracking algorithm 922, a body shape tracking algorithm 924, and a gait tracking algorithm 926. The color tracking algorithm 920 is configured to output a color histogram of image data indicating the magnitude, frequency, intensity, and/or other value of each of a desired number of color bins of the image data. Any number, range, and width may be selected for the color bins in a pre-determined manner or dynamically based on the image data 916. As one example, red, green, and blue color bins may be selected for RGB color image data. The image data for which the color histogram is produced may be a subset of the image data 916 that corresponds to the person captured therein. As such, the color histogram may primarily be a function of the colors exhibited by the person—such as the colors exhibited by his or her skin tone and clothes.

The motion tracking algorithm 922 is configured to output one or more motion vectors of image data. The motion vector(s) may include a magnitude and direction, and may indicate the motion associated with corresponding regions in two or more portions of temporally-offset image data. In implementations in which image data includes at least two different frames of image data that each capture a person, the motion tracking algorithm 922 may produce a motion vector indicating the motion of the person from the first frame to the second frame. As with the entity position 114 described above, a tail and/or head of a motion vector may correspond to any suitable part of a person, including but not limited to a person's geometric center, a classified part, etc. Further, a motion vector may be related to any suitable coordinate system, which in some examples may be associated with the environment occupied by an imaged person.

The body shape tracking algorithm 924 is configured to output a body model of a person captured in image data. The body model may include information regarding any suitable characteristic(s) of the person's body, including but not limited to a body contour, a body outline, a skeletal model, a body classification, limb/body part proportions, height, and/or wingspan.

The gait tracking algorithm 926 is configured to output gait analysis data regarding a person captured in image data. The gait analysis data may include information regarding any suitable characteristic(s) of the person's gait, including but not limited to joint angles, limb positions, two or three-dimensional video of gait, a skeletal model representing gait, and/or a three-dimensional mesh representing gait. Thus, in some examples the gait analysis data may be derived by tracking a person's gait over time—e.g., over a plurality of frames of image data.

The selection module 914 may select from among the tracking algorithms based on the available computing resources of the computing device(s) with which tracking is performed. Any type of computing resource may be considered in selecting tracking algorithms. For example, a tracking algorithm may be selected based on a battery life condition associated with a computing device. In this case, the computing device may be powered by a battery, and the algorithm may be selected such that a desired battery life is preserved after processing the image data 916 using the algorithm. As one particular example, the selection module 914 may select the tracking algorithm that consumes the least power when used to process image data if the remaining battery life is less than a predetermined threshold (e.g., 10%), and may forego selection of the other tracking algorithms. Further, the number of tracking algorithms available for selection may increase as the remaining battery life increases. For example, above a predetermined threshold (e.g., 30-50%), the battery life condition may be sufficient to enable selection of all tracking algorithms.

As another example, a tracking algorithm may be selected based on an allocation of resources of a logic processor to one or more tasks other than processing of image data. In this case, resources (e.g., time slices, cores, threads) of the logic processor may be allocated to tasks relating to an operating system, application, entity, etc., and the algorithm may be selected such that image processing with the algorithm does not consume more than the available share of logic processor resources (e.g., in order to prevent stalls and a degraded user experience).

The tracking outputs produced by the tracking algorithms 920-926 are fed to the position identifier 106, described above with reference to FIG. 7. In some examples, one or more portions of the selection module 914 may be implemented as part of the position identifier 106. The position identifier 106 may track the person imaged in the image data 916 based on one or more of the tracking outputs, and may provide a location of the person to an output module 928. The output module 928 also receives output from the person identifier 105, and may provide one or both of the identity and location of the person captured in the image data 916 to other modules and/or devices, such as the commitment engine 60 and/or the voice listener 30 described above.

As represented in FIG. 24, each tracking algorithm 920-926 produces a tracking output at a respective frequency ($f_2$, $f_3$, $f_4$, and $f_5$, respectively) that is higher than a frequency ($f_1$) at which the face detection algorithm 918 produces the face detection output. In addition to enabling the generation of tracking outputs at high frequencies, the tracking algorithms may mitigate drawbacks associated with the lower frequency of face detection output. For example, as the location of a person's body constrains the possible locations of his or her face, by tracking the location of a person's body via a tracking output, the location of the person's face may be approximately tracked while face detection is unavailable (e.g., due to insufficient visibility of the face and/or allocation to processing of other image data). Upon becoming available once more, face detection may be prioritized in the location constrained by the tracking output. Thus and as noted above, in some examples the image data 916 may be processed with at least one tracking algorithm while the image data is not processed using the face detection algorithm 918.

Further, as the colors, body shape, and/or gait exhibited by a person may be substantially unique to that person, one or more of the color, body shape, and gait tracking algorithms 920, 924, and 926 may help identify the person. In some scenarios, the person may move throughout an environment and/or orient herself in a manner that occludes her face between the time at which an initial face detection is performed and the time at which a subsequent face detection is attempted. Between these times, color, body shape, and/or gait analysis data unique to that person can be used to track changes in the person's body location. In this manner, the identity associated with the person may be maintained. Accordingly, by associating and updating a face detection output (and/or an associated identity) with a tracking output, the face detection output (and/or associated identity) can be output at the higher frequency associated with the tracking output at a high confidence level.

To enable face detection to be informed by person tracking data, and as illustrated in the example of FIG. 24, output from output module 928 may be supplied to one or more of the algorithms 918-926. In addition to person identity and/or location, the output from output module 928 may include the direct output from one or more of the algorithms (e.g., face detection output, color histogram, motion vector, body model, and gait tracking data). Algorithm feedback in this manner may enable other types of updates, including updates to a tracking algorithm by the face detection algorithm, and updates between two or more tracking algorithms, as described in further detail below with reference to FIG. 25.

Various modifications to the selection module 914 are contemplated. For example, one or more of the algorithms available to the selection module 914 may be omitted, and/or one or more other algorithms not shown in FIG. 24 may be used to identify and/or track entities. Further, the algorithms may produce outputs at any suitable frequencies, which may be a function of the available computing resources and operating conditions. As examples, the face detection algorithm 918 may produce face detection outputs at a frequency of 1 Hz, while one or more of the tracking algorithms 920-926 may produce tracking outputs at a frequency of 5, 6, 10, or 30 Hz.

Figure 25:
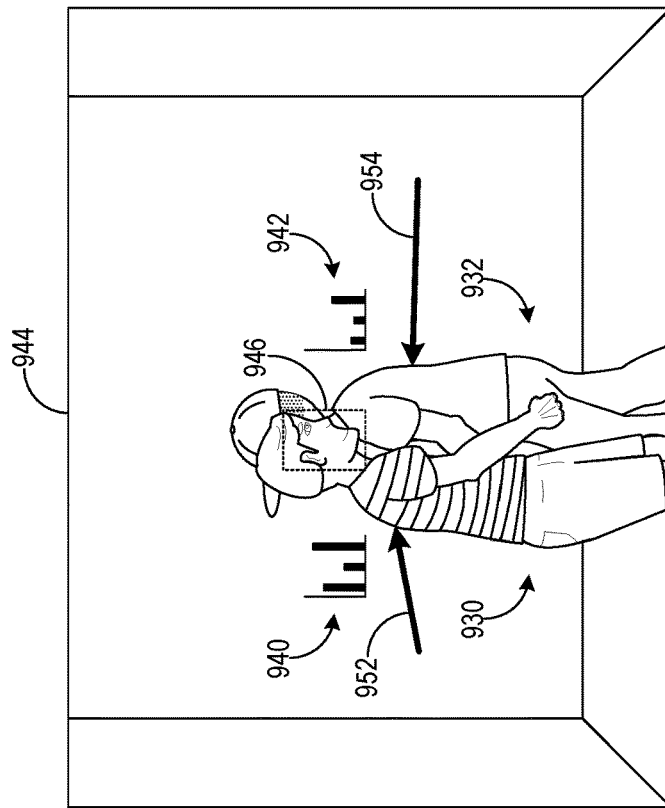
FIG. 25 illustrates an example scenario in which entity tracking is performed in the presence of entity motion and occlusion.
Figure 25:
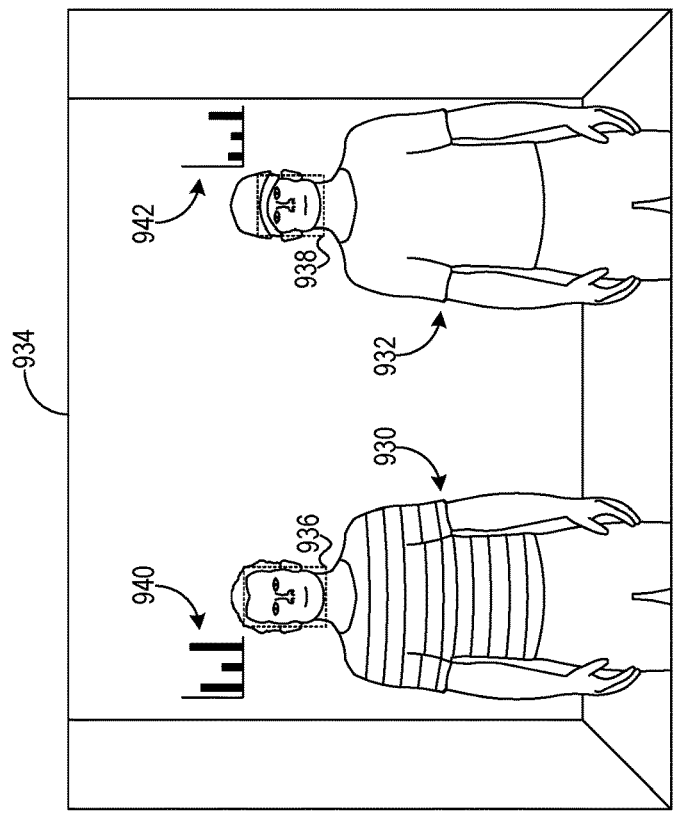

FIG. 25 depicts an example scenario in which entity tracking is performed in the presence of entity motion and occlusion. The example scenario illustrates how output from various image processing algorithms may be used to update one or more other image processing algorithms. To this end, reference is made to FIG. 24 and the image processing algorithms shown therein throughout the description of FIG. 25.

In this example initially two people—a first person 930 and a second person 932—are captured in a first frame 934 of image data (e.g., of the image data 916). The face detection algorithm 918 receives and performs face detection on the first frame 934, producing face detection outputs for the first and second people 930 and 932 in a region 936 and a region 938, respectively, where each person's face is detected in the frame. The selection module 914 then determines a less computationally intensive manner in which to track the first and second people 930 and 932 by selecting one or more of the tracking algorithms 920-926.

In this example, the color tracking algorithm 920 is selected and produces a color histogram 940 for the first person 930, and a color histogram 942 for the second person 932. Other tracking algorithms may go unselected due to a lack of available computing resources, for example. In other examples, the motion and/or gait tracking algorithms 922 and 926 may be selected, but may produce a null output indicative of the motion of each person 930 and 932 (e.g., relative to one or more prior frames) being below a predetermined threshold.

The face detection outputs produced in first frame 934 may inform one or more of the selected tracking algorithms. For example, the regions 936 and 938 may be provided as input to the color tracking algorithm 920, which may constrain or prioritize color histogram derivation in other regions of first frame 934 proximate to the first and second regions (as it is likely any imaged bodies are proximate to their corresponding facial regions).

FIG. 25 further shows a second frame 944 imaging the first and second people 930 and 932. The second frame 944 is captured after the first frame 934, and at a time at which both the first and second people 930 and 932 have undergone substantial motion relative to their positions in the first frame—both people have moved toward the center of the environment from its sides, with the first person partially occluding the second person. The face detection algorithm 918 receives and performs face detection on the second frame 944, producing a face detection output for the first person 930 in a region 946. However, the face detection algorithm 918 is unable to detect the face of the second person 932, as it is occluded by the first person 930.

Various tracking algorithms produce may track outputs in the second frame 944. The motion tracking algorithm 922 may produce a motion vector 952 for the first person 930, and a motion vector 954 for the second person 932. The motion vectors 952 and 954 may indicate the motion of the corresponding people relative to the first frame 934 and/or to other frames prior to the second frame 944. Further, the color histograms 940 and 942 produced in the first frame 934 continue to be associated with the first and second people 930 and 932, respectively, in the second frame 944. In other examples, the color tracking algorithm 920 may produce new color histograms in the second frame 944 for one or both of the first and second people 930 and 932. Other tracking outputs may be produced for the second frame 944, including but not limited to outputs from the body shape and/or gait tracking algorithms 924 and 926.

In the second frame 944, tracking output may be used to update a target region in which processing by the face detection algorithm 918 is prioritized. For example and regarding the first person 930, the color histogram 940 produced from the first frame 934 and/or the motion vector 952 produced from the second frame 944 may influence the target region where face detection is prioritized. For example, the color histogram 940 produced from the first frame 934 may be tracked in the second frame 944 to update the target region, such that the region 946 where the face of the first person 930 is ultimately found is in a region of the second frame where face detection is performed first. As another example, the head of the motion vector 952 produced from the second frame 944 may at least partially locate the target region where face detection is performed first. The target region may correspond to a location of the first person 930 tracked by such tracking output(s)—for example, the target region may be above or generally proximate to a location of the first person known or believed likely to correspond to the body of the first person.

In some examples, face detection output may be used to update a tracking algorithm. In one example, an association may be derived between the region 936, in which the face of the first person 930 is detected in the first frame 934, and the color histogram 940 produced by the color tracking algorithm 920 in the first frame. In the second frame 944, the color tracking algorithm 920 may be updated by associating the color histogram 940 with the region 946 in which the face of the first person 930 is detected in the second frame 944. In other examples, such as those in which a new color histogram is determined for the first person 930 in the second frame 944, the region 946 may instead may be used to constrain or prioritize color histogram derivation to an area proximate the region.

In some examples, a tracking output from one tracking algorithm may be provided as an input to another tracking algorithm. For example, the motion vector 952 may be used to constrain or prioritize a region in which a new color histogram is produced. As another example, the color histogram 940, when tracked from the location of the body of the first person 930 from the first frame 934 to the location of the body in the second frame 944, may be used by the motion tracking algorithm 922 to locate an endpoint of the motion vector 952.

FIG. 25 also illustrates how tracking algorithms may be used to persistently track and potentially maintain knowledge of an identity of a person. While the face of the second person 932 is occluded in the second frame 944, other parts of the person are sufficiently visible to enable determination of the motion vector 954 and update the association of the color histogram 942 with the tracked location of the second person. The color histogram 942 and/or motion vector 954 may be used to constrain or prioritize face detection in subsequent frames where the facial location of the second person 932 may be anticipated by referencing the histogram and/or vector. Further, by virtue of their potential uniqueness to the second person 932, the color histogram 942 and/or motion vector 954 may help maintain a previously-determined identity of the second person despite the occlusion of their face in the second frame 944. In this manner, drawbacks due to facial occlusion, and the computational expense and long processing times associated with face detection, can be mitigated by employing less computationally expensive tracking algorithms.

Figure 26:
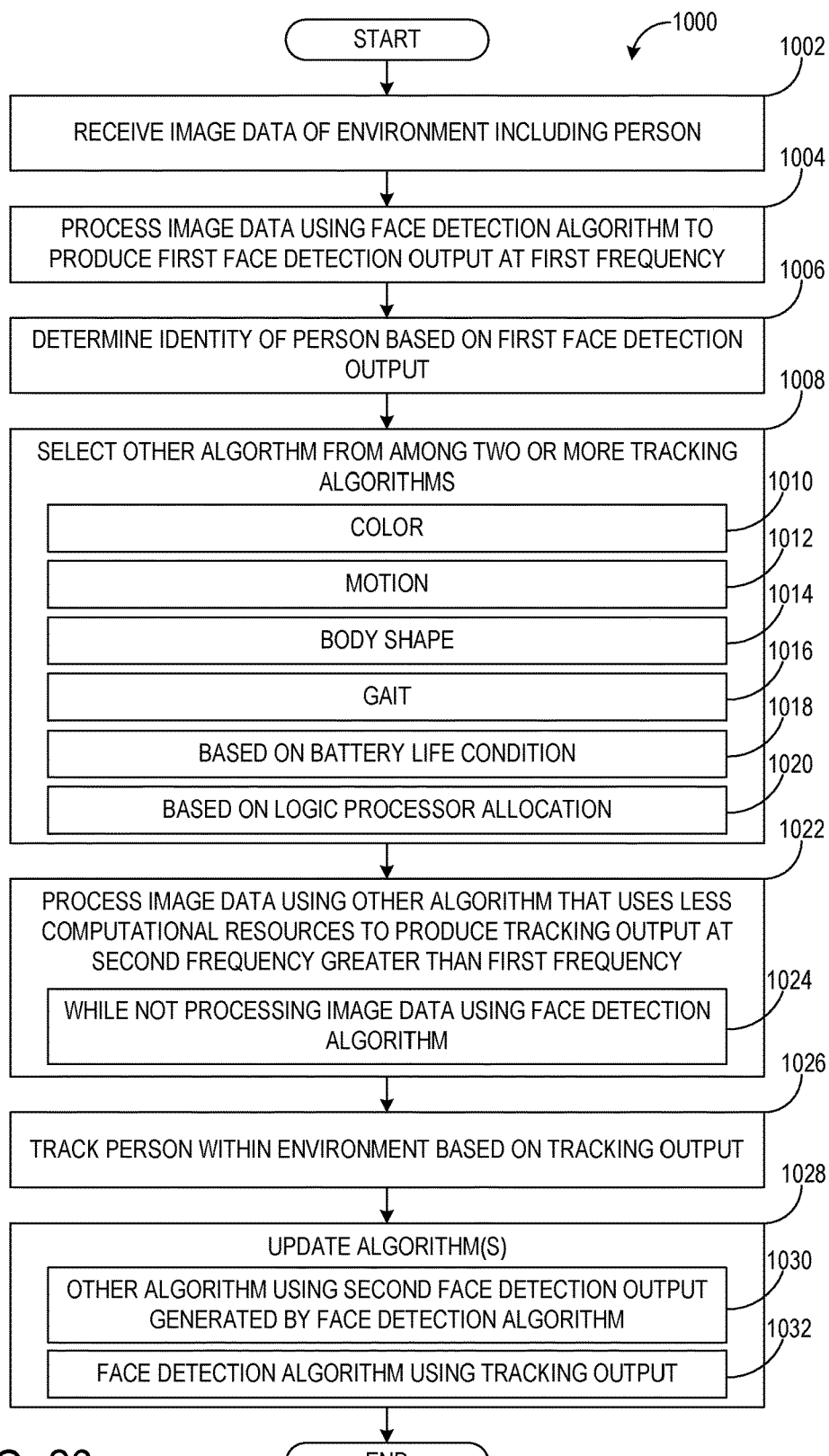
FIG. 26 shows a flow chart illustrating a method of entity tracking.

FIG. 26 shows a flow chart illustrating a method 1000 of entity tracking. The following description of the method 1000 is provided with reference to the software and hardware components described herein. It will be appreciated that method 1000 also may be performed in other contexts using other suitable hardware and software components.

At 1002, the method 1000 may include receiving image data of an environment including a person. The image data may include any suitable type of image data, including but not limited to greyscale, color, infrared, two-dimensional, and/or three-dimensional image data, and may be received from any suitable image sensor(s), including but not limited to a visible light camera and/or an infrared camera.

At 1004, the method 1000 may include processing the image data using a face detection algorithm to produce a first face detection output at a first frequency. For example, the face detection algorithm 918 may be used to process the image data. The face detection output may comprise any suitable output, such as a feature vector.

At 1006, the method 1000 may include determining an identity of the person based on the first face detection output. Person identifier 105 may determine the identity based on the first face detection output, for example. Determining the identity may include comparing the face detection output to other face detection outputs and identifying a match.

At 1008, the method 1000 may include selecting another algorithm from among two or more tracking algorithms. As indicated at 1010, 1012, 1014, and 1016, the tracking algorithm may be selected from among a color tracking algorithm, a motion tracking algorithm, a body shape tracking algorithm, and a gait tracking algorithm, respectively. For example, the selection module 914 may perform such selection. As indicated at 1018, the other algorithm may be selected based on the battery life condition of a computing device (e.g., a computing device executing the method 1000). As indicated at 1020, the other algorithm may be selected based on an allocation of resources of a logic processor of the computing device to one or more tasks other than processing of the image data. The other algorithm may use less computational resources of the computing device than the face detection algorithm.

At 1022, the method 1000 may include processing the image data using the other algorithm that uses less computational resources of the computing device than the face detection algorithm to produce a tracking output at a second frequency greater than the first frequency. Depending on the tracking algorithm(s) selected at 1008, the tracking output may comprise one or more of a color histogram, a motion vector, body shape analysis data, and gait analysis data. As indicated at 1024, the image data may be processed using the other algorithm (e.g., the at least one selected tracking algorithm) while not processing the image data using the face detection algorithm. For example, the available computational resources may be insufficient for concurrently processing the image data with the other algorithm and the face detection algorithm, and/or the face detection algorithm may be unavailable for processing the image data.

At 1026, the method 1000 may include tracking the person within the environment based on the tracking output from the other algorithm. Tracking the person may include tracking physical aspects of the person, such as a body and/or face location of the person. The position identifier 106 may track the person based on the tracking output, for example.

At 1028, the method 1000 may include updating one or more algorithms. As indicated at 1030, the other algorithm may be updated using a second face detection output generated by the face detection algorithm. For example, an association between a region of the image data in which a face of the person is detected and the tracking output may be updated. As indicated at 1032, the face detection algorithm may be updated using the tracking output. For example, a target region of the image data in which to prioritize the processing of the image data using the face detection algorithm may be updated, where the target region corresponds to a location of the person.

It will be appreciated that method 1000 is provided by way of example and is not meant to be limiting. Therefore, it is to be understood that method 1000 may include additional and/or alternative steps relative to those illustrated in FIG. 26. Further, it is to be understood that method 1000 may be performed in any suitable order. Further still, it is to be understood that one or more steps may be omitted from method 700 without departing from the scope of this disclosure.

In some implementations, the entity tracker 100 may be configured to combine or fuse data from multiple sensors in order to output more accurate predictions. As an example, a camera may locate a person in a particular room. Based on the camera data, the entity tracker 100 may identify the person with a confidence value of 70%. However, the entity tracker 100 may additionally receive recorded speech from a microphone. Based on the recorded speech alone, the entity tracker 100 may identify the person with a 60% confidence value. By combining the data from the camera with the data from the microphone, the entity tracker 100 may identify the person with a higher confidence value than would be possible using the data from either sensor alone. For example, the entity tracker may determine that the recorded speech received from the microphone corresponds to lip movements of the person visible to the camera when the speech was received, and thereby conclude with relatively high confidence, such as 92%, that the person visible to the camera is the person speaking. In this manner the entity tracker 100 may combine the confidence values of two or more predictions to identify a person with a combined, higher confidence value.

In some examples, data received from various sensors may be weighted differently depending upon a reliability of the sensor data. This can be especially relevant in situations where multiple sensors are outputting seemingly inconsistent data. In some examples, the reliability of a sensor's data may be based at least in part on the type of data generated by the sensor. For example, in some implementations a reliability of video data may be weighted higher than a reliability of audio data, as the presence of an entity on camera may be a better indicator of its identity, position, and/or status than recorded sounds that are presumed to originate from the entity. It will be appreciated that a reliability of sensor data is a different factor than a confidence value associated with a predicted accuracy of an instance of data. For example, several instances of video data may have different confidence values based on different contextual factors present at each instance. Each of these instances of video data, however, may be associated with a single reliability value for video data in general.

In one example, data from a camera may suggest that a particular person is in a kitchen with a 70% confidence value, such as via face recognition analysis. Data from a microphone may suggest with a 75% confidence value that the same person is in a nearby hallway, such as via voice recognition analysis. Even though the instance of microphone data carries a higher confidence value, the entity tracker 100 may output a prediction that the person is in the kitchen based on a higher reliability of the camera data as compared to a lower reliability of the microphone data. In this manner and in some examples, different reliability values for different sensor data may be used along with confidence values to reconcile conflicting sensor data and determine an identity, position, and/or status of an entity.

Additionally or alternatively, more weight may be given to sensors that have higher precision, more processing power or otherwise greater capabilities. For example, a professional-grade video camera may have a significantly improved lens, image sensor, and digital image processing capabilities as compared to a basic webcam found in a laptop. Accordingly, a higher weight/reliability value may be given to video data received from the professional-grade camera as compared to the webcam, as such data is likely to be more accurate.

Figure 8:
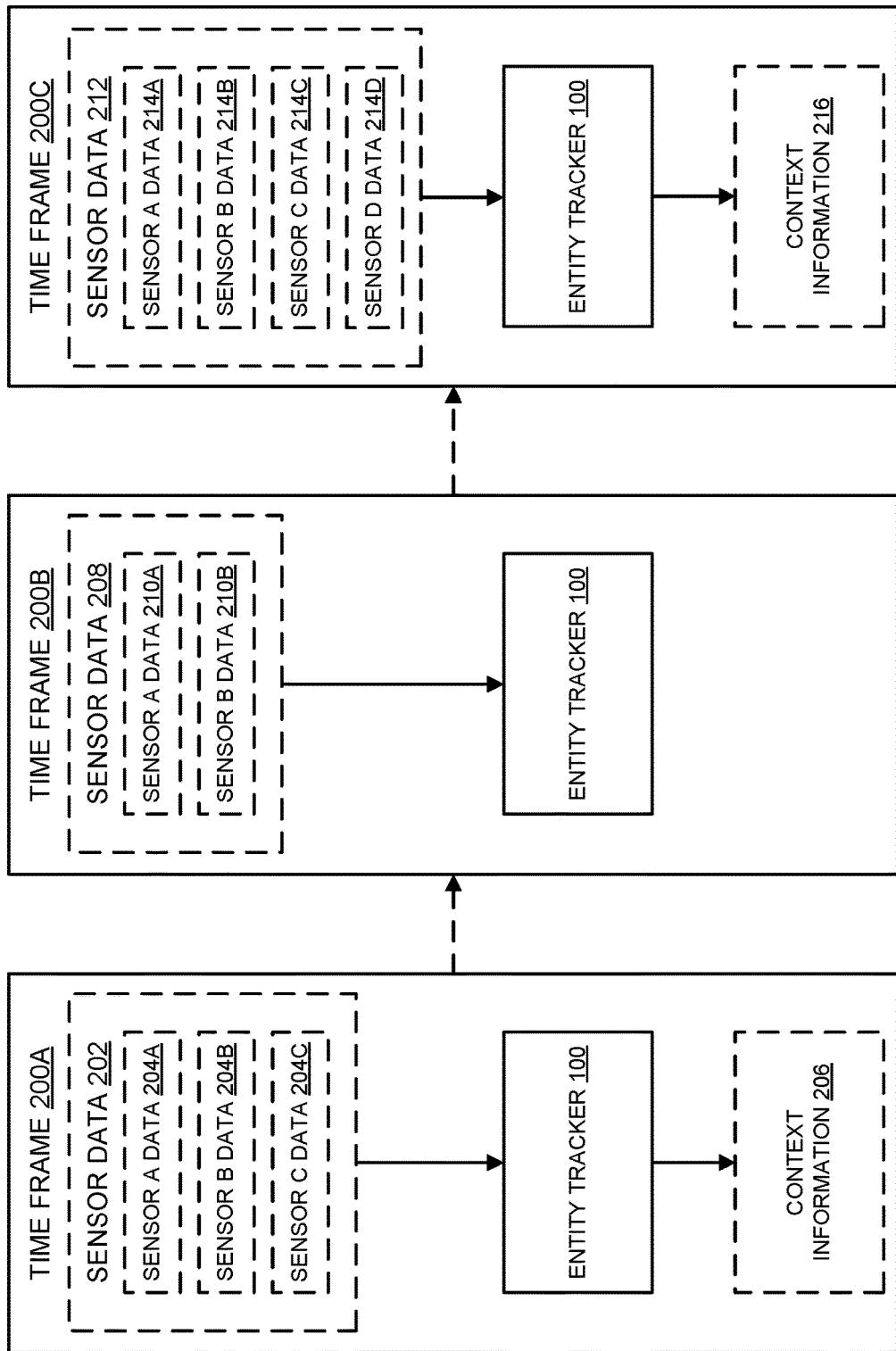
FIG. 8 schematically shows an entity tracker receiving and interpreting sensor data over multiple time frames according to examples of the present disclosure.

With reference now to FIG. 8, in some examples, individual sensors used with the entity tracker 100 may output data with a different frequency than other sensors used with the entity tracker. Similarly, sensors used with the entity tracker 100 may output data with a different frequency than the frequency with which the entity tracker evaluates the data and outputs context information. In the example of FIG. 8, entity tracker 100 may receive and interpret sensor data over multiple time frames 200A, 200B, and 200C. A single time frame may represent any suitable length of time, such as $\frac{1}{30}^{th}$ sec., $\frac{1}{60}^{th}$ sec., etc.

In this example, during time frame 200A entity tracker 100 receives a set of sensor data 202 including sensor A data 204A, sensor B data 204B, and sensor C data 204C. Such sensor data is interpreted by entity tracker 100 and transformed into context information 206, which may be used to determine an identity, position, and/or status of one or more detected entities as described above. During time frame 200B, entity tracker 100 receives sensor data 208, including sensor A data 210A and sensor B data 210B. Entity tracker 100 does not receive data from sensor C during time frame 200B, as sensor C outputs data at a different frequency than sensors A and B. Similarly, entity tracker 100 does not output context information during time frame 200B, as the entity tracker outputs context information at a different frequency than sensors A and B.

During time frame 200C, entity tracker 100 receives sensor data 212, including sensor A data 214A, sensor B data 214B, sensor C data 214C, and sensor D data 214D. Entity tracker 100 also outputs context information 216 during time frame 200C, which may be based on any or all of the sensor data received by the entity tracker since context information was last output in time frame 200A. In other words, context information 216 may be based at least in part on sensor data 208 as well as sensor data 212. In some examples, context information 216 may be based at least in part on sensor data 202 and sensor data 208, as well as sensor data 212.

As shown in FIG. 8, after the entity tracker 100 receives data from a particular sensor, multiple time frames may pass before the entity tracker receives more data from the same sensor. During these multiple time frames, entity tracker 100 may output context information. Similarly, the usefulness of data received from a particular sensor may vary from time frame to time frame. For example, at a first time frame the entity tracker 100 may receive audio data of a particular person speaking via a microphone, and accordingly identify an entity position 114 of the person with a relatively high confidence value. In subsequent time frames, the person may remain at the identified position, but also may have stopped speaking since the first time frame. In this case, the absence of useful data from the microphone may not be a reliable indicator of the absence of the person. Similar issues can arise with other types of sensors. For example, a camera may lose track of a person if he covers his face, or is occluded by an obstacle, such as another person or a moving object. In this case, though current camera data may not suggest the presence of the person, prior instances of camera data may suggest that the person is still located at the previously identified position. In general, while sensor data may reliably indicate the presence of an entity, such data may be less reliable in suggesting the absence of an entity.

Accordingly, the entity tracker 100 may utilize one or more confidence decay functions, which in different examples may be defined by the entity tracker and/or by the sensors themselves. A confidence decay function may be applied to sensor data to reduce the entity tracker's confidence in the data from a particular sensor as time passes since that sensor last positively detected an entity. As an example, after a sensor detects an entity at a particular location, the entity tracker 100 may report context information 110 indicating that the entity is at the location with relatively high confidence. If after one or more time frames the sensor no longer detects the entity at the location, and unless it subsequently gathers contradictory evidence, the entity tracker 100 still may report that the entity is at the location, though with a somewhat lower confidence. As time continues to pass since the sensor last detected the entity at the location, it becomes progressively less likely that the entity is still at the location. Accordingly, the entity tracker 100 may utilize the confidence decay function to progressively decrease the confidence value of its reported context information 110, eventually reaching 0% confidence if no additional sensors detect the entity.

In some cases, different confidence decay functions may be utilized with different sensors and sensor types. A selection of a particular decay function may depend at least in part on particular properties of a sensor. For example, confidence values associated with data from a video camera may decay more rapidly than confidence values associated with data from a microphone, as absence of an entity in a video frame is a more reliable indicator of the entity's absence than silence recorded by a microphone.

Figure 9:
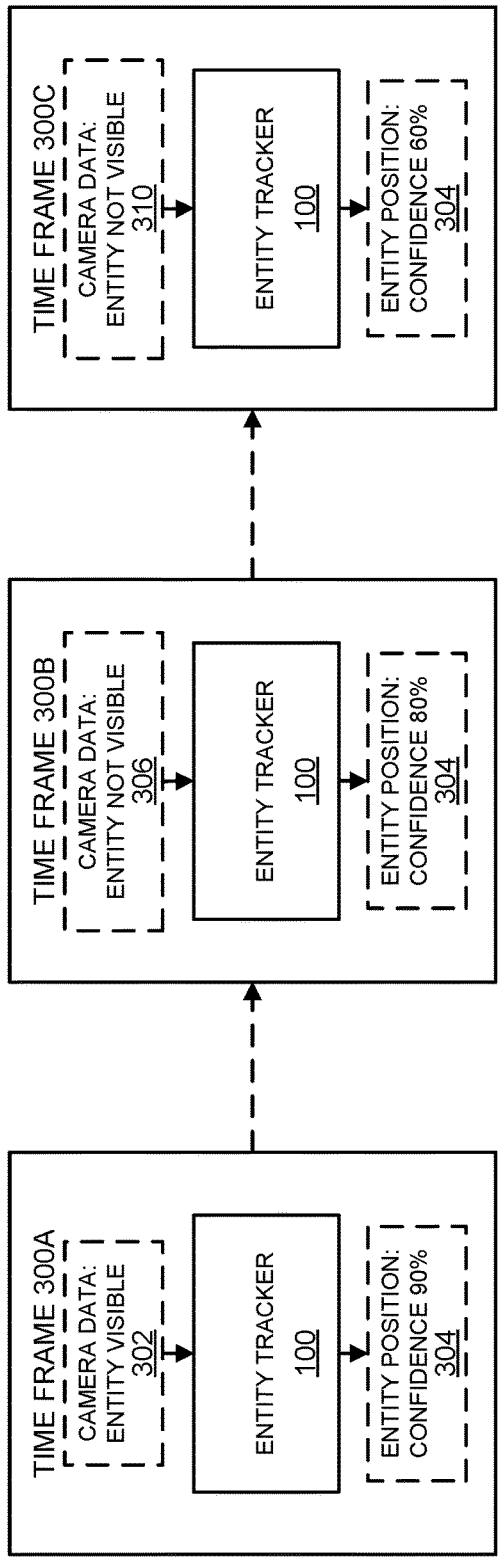
FIG. 9 schematically shows an example of sensor confidence decay over time via an entity tracker according to an example of the present disclosure.

One example of sensor confidence decay is schematically illustrated in FIG. 9, which shows entity tracker 100 receiving sensor data during three different time frames 300A, 300B, and 300C. During time frame 300A, entity tracker 100 receives camera data 302 in which an entity is visible in the frame. Based on this data, the entity tracker 100 reports the entity position 304 with a 90% confidence value. In time frame 300B, entity tracker 100 receives camera data 306 in which the entity is no longer visible in the frame. However, it is possible that the entity has not moved, and has merely become occluded, or otherwise undetectable to the camera. Accordingly, entity tracker 100 reports the same entity position 304, but with a lower confidence value of 80%.

Finally, in time frame 300C entity tracker 100 receives camera data 310 indicating that the entity is still not visible in the frame. As time has passed, it has grown less likely that the entity is still in the same position. Accordingly, the entity tracker 100 reports the same entity position 304 with a still lower confidence value of 60%.

In some examples, variable reliability of sensor data may be at least partially addressed by making use of data filtering techniques. In some examples, a Kalman filter may be utilized to filter sensor data. A Kalman filter is a mathematical function that may combine multiple uncertain measurements and output a prediction with more confidence than would be possible using any individual measurement. Each measurement input to the Kalman filter is given a weight based on the measurement's perceived reliability. Kalman filters operate in a two-step process, including a prediction step and an update step. During the prediction step, the filter outputs a prediction based on recent weighted measurements. During the update step, the filter compares its prediction to an actual observed value or state, and dynamically adjusts the weighting applied to each measurement so as to output more accurate predictions.

In some examples, entity tracker 100 may comprise a Kalman filter that combines data from a variety of sensors to compensate for lower sensor reliability, such as when sensor confidence values have decayed over time since the last positive detection. In some examples, entity tracker 100 may apply a Kalman filter to sensor data when one or more sensor confidence values are below a predetermined threshold. In an example scenario, image data from a camera may be analyzed using face detection techniques to reliably detect a person in a particular room. In response, the entity tracker 100 may report with high confidence that the person is located in the room.

In subsequent time frames, the camera may no longer be able to capture and/or positively recognize the person's face in the room. For example, the person's face may become occluded, or the camera may transmit data with a much lower frequency than the entity tracker 100 outputs context information 110. If the entity tracker 100 relied exclusively on data from the camera, then the confidence value of its reported position of the person would gradually decrease until the next positive detection. However and in some examples, data from the camera may be supplemented with data from other sensors. For example, during the subsequent time frames a microphone may report that it hears the person's voice in the room, or another sensor may report that it can detect the presence of the person's mobile device in the room. In such cases, this data may be assigned weights by the Kalman filter, and may be used to predict the person's current location with more confidence than would be possible if only the camera data were used.

In some cases, detection of people and/or other entities in an environment can become more complicated when sensor data is contaminated by background information. Such background information may compromise the confidence with which the entity tracker 100 reports entity identity 112, position 114, and/or status 116. For example, the intelligent assistant system 20 may need to determine the identity of a person who is speaking in order to appropriately respond to a query or command. Such a determination can be difficult when multiple people are speaking at the same time, a television is playing, loud machinery is operating, etc.

Accordingly, the entity tracker 100 may use a variety of audio processing techniques to more confidently identify a particular active participant who is engaged in a conversation with other people and/or with the intelligent assistant system 20. As an example, the entity tracker 100 may implement a voice activity detection (VAD) engine that may distinguish human voices from environmental noise, and identify the presence or absence of human speech.

General-purpose VAD engines may be used for the purpose of classifying a particular segment of audio as including either speech or non-speech, with a corresponding confidence value. An entity tracker 100 also may utilize a speaker recognition engine to match a particular audio segment with a particular person. As more speech is received, the speaker recognition engine may be progressively tailored to classify the audio as including speech from a particular conversation participant, or not including speech from the particular conversation participant. In this manner, the entity tracker 100 may recognize speech from one or more particular persons/conversation participants.

Training of a speaker recognition engine may occur any time the entity tracker 100 has confidently identified a particular person and recorded audio that can be confidently attributed to that person. For example, using camera data, the entity tracker 100 may identify a particular person and determine that the person's lips are moving. The entity tracker 100 may simultaneously receive audio from a microphone that can be safely assumed to include speech from the identified person. Accordingly, the received audio can be used to retrain the speaker recognition engine to more specifically recognize the identified person's voice.

In some cases, such retraining may occur only when the person has been identified with a high confidence value (e.g., via accurate facial recognition or any other method), such as a confidence value exceeding a predetermined threshold, and when the entity tracker 100 has received an audio recording of the person's voice having high volume/amplitude and a high signal-to-noise ratio (S/N). Using this technique, the entity tracker 100 may accumulate a variety of person-specific voice models, allowing the entity tracker to more consistently identify speech from particular people and ignore background noise.

Figure 10:
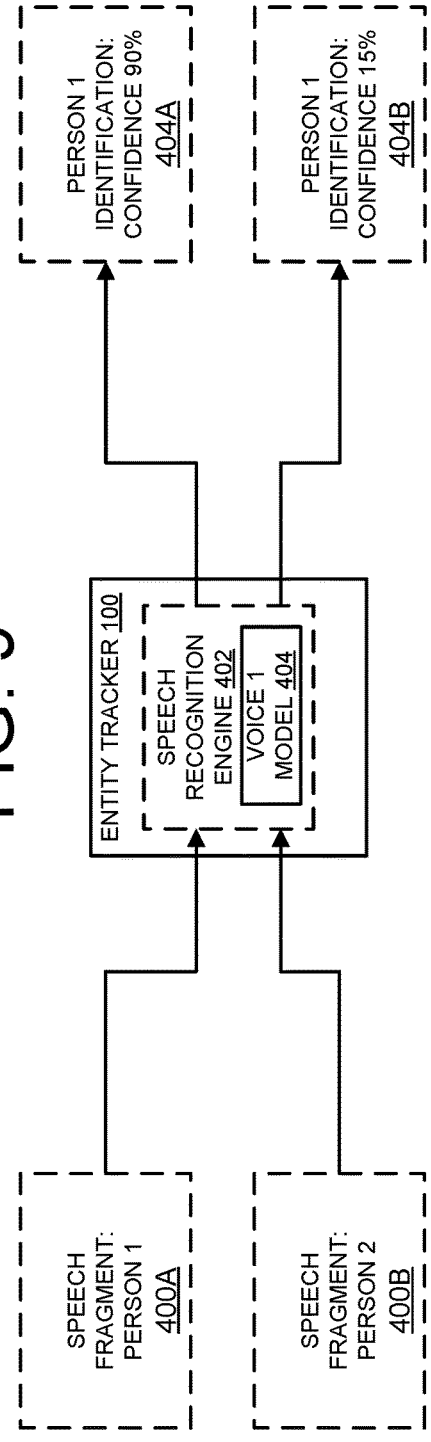
FIG. 10 schematically shows an example of using a trained voice recognition engine to recognize a person's speech according to examples of the present disclosure.

With reference now to FIG. 10, an example of using a trained speech recognition engine to recognize speech from a particular person is schematically illustrated. In this example, entity tracker 100 receives two speech fragments 400A and 400B. Speech fragment 400A includes recorded speech of a person 1, and speech fragment 400B includes recorded speech of a person 2. Entity tracker 100 includes a speech recognition engine 402 that has been specifically trained to recognize speech from person 1 using a voice 1 model 404, as described above. Voice 1 model 404 may be applied to each of speech fragment 400A and speech fragment 400B as they are received by the entity tracker 100.

Upon processing the speech fragments, the entity tracker 100 outputs a prediction of the likelihood that each speech fragment corresponds to person 1. As shown, for speech fragment 400A, the entity tracker outputs a person 1 identification 404A with a 90% confidence value, indicating that the speech fragment likely includes speech from person 1. For speech fragment 400B, the entity tracker outputs a person 1 identification 404B with a 15% confidence value, indicating that speech fragment 400B likely does not include speech from person 1.

In some examples, an entity tracker 100 may be configured to identify background noise present in an environment, and use audio processing techniques to subtract such background noise from received audio data. For example, a particular device in a person's home may be playing background audio, such as music or television/movie dialogue. Various microphone-equipped devices in the person's home may record such audio. Where such microphone-equipped devices include the intelligent assistant system 20 and/or provide audio data to the entity tracker 100, such background audio may compromise the ability of the system to identify, interpret and/or respond to human questions or commands.

Accordingly and in some examples, the device playing the background audio and/or another microphone-equipped device recording the background audio may send the captured audio signal to the entity tracker 100. In this manner, the entity tracker 100 may subtract the background audio from the audio signal received from the microphone-equipped devices. In some examples, the subtraction of the background audio signal from the recorded audio data may be performed by the device(s) that capture the audio data, or by associated audio-processing components, prior to sending the audio data to the entity tracker 100.

Additionally or alternatively, devices and/or the entity tracker 100 may be trained to recognize particular sources of background noise (e.g., from an air vent or refrigerator), and automatically ignore waveforms corresponding to such noise in recorded audio. In some examples, an entity tracker 100 may include one or more audio-recognition models trained specifically to recognize background noise. For example, audio from various noise databases may be run through unsupervised learning algorithms in order to more consistently recognize such noise. By allowing the entity tracker 100 to recognize irrelevant background noise, the ability of the entity tracker to recognize relevant human speech and other sounds may be improved.

Figure 11:
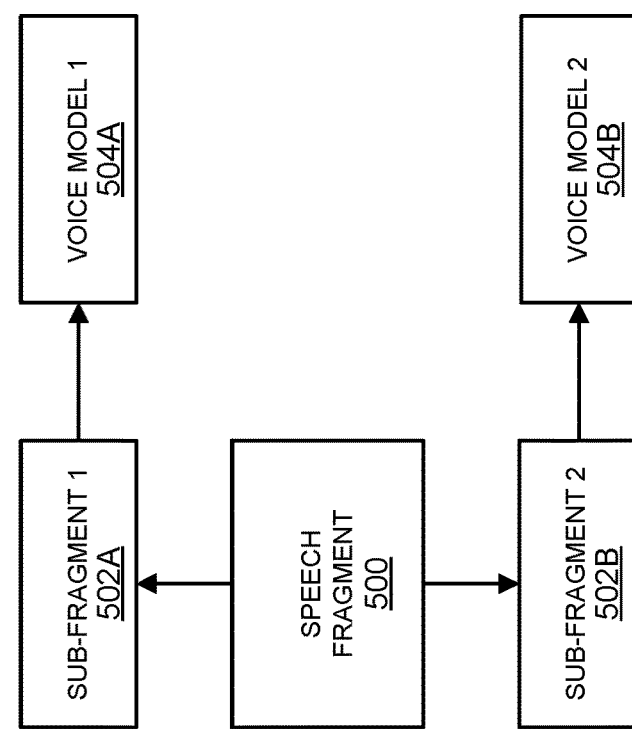
FIG. 11 schematically shows an example of using sub-fragments of audio data to train voice models according to examples of the present disclosure.

With reference now to FIG. 11, in some cases the entity tracker 100 may determine that a change has occurred in the active participant (i.e., the person currently speaking) in a conversation between two or more people. The entity tracker 100 also may determine at what point in time such a change occurred. This may be done in a variety of ways. In one example, a segment of recorded audio containing a speech fragment may be time-divided into two or more subframes, with each subframe containing a different sub-fragment of the recorded speech fragment. In the example of FIG. 11, speech fragment 500 may be time-divided into two or more sub-fragments, such as sub-fragment 1 502A and sub-fragment 2 502B. Each sub-fragment of speech may be used to train a separate voice model, such that the trained voice model may be used to specifically recognize speech from whichever person was speaking during that subframe. In FIG. 11, sub-fragment 502A is used to train voice model 1 504A, while sub-fragment 502B is used to train voice model 2 504B.

Figure 12:
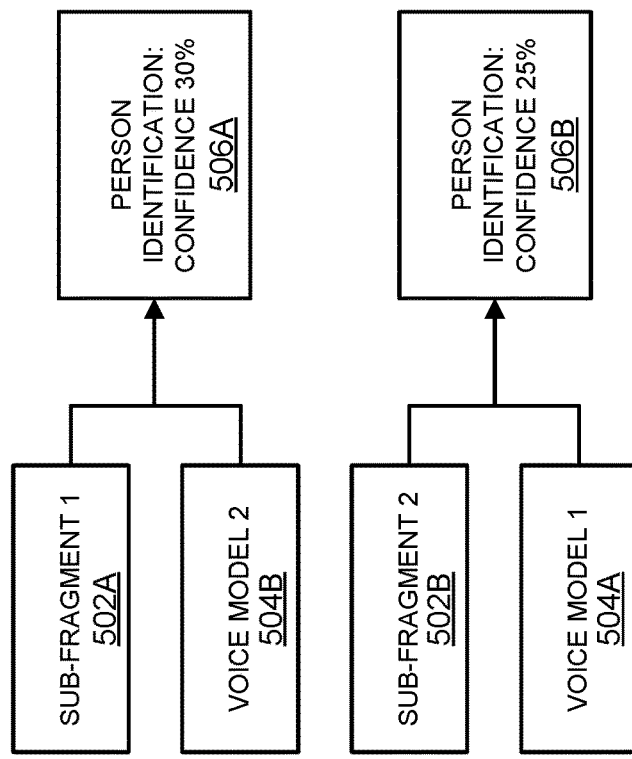
FIG. 12 schematically shows an example of cross-evaluating sub-fragments of audio data to determine whether the active speaker has changed according to examples of the present disclosure.

Once the sub-fragments have been used to train voice models, the sub-fragments may be cross-evaluated with different voice models. This is schematically shown in FIG. 12, in which voice model 2 504B, which was trained using sub-fragment 2 502B, is applied to sub-fragment 1 502A. Similarly, voice model 1 504A, which was trained using sub-fragment 1 502A, is applied to sub-fragment 2 502B.

During cross-evaluation, a prediction with a high confidence value will be generated if the person speaking during the tested sub-fragment is the same as the person speaking during the sub-fragment with which the voice model was trained. Accordingly, if both voice models result in predictions of the speaker identity with relatively high confidence values, then it is likely that the same person was speaking during both sub-fragments, and the active participant in the conversation did not change during the speech fragment. If both voice models result in predictions of the speaker identity with relatively low confidence, then it is likely that the active conversation participant changed at some point during the speech fragment. This possibility is illustrated in FIG. 12, in which voice model 2 504B outputs person identification 506A with a confidence value of 30%, and voice model 1 504A outputs person identification 506B with a confidence value of 25%. As both voice models have relatively low confidence in their predictions, it is likely that different people were speaking in each of sub-fragment 502A and sub-fragment 502B. It follows that it is likely that the active conversation participant changed at some point between sub-fragment 1 502A and sub-fragment 2 502B.

In some examples, and depending on the sensors and processing methods used by the entity tracker 100, tracking and identification of entities in an environment can be time-consuming and resource-intensive. Accordingly, the entity tracker 100 may use a variety of techniques to selectively choose when resource-intensive processing should be utilized. In this manner, the efficiency of the entity tracker 100 may be improved without compromising its corresponding functionality.

As an example, a variety of image processing techniques may be used to account for variable lighting conditions in an environment. In some examples, and depending on the brightness/darkness levels in a room, an entity tracker 100 can perform contrast adjustment and/or other image processing techniques in order to more clearly track and identify entities in the room. Such techniques, however, may require significant processing and computer resources. Accordingly and to conserve such resources, additional context information 110 may be evaluated to determine whether to utilize such techniques.

For example, where a room is dark and context information 110 with high confidence values indicates the room is empty, the entity tracker 100 may forego computationally-intensive image processing techniques in favor of conserving resources. In another example, where another sensor in the room detects that a person is likely present (e.g., a microphone records the person's voice), the entity tracker 100 may authorize the use of computationally-intensive image processing in an attempt to obtain an image that can be used to identify the person's face. In another example, an entity tracker 100 may reduce the sampling frequency of any sensors monitoring an environment in which no entities of interest are currently present. Thereafter, the entity tracker 100 may increase the sampling frequency of one or more sensors as needed, such as when the presence of an entity of interest is indicated with a confidence value exceeding a predetermined threshold.

Another process which can require significant computer resources is facial recognition using high-resolution images. In some examples, upon establishing a positive identification of a person using facial-recognition techniques, the entity tracker 100 may switch to less resource-intensive identification methods in order to continue tracking the person. As an example, upon detecting that a new person has entered a room, the entity tracker 100 may capture a high-resolution image of the person's face. The entity tracker 100 may utilize this image to perform relatively resource-intensive facial recognition in order to definitively identify the person.

After initial identification of the person, the entity tracker 100 may use less resource-intensive techniques in order to continue tracking the person while conserving computing resources. For example, the entity tracker 100 may use lower-resolution cameras to track the person based on the general shape of their body, their gait (e.g., by evaluating angles formed between different joints as the person walks), their clothing (e.g., tracking patches of color known to correspond to the person's clothing), etc. In some examples, and to periodically confirm its initial identification of the person is still accurate, the entity tracker 100 may perform facial recognition intermittently after the initial identification. In general and depending on the particular context, the entity tracker 100 may use any of a variety of identification techniques in order to intelligently manage both conservation of computing resources and identification and tracking of entities.

As noted above, the commitment engine 60 stores commitments received from the intent handler 50. Also as described above, the commitment engine 60 may utilize one or more cost functions to determine one or more costs associated with executing or not executing a commitment and, in some examples, with outputting or not outputting a message to the user. As described in more detail below, in some examples one or more messages may be added to a message queue.

Figure 13:
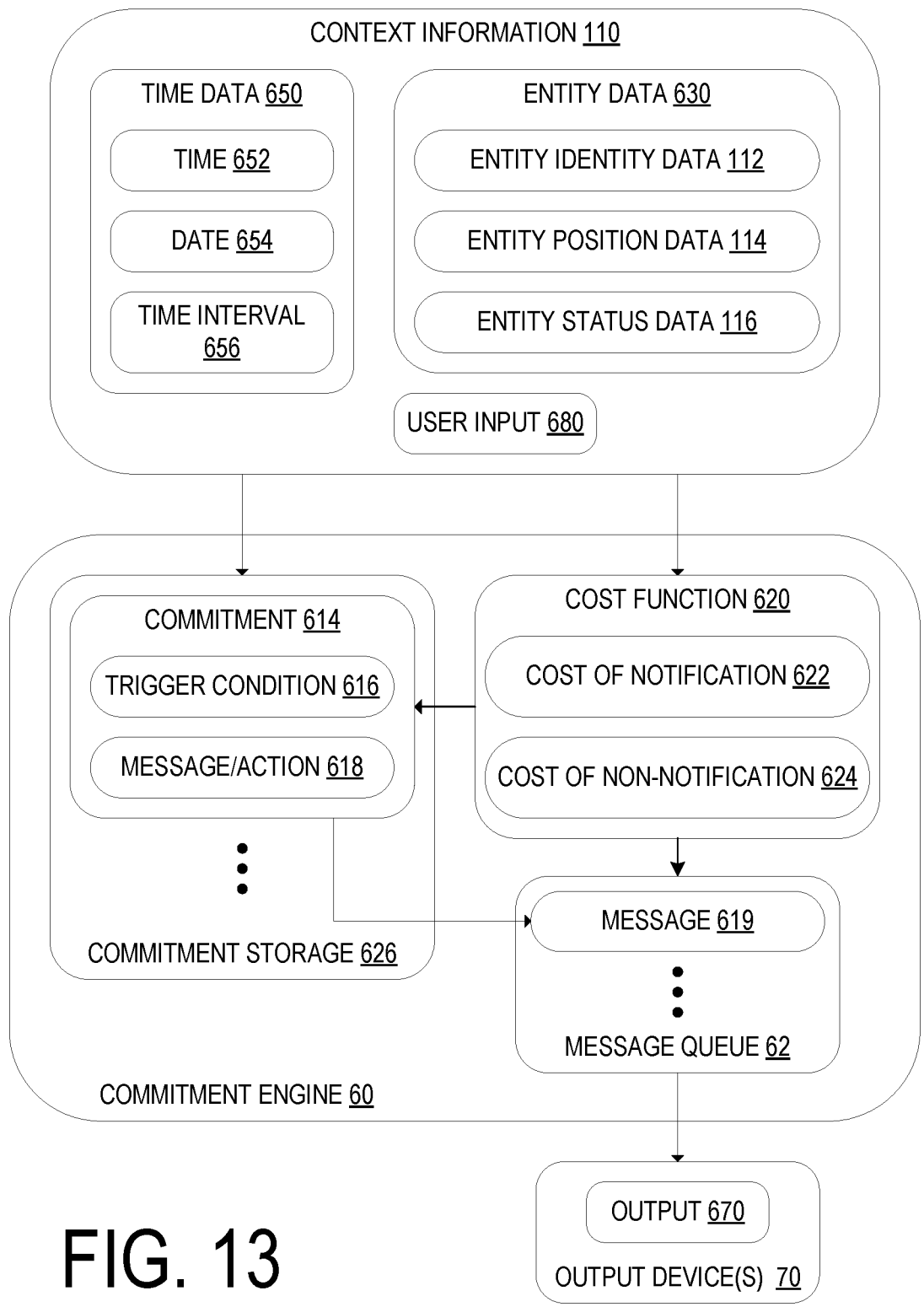
FIG. 13 shows a schematic illustration of a cost function according to examples of the present disclosure.

With reference now to FIG. 13, a schematic illustration of an example cost function 620 usable with commitment engine 60 is provided. The commitment engine 60 includes commitment storage 626 configured to store one or more commitments 614. The commitment 614 shown in FIG. 13 includes a trigger condition 616 and a message/action 618. In some examples, a commitment may comprise a set of 0 or more triggers and a set of 1 or more messages/actions (such as convey a message to a user, turn on the lights, play music, etc.). In some examples, the message/action 618 may comprise conveying a message 619 stored in a message queue 62 as output 670 via one or more output devices 70. In some examples, the message/action 618 may comprise executing one or more additional instructions that may include interfacing with one or more other devices or programs.

The commitment engine 60 is configured to receive context information 110 via entity tracker 100 and/or directly from one or more sensors 22. In various examples, the context information 110 may or may not satisfy a trigger condition, such as trigger condition 616. The context information 110 may include entity data 630 from the entity tracker 100. The context information 110 may further include time data 650 and/or a user input 680. The entity data 630, time data 650, and user input 680 are described in greater detail below.

When the commitment engine 60 receives context information 110 that satisfies the trigger condition 616 of the commitment 614, the commitment engine 60 may apply a cost function 620 to the message/action 618. Where the message/action 618 comprises a message, the cost function 620 is configured to determine whether to output the message associated with the commitment 614 to one or more users. Similarly, where the message/action 618 comprises an action, the cost function 620 is configured to determine whether to perform the action based at least in part on the context information 110. When the cost function 620 determines that the commitment 614 is of high enough importance, the commitment engine 60 may output the message and/or perform the action of message/action 618 as an output 670. The output 670 may be conveyed to one or more output devices 70. For example, the output 670 may comprise a verbal message that is broadcast by a speaker of a user's smartphone and/or one or more other speakers in the user's environment, such as a standalone speaker device, a television speaker, etc. In some examples, the output 670 may comprise controlling one or more other devices, such as turning on lights, playing music via a media program, etc.

The cost function 620 may determine whether to output a message 619 by calculating a cost of notification 622 and a cost of non-notification 624. If the cost of non-notification 624 is determined to be higher than the cost of notification 622, the commitment engine 60 may output the message 619. In some examples, the cost of notification 622 and the cost of non-notification 624 may be determined at least in part using one or more machine learning algorithms.

In some examples, the cost function 620 may determine the cost of notification 622 and the cost of non-notification 624 based at least in part on entity data 630 received from the entity tracker 100 and included in the context information 110. As explained above, the entity data 630 may include entity identity data 112, entity position data 114, and entity status data 116. The entity identity data 112, entity position data 114, and entity status data 116 may each include at least one list of users, locations, and activities respectively. Each user, location, and activity included in the entity identity data 112, entity position data 114, and entity status data 116 may have an associated estimate of a probability that that user, location, or activity was correctly identified. Such probability estimates may be utilized by the cost function 620 in determining corresponding costs of notification 622 and costs of non-notification 624. In some examples, the context information 110 may include entity identity data 112, entity position data 114, and entity status data 116 for one or more users or other entities detected simultaneously.

The commitment engine 60 also may be configured to receive time data 650. The time data 650 may include a time 652 and/or date 654. The time data 650 also may include at least one time interval 656 elapsed since a computing device performed some task. For example, the time data 650 may include at least one time interval 656 elapsed since a computing device produced a particular output or received a particular input. For example, a user may set a time interval 656 on an oven timer while baking bread, and the commitment engine 60 may receive context information 110 that satisfies the trigger condition 616 when the time interval 656 elapses and the oven timer buzzes. In response, the cost function 620 may be applied to a related commitment 614 to determine whether to output a message 619 that the bread should be removed from the oven, and/or perform an action to turn off the oven.

As another example, the time data 650 may include data indicating when a computing device most recently produced an output 670 notifying a user that the user should do laundry. The message queue 62 may store a related message 619 reminding the user to do his laundry. As the amount of time increases since the message was last given, as indicated by the time data 650, the cost function 620 may gradually increase the cost of non-notification 624. When the laundry notice is given, the cost function 620 may decrease the cost of non-notification 624 of the message 619. In some examples, the cost function 620 may determine the cost of notification 622 and the cost of non-notification 624 based at least in part on the time data 650.

The cost function 620 may determine the cost of notification 622 and the cost of non-notification 624 based at least in part on one or more user inputs 680. For example, a user may provide a user input 680 that increases the cost of non-notification 624 for a notification the user considers particularly important. The user may, in one example, provide a user input 680 to increase the cost of non-notification 624 for a job interview compared to a default cost of non-notification 624 for a lunch meeting with a friend.

The commitment engine 60 may determine an output type for the output 670. The determination of the output type may be made based on the entity data 630 and/or time data 650. For example, the commitment engine 60 may determine, based on user location data, that a user is not in a location at which the user would be able to view a display screen. The commitment engine 60 may therefore generate an output 670 that is conveyed to a speaker instead of the screen. In addition, some output types may have costs of notification 622 different from those of other output types. For example, a visual display may have a lower cost of notification 622 than a sound output, since a visual output may be less likely to interrupt a conversation.

In one example, the commitment engine 60 may receive context information 110 that satisfies the trigger condition 616 for a commitment 614 with the message "John has a meeting in 15 minutes." A cost function 620 then may be applied to the commitment 614. The cost function 620 may use entity data 630 to determine a cost of notification 622 and a cost of non-notification 624. The cost of notification 622 and the cost of non-notification 624 may be determined based at least in part on factors such as how important the message is to John, how receptive John is to receiving the message, and whether John is in a location that may be related to the message. For example, the entity data 630 may include entity identity data 112 and entity position data 114 that indicate that John is not currently in a location in which he could perceive an output 670 from the output device 672. As a result, the cost of non-notification 624 may be very small. In another example, based on entity data 630, the commitment engine 60 may determine that the cost of notification 622 is higher when John is making a telephone call than when John is reading a newspaper. In another example, where the message content includes medical information about John's newborn baby, the cost of non-notification 624 may be determined to be high.

In another example, the commitment engine 60 may receive context information 110 indicating that a baby is in a location near a user's swimming pool. This context information 110 may satisfy a trigger condition 616 for a commitment 614 corresponding to the situation in which a baby is near the user's pool. The commitment 614 may include a message/action 618 to broadcast an urgent message to a user that a baby is near the pool. A cost function 620 may be applied to a commitment 614. Based at least in part on the trigger condition 616 of the commitment 614 relating to a potentially serious safety situation involving a baby, the cost function 620 may determine that the commitment 614 has a very high cost of non-notification 624.

Continuing with this example, based on entity data 630 including user activity data, the commitment engine 60 may determine that the user is currently making a telephone call. The commitment engine 60 also may access profile data of the user indicating that the user strongly prefers to avoid interruptions when he is talking on the phone. As a result, the commitment engine 60 may determine that the cost of notification 622 is also high. In this example, given that the message relates to a safety situation involving a baby, the commitment engine 60 may determine that the cost of non-notification 624 is higher than the cost of notification 622. Accordingly, the commitment engine 60 conveys the urgent message 619 as an output 670 to be output by the output device 672 to the user.

In another example, commitment engine 60 may receive context information 110 that triggers the trigger condition 616 for a commitment 614 with the message "John has a meeting in 15 minutes." Using entity data 630, the commitment engine also may determine that John is currently making a telephone call. The commitment engine 60 may determine that since outputting a message notifying John of the commitment 614 on the output device 672 would interrupt John's telephone call, the cost of notification 622 is greater than the cost of non-notification 624. Thus, the commitment engine 60 may not convey the message to the output device 672 as output 670.

As the time of John's meeting approaches, the commitment engine 60 may increase the cost of non-notification 624 based on time data 650. For example, the commitment engine 60 may determine that John is five minutes away from the location of the meeting. When the time data 650 indicates that the meeting will begin in six minutes, the cost of non-notification 624 may be high enough that the commitment engine 60 conveys the message 619 to the output device 672 even though John is still making the telephone call.

Figure 14:
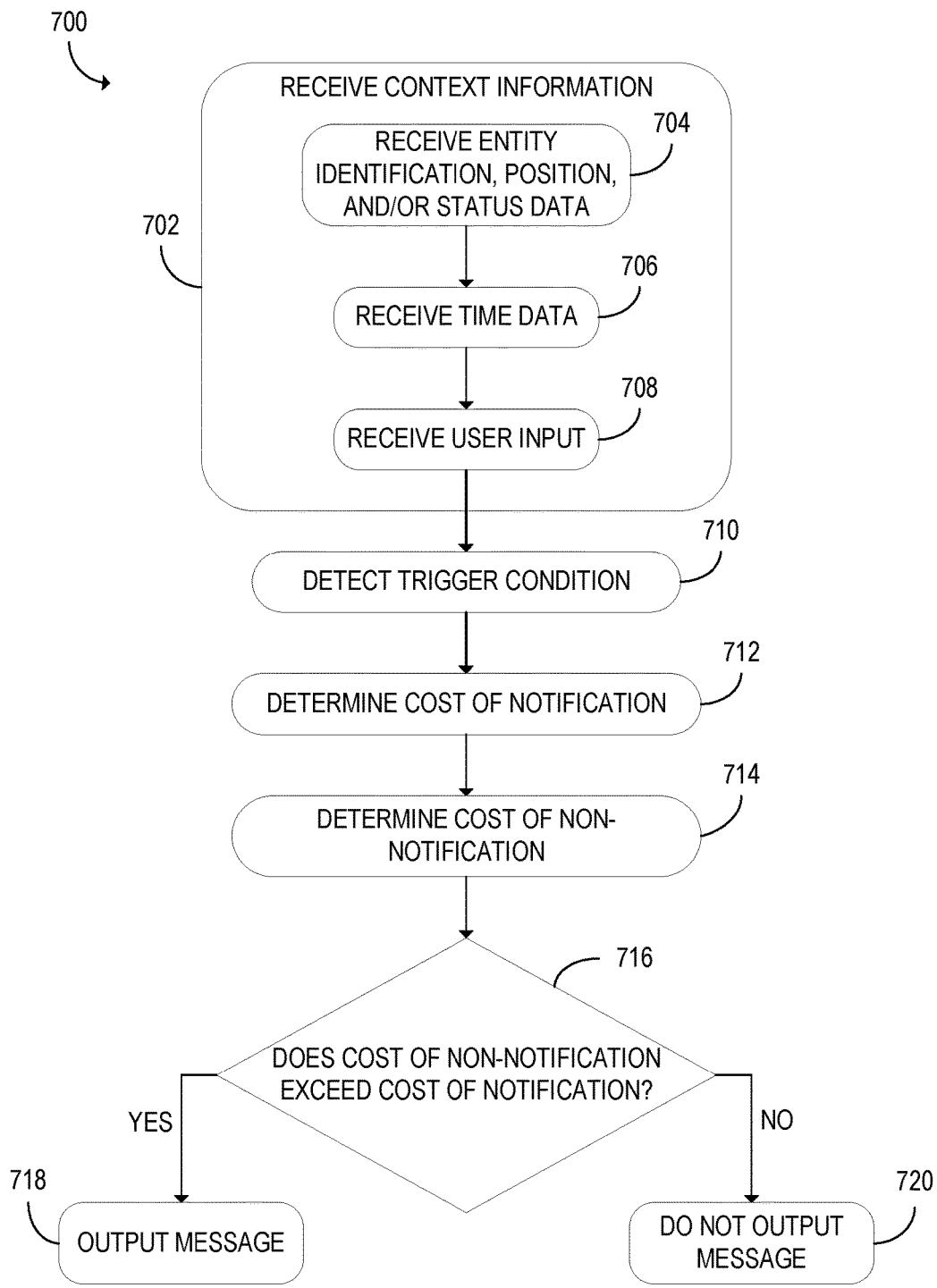
FIG. 14 shows a flowchart of a method for determining a cost of notification and a cost of non-notification according to examples of the present disclosure.

A flowchart of a method 700 for determining a cost of notification and a cost of non-notification of a message is shown in FIG. 14. The following description of method 700 is provided with reference to the software and hardware components described herein. It will be appreciated that method 700 also may be performed in other contexts using other suitable hardware and software components.

At 702 the method 700 may include receiving context information. Receiving the context information may include receiving entity data, time data, and/or a user input. At 704 the method 700 may include receiving entity data including entity identity, position, and/or status data. At 706 the method 700 may include receiving time data. The time data may include a time and/or date. The time data may further include at least one time interval. At 708 the method 700 may include receiving a user input.

At 710 the method 700 may include detecting that a trigger condition has occurred, based at least in part on the context information. The trigger condition may be associated with a commitment.

At 712 the method 700 may include determining a cost of notification that is associated with outputting the message on an output device. At 714 the method 700 may include determining a cost of non-notification that is associated with not outputting the message. In some examples, determining the cost of notification and the cost of non-notification may be based at least in part on the entity data, time data, and/or user input. In some examples, the cost of notification and cost of non-notification may be determined at least in part using a machine learning algorithm.

At 716 the method 700 may include comparing the cost of notification to the cost of non-notification. At 718 the method 700 may include, if the cost of non-notification exceeds the cost of notification, conveying the message to be output on the output device. At 720 the method 700 may include, if the cost of non-notification does not exceed the cost of notification, refraining from conveying the message to the output device.

It will be appreciated that method 700 is provided by way of example and is not meant to be limiting. Therefore, it is to be understood that method 700 may include additional and/or alternative steps relative to those illustrated in FIG. 14. Further, it is to be understood that method 700 may be performed in any suitable order. Further still, it is to be understood that one or more steps may be omitted from method 700 without departing from the scope of this disclosure.

In some examples, one or more cost functions may be used to determine and/or adjust a sampling rate of one or more sensors. In some use case scenarios, sampling and analyzing an environment with sensors may be a computationally intensive task. As explained above, a cost function may determine a cost of executing and/or not executing an action (such as communicating a message). Using such determinations, the system may increase or decrease the sample rate of one or more sensors that provide data related to the action. For example, where the action comprises notifying a user via outputting a message on an output device, a sensor rate may be increased or decreased based at least in part on the magnitude of the cost associated with refraining from outputting the message (e.g., non-notification).

In some examples, one or more cost functions may be used to customize a type and/or manner of delivery of a notification. In one example, a cost function may determine that a cost of non-notification of a message may be very high. For example, a user may establish a rule with the system that any messages containing the word "baby" are assigned a highest, critical importance status. Accordingly, where a message includes the word "baby", a cost function may determine that the cost of non-notification is very high, and correspondingly may broadcast the message at a high volume via all available speakers in a user's home.

Figure 15:
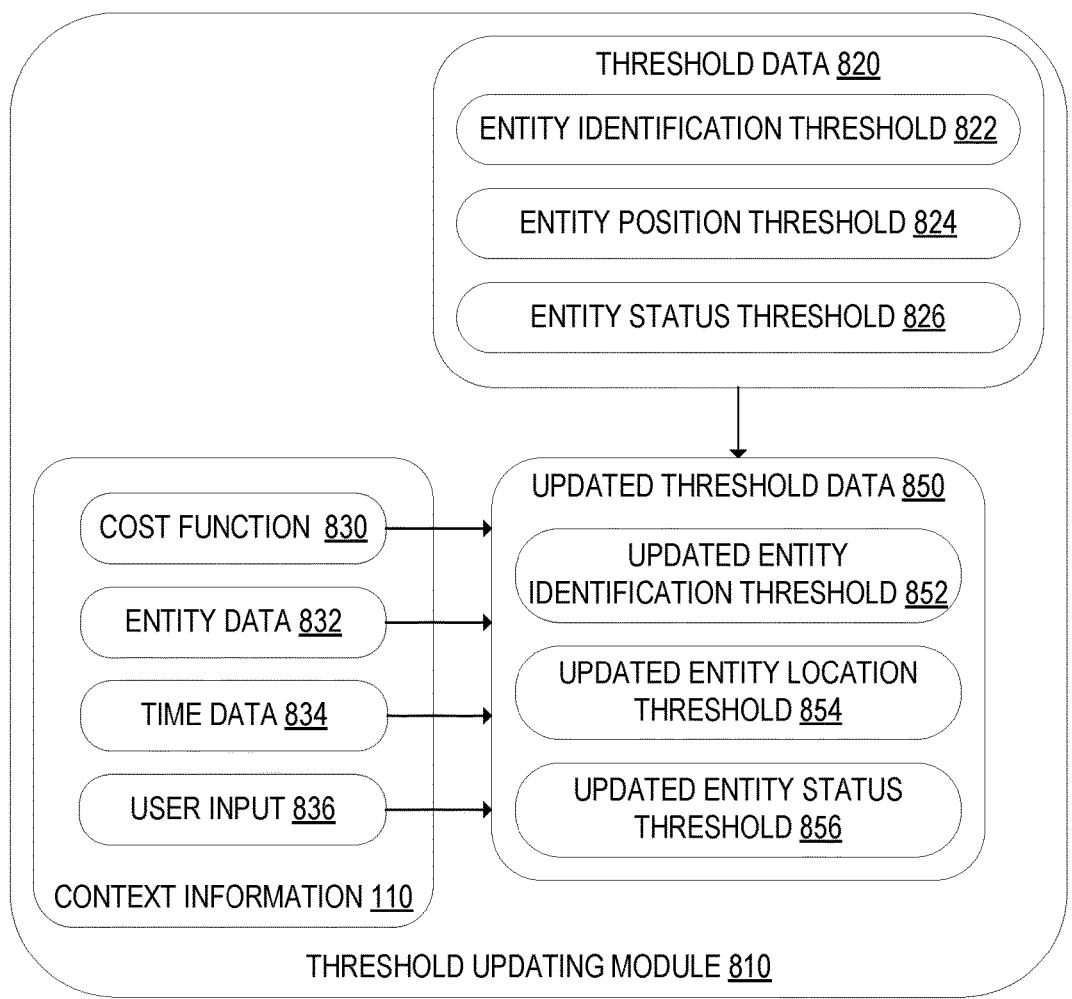
FIG. 15 shows a schematic representation of a threshold updating module according to examples of the present disclosure.

With reference now to FIG. 15, a schematic representation of a threshold updating module 810 according to examples of the present disclosure is provided. In different examples, threshold updating module 810 may be a standalone module in intelligent assistant system 20, or may be a component of the entity tracker 100, parser 40, or commitment engine 60. In some examples, the threshold updating module 810 may be configured to modify threshold data 820 that may be used to parse entity data 832. The threshold data 820 may include an entity identification threshold 822, an entity position/location threshold 824, and an entity status threshold 826. Each of these thresholds may be defined as a probability. When an entity identity, location, or status is determined to have a detection probability that exceeds the threshold probability for that entity identity, location, or status, a detection of that entity identity, location, or status may be indicated and/or recorded.

The threshold data 820 may be updated by the threshold updating module 810 to produce updated threshold data 850. The updated threshold data 850 may include an updated entity identification threshold 852, an updated entity location threshold 854, and an updated entity status threshold 856. The threshold updating module 810 may update the threshold data 820 based on a cost function 830, entity data 832, time data 834, and/or user input 836. In some examples, the cost function 830, entity data 832, and time data 834 may be the cost function 620, entity data 630, and time data 650 of FIG. 13.

In some examples, the threshold updating module 810 may update the threshold data 820 based on a modification of the cost function 830. As described above, the cost function 830 may be configured to determine a cost of notification and a cost of non-notification for messages that may be conveyed for output. In some examples, the modification to the cost function 830 may be made in response to a user input 836. For example, a sleep-deprived user may enter an input that increases the cost of notification when that user is determined to be sleeping. As a result, the threshold updating module 810 may decrease a user status threshold 826 for determining that the user is sleeping. In some examples, the user may enter an input 836 that directly updates the threshold data 820.

The threshold updating module 810 may also update the threshold data 820 based on entity data 832. As noted above, the entity data 832 may include entity identification data, entity location data, and/or entity status or activity data. In one example, threshold data 820 may include an entity identification threshold 822 and an entity location threshold 824 for detecting that both a child and an adult are simultaneously in proximity to a hot stove. The threshold updating module 810 may receive entity data 832 indicating that a child is alone in proximity to the hot stove. In response, the threshold updating module 810 may revise the corresponding entity identification threshold 822 and entity location threshold 824 to be lower.

In some examples, the threshold updating module 810 may also update the threshold data 820 based on time data 834. The time data may include a time, date, and/or at least one time interval that has elapsed since a particular input has been outputted, or since a particular input has been received. For example, the entity status threshold 826 for sleeping may be lowered when the time data 834 indicates that it is nighttime.

Figure 16:
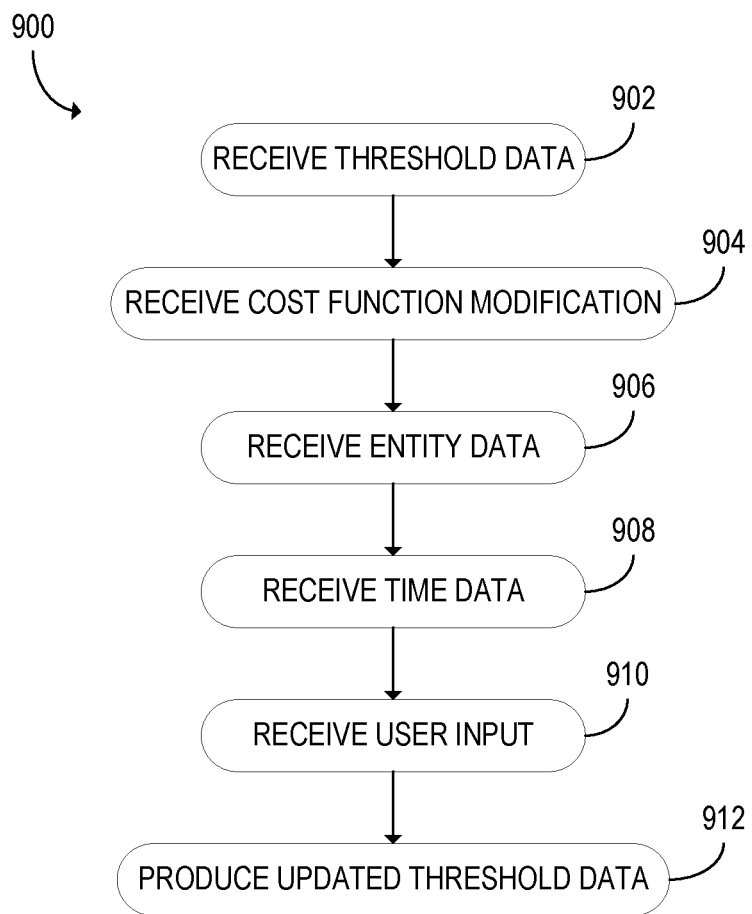
FIG. 16 shows a flowchart of a method for updating threshold data according to examples of the present disclosure.

A flowchart of a method 900 for updating threshold data is provided in FIG. 16. The following description of method 900 is provided with reference to the software and hardware components described herein. It will be appreciated that method 900 also may be performed in other contexts using other suitable hardware and software components.

At 902 the method 900 may include receiving a set of threshold data. The threshold data may include one or more probability thresholds above which a detection of a user, user location, or user activity may be registered. At 904 the method 900 may include receiving a modification to a cost function. At 906 the method 900 may include receiving entity data, which may include entity identification data, entity position/location data, and/or entity status data. At 908 the method 900 may include receiving time data, which may include a time, a date, and/or at least one time interval elapsed since a particular output was produced or a particular input was received. At 910 the method 900 may include receiving a user input. At 912 the method 900 may include producing updated threshold data by modifying the received threshold data based at least in part on the cost function modification, entity data, time data, and/or user input.

It will be appreciated that method 900 is provided by way of example and is not meant to be limiting. Therefore, it is to be understood that method 900 may include additional and/or alternative steps relative to those illustrated in FIG. 16. Further, it is to be understood that method 900 may be performed in any suitable order. Further still, it is to be understood that one or more steps may be omitted from method 900 without departing from the scope of this disclosure.

In some examples, intelligent assistant system 20 may train users to interact with the system in ways that minimize ambiguities. For example, the system may customize responses, queries, and other interactions with a particular user in a manner that trains the user to speak to the system using words or phrases that more clearly convey a user's intent. In this manner, follow-up queries from the system to clarify ambiguities may be minimized. In one example, where a user has two contacts named Fred (Jones and Smith), and the user frequently tells the system, "Call Fred", the system may offer the suggestion, "When you'd like to call one of your contacts Fred, it would be helpful to use his last name too."

In some examples, intelligent assistant system 20 may customize a user interface to provide additional opportunities for collecting user data that may be used to enhance user experiences. In some examples, such data may be utilized with machine learning techniques to learn user preferences and make predictions from such information. In one example, where a user utilizes a calendar application that provides reminders, the system may provide a user interface, or may modify an existing user interface, to gather useful data about the user. For example, when providing a reminder the calendar application may provide two default options of Dismiss and Snooze, with the Snooze period selectable in several 5 minute increments.

In some examples, intelligent assistant system 20 may modify the reminder user interface to display two different Snooze selectors with different labels—"Not now I'm busy" and "Not now, it's not important." Accordingly, when a user selects one of these more detailed selectors, the system may learn about the user; namely, what activities, persons, types of meetings, etc., the user considers "not important" or make the user "busy." In this manner, such information helps the system understand more about the user. As such data is gathered over time, machine learning techniques may be utilized to better understand user preferences and other attributes. In other examples, many other types of data (image, audio, physiological, etc.) may be gathered in conjunction with providing customized user interface experiences to learn more about a user.

With reference now to FIGS. 17-21, additional example implementations of intelligent assistant system 20 in a single computing device and across multiple computing devices are illustrated. Additional details regarding components and computing aspects of computing devices illustrated in FIGS. 17-21 are described below with reference to FIG. 23.

Figure 17:
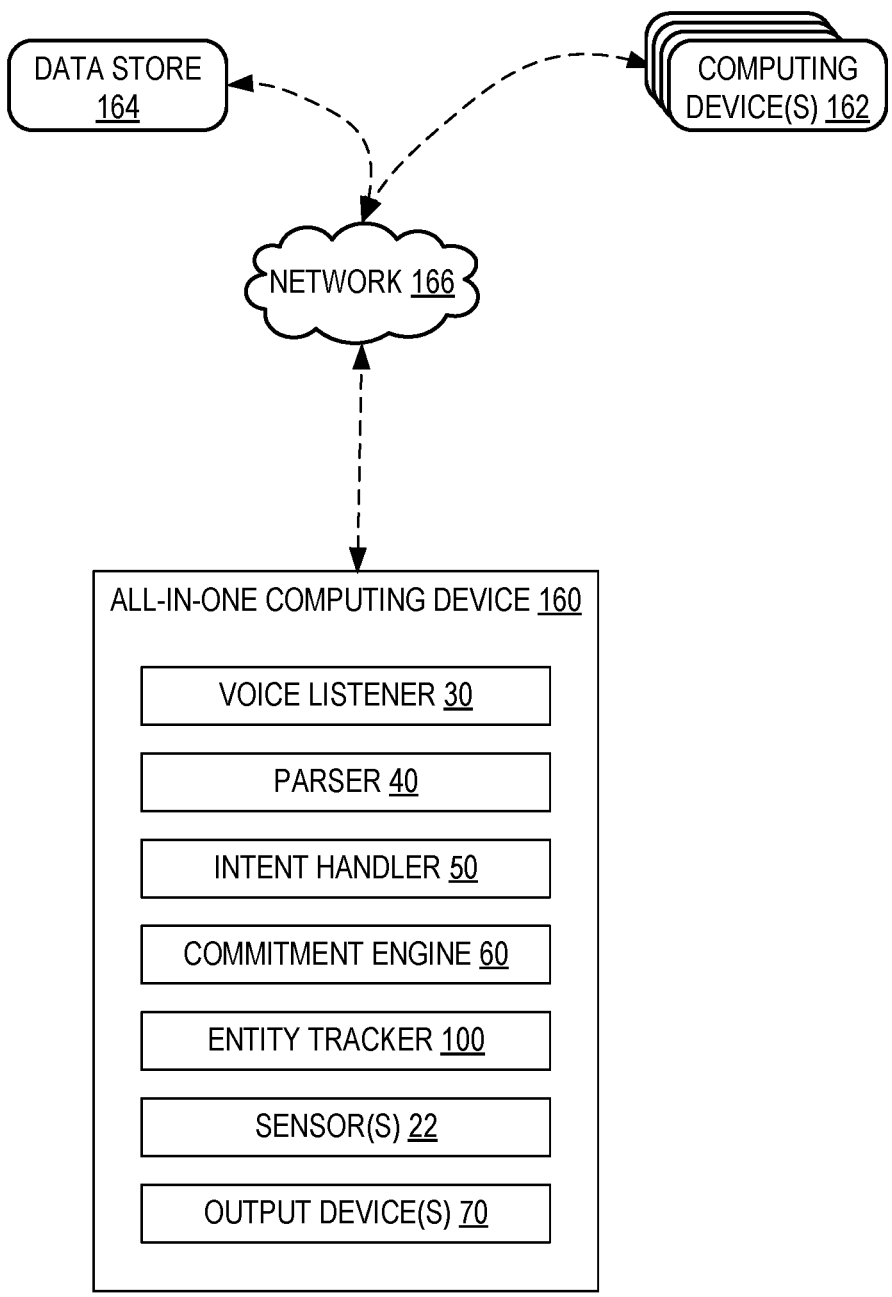
FIG. 17 schematically shows an all-in-one computing device that implements an intelligent assistant system according to examples of the present disclosure.

FIG. 17 shows an example of an all-in-one computing device 160 in which the components implementing intelligent assistant system 20 are arranged together in a standalone device. In some examples, all-in-one computing device 160 may be communicatively coupled to one or more other computing devices 162 via a network 166. In some examples, all-in-one computing device 160 may be communicatively coupled to a data store 164 that may store a variety of data, such as user profile data. All-in-one computing device 160 includes at least one sensor 22, voice listener 30, parser 40, intent handler 50, commitment engine 60, entity tracker 100, and at least one output device 70. Sensor(s) 22 include at least one microphone to receive natural language inputs from a user. In some examples one or more other types of sensor(s) 22 also may be included.

As described above, voice listener 30, parser 40, and intent handler 50 work in concert to convert natural language inputs into commitments that are executable by the all-in-one device 160. The commitment engine 60 stores such commitments in a commitment storage 626. The entity tracker 100 may provide context information to the commitment engine 60 and/or other modules. At a contextually appropriate time, the commitment engine 60 may execute a commitment and provide output, such as audio signals, to output device(s) 70.

Figure 18:
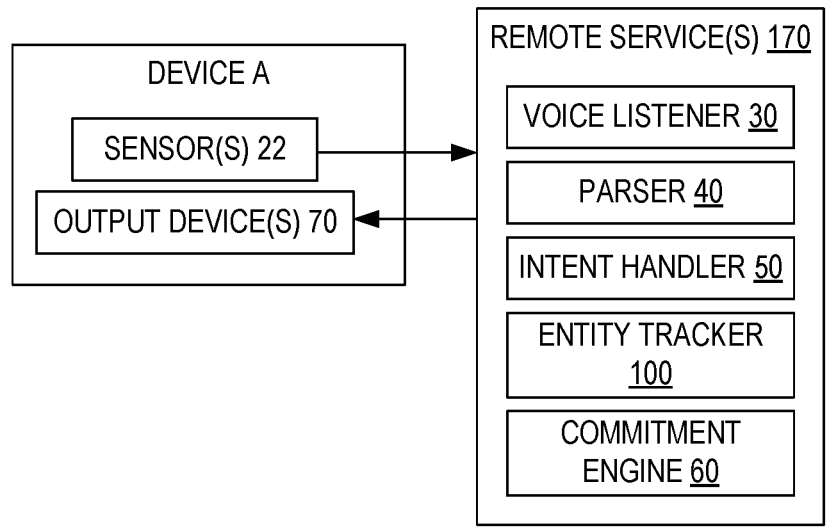
FIG. 18 schematically shows an example implementation in which one or more remote services perform functionality of the intelligent assistant system according to examples of the present disclosure.

FIG. 18 shows an example implementation in which one or more remote services 170 perform the natural language processing functionality of intelligent assistant system 20. In this example, voice listener 30, parser 40, intent handler 50, entity tracker 100 and commitment engine 60 reside on one or more computing devices, such as one or more servers, that are remotely located from a cloud-supported user device A. Sensor data from one or more sensors 22 of the user device A is provided to remote service(s) 170 via a network. For example, audio data of a user speaking may be captured by a microphone of user device A and provided to voice listener 30.

As described above, voice listener 30, parser 40, and intent handler 50 cooperate to convert the audio data into commitments that are stored in commitment engine 60. At a contextually appropriate time, the commitment engine 60 may execute a commitment and provide output, such as audio signals, to one or more output device(s) 70 of the user device A.

Figure 19:
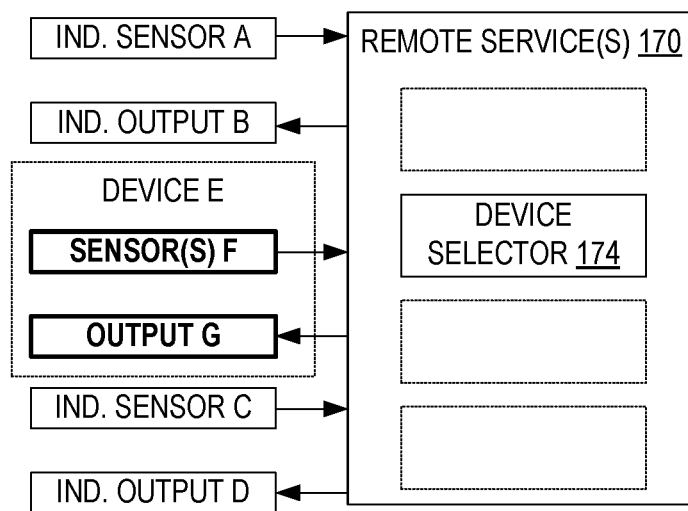
FIG. 19 schematically shows another example implementation in which one or more remote services perform functionality of intelligent assistant system according to examples of the present disclosure.

FIG. 19 shows another example implementation in which one or more remote services 170 perform the natural language processing functionality of intelligent assistant system 20. In this example, the one or more remote services 170 are communicatively coupled with a plurality of different sensors 22 and output devices 70. In this example, the sensors include individual standalone sensors A and C, such as microphones, cameras, etc. The output devices include individual standalone output devices B and D, such as loudspeakers.

The one or more remote services 170 are also communicatively coupled to a device E that includes one or more sensors F and an output device G. Device E may take the form of a simple standalone device comprising a microphone, speaker and network connectivity components. In other examples, device E may be a mobile phone, tablet computer, wall-mounted display, or other suitable computing device. In some examples, device E, sensors A and C, and output devices B and D may be part of the same cloud-supported client. In other examples, any number of individual sensors and devices may be utilized with the one or more remote services 170.

As described above, the one or more remote services 170 perform the natural language processing functionality of intelligent assistant system 20. In some examples, one or more of the remote services 170 may include all of the natural language processing modules of intelligent assistant system 20, as shown in the example of FIG. 18. In other examples, one or more remote services 170 may include less than all of the natural language processing modules, and may be communicatively coupled to the other modules located at one or more other service(s). In the present example, and as described in more detail below, one or more of the remote services 170 also may comprise a device selector 174 that may utilize sensor inputs to select output device B, D and/or G to receive output from the commitment engine 60.

Figure 20:
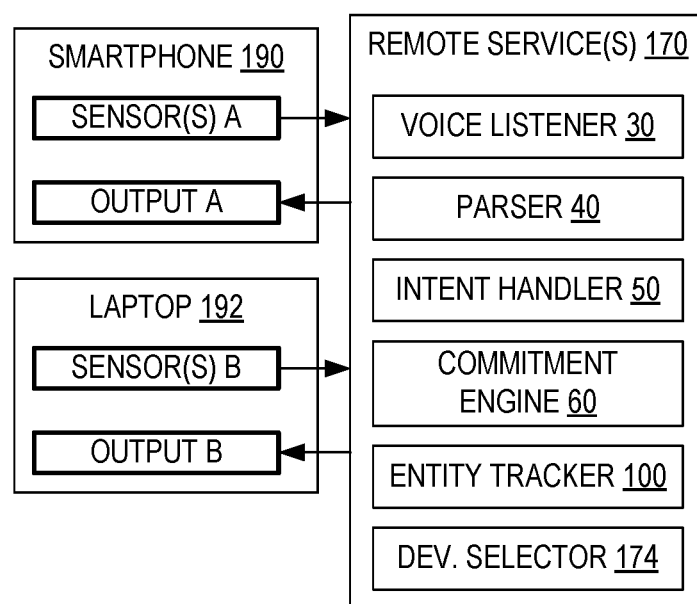
FIG. 20 schematically shows another example implementation in which one or more remote services utilizes a device selector according to examples of the present disclosure.

With reference now to FIG. 20, in some examples the intelligent assistant system 20 of the present disclosure may utilize device selector 174 to enable a user to communicate with another person whose location may be unknown to the user. In some examples, the system may use sensor data and/or corresponding context data to detect the presence and determine the location of the other person. Upon receiving a request from the user to speak to or locate the other person, the device selector 174 may select an appropriate output device for establishing communication between the user and the other person.

In the example use case of FIG. 20, one or more remote services 170 implementing intelligent assistant system 20 are communicatively coupled with a smartphone 190 and laptop 192. In one example, smartphone 190 comprises multiple sensors A including a microphone, and an output device A in the form of a speaker. The smartphone 190 may be located with a user in the user's basement media room of her home. The laptop computer 192 comprises multiple sensors B including a microphone and a webcam, and an output device B in the form of a speaker. The laptop 192 may be located in an upstairs bedroom of the home.

The user of the smartphone 190 may desire to communicate with her daughter, but may not know her current location within the home. The daughter may be in the upstairs bedroom with two other friends. The user may speak natural language inputs to indicate that she would like to communicate with her daughter. For example, the user may speak "Connect me to Sarah." The microphone in the user's smartphone 190 may receive the natural language input and send it to a remote service 170 for processing by the voice listener 30 and other components of intelligent assistant system 20 described above.

Upon determining the intent of the user, the commitment engine 60 may request context information 110 from the entity tracker 100 that includes the location of the user's daughter Sarah. In response, the entity tracker 100 may utilize video data from the webcam of the laptop 192 to identify Sarah in the field of view of the webcam. Entity tracker 100 may use other context information to determine that the laptop 192, and thus daughter Sarah, are located in the upstairs bedroom.

Using this information, the device selector 174 may communicatively couple the microphone and speaker of the user's smartphone 190 with microphone and speaker of laptop computer 192, and thereby allow the user to talk with her daughter.

In other examples and as discussed above, one or more other types of sensors and corresponding data may be used to locate a person or other entity. Examples include solely audio data, combinations of video and audio data, device log-in data, and other combinations of the foregoing and other sensor data.

Figure 21:
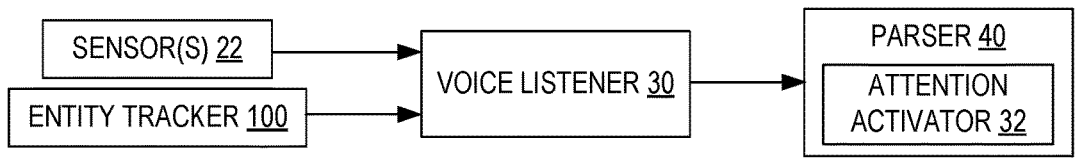
FIG. 21 schematically shows an example implementation in which one or more functions of the intelligent assistant system are activated upon detection of one or more spoken keywords.

In some examples, one or more functions of the intelligent assistant system 20 may be activated upon detection of one or more keywords that are spoken by a user. For example, the phrase "Hey Computer" may be used as a keyword phrase to activate one or more functions of the system. With reference now to FIG. 21, in one example one or more sensors 22 in the form of microphones may receive audio data of a user speaking "Hey computer, what time is the school board meeting tonight?" As described above, the voice listener 30 may process the audio data into text and confidence value(s), and pass this information to the parser 40. An attention activator 32 in parser 40 may identify the keyword phrase "Hey computer" in the text. In response, the parser 40 may activate or modify other components and functionality of the intelligent assistant system 20. For example, the parser 40 may increase a sampling rate of a speech recognition module to increase recognition accuracy of the user's speech that is likely to follow.

As noted above, upon processing audio data of a user's natural language input, a commitment engine may provide output to one or more output devices, such as a speaker and/or a video display. In some examples, a single device may include a microphone that captures a user's input, with such input provided to the intelligent assistant system 20, and a speaker that receives and broadcasts a message generated by the system in response to the input.

In some examples, a user may be in an environment with two or more microphones that may capture user speech and/or two or more speakers that may broadcast a message generated by the system in response to the speech. For example, a user may be in his media room with his mobile phone, laptop computer, tablet computer, and smart/connected television. Each of these devices may contain or be communicatively coupled with an intelligent assistant system 20.

A user may speak a keyword phrase that is captured by the microphones of each of the 4 devices. Accordingly, the corresponding message generated by the intelligent assistant system 20 may be broadcast by the speakers in all 4 devices, which may be annoying to the user. As described in more detail below, in some examples involving multiple sensors, output devices and/or other devices, the intelligent assistant system 20 may be configured to determine which of the multiple microphones to use for receiving user speech and/or which of the multiple speakers to use for broadcasting a corresponding message. In some examples and as described below, an aggregator may evaluate and weigh a plurality of metrics to determine which microphones and speakers to utilize.

Figure 22:
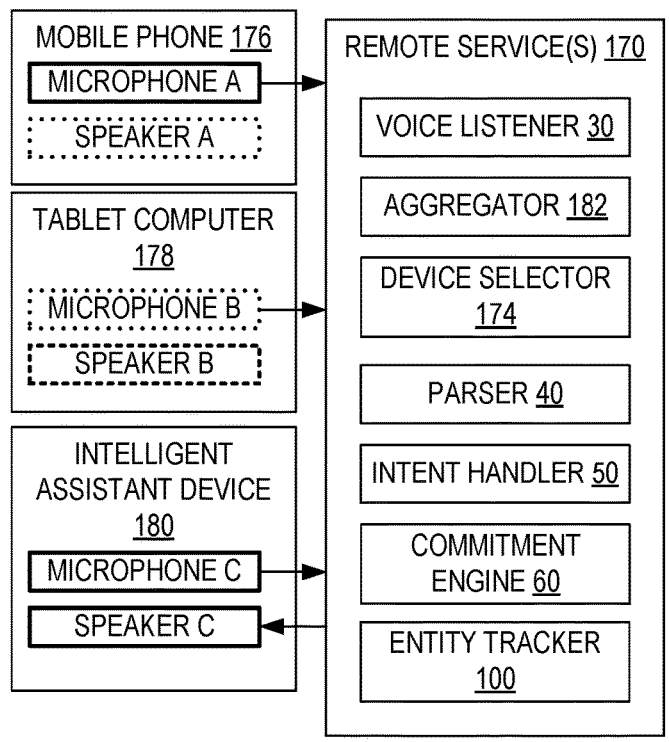
FIG. 22 schematically shows an example implementation of a multi-device environment in which sensor(s) and output device(s) are selected in response to voice activation according to examples of the present disclosure.

With reference now to FIG. 22, an example implementation of sensor and output device selection in response to voice activation in a multi-device environment is provided. In this example, one or more remote services 170 that implement the intelligent assistant system 20 may receive audio data from three different microphones A, B and C of three different devices, such as a mobile phone 176, tablet computer 178 and all-in-one intelligent assistant device 180.

A user in the vicinity of the three devices may speak a keyword phrase, such as "Hey Computer." Each of the microphones A, B and C may capture audio data of the user speaking this phrase and may send the audio data to voice listener 30. As described above, voice listener 30 may utilize speech recognition technologies to translate spoken utterances into text. Voice listener 30 also may assign confidence value(s) to the translated text. In some examples, the voice listener 30 may comprise a keyword detection algorithm configured to identify a keyword or keyword phrase in the translated text. The voice listener 30 may assign a confidence value to text that indicates a likelihood that the text is a keyword or keyword phrase.

In some examples, an aggregator 182 may evaluate a plurality of metrics related to a plurality of user audio data streams that are received from different individual microphones and/or from different microphone arrays. As described in more detail below, the aggregator 182 may utilize these metrics to select one of the audio data streams and its corresponding microphone(s) for use in interacting with the user. In some examples, the microphone(s) that is determined to be closest to the user may be selected. In some examples, the microphone(s) that is determined to provide the highest quality audio data may be selected. In some examples, the microphone(s) providing the highest quality audio data may be determined to be the closest microphone(s) to the user, and therefore may be selected.

When a microphone has been selected, the device selector 174 may select a speaker associated with this microphone to output a response to the user. For example, where the microphone is a component of a device that includes a speaker, this speaker may be selected. Where the microphone is a standalone microphone, the aggregator 182 may select another speaker in the vicinity of the user to output the response. In the example of FIG. 22, the aggregator 182 is located on one of the remote services 170 that implements at least a portion of the intelligent assistant system 20. In other examples, the aggregator 182 may be located on another computing device, such as in another cloud-based service.

In one use case example, the aggregator 182 may utilize 4 metrics to evaluate a user audio data stream that is received: (1) an amplitude (volume) of the received audio signal; (2) a signal-to-noise (S/N) ratio of the audio signal; (3) a keyword confidence value indicating a likelihood that the data stream contains a keyword or keyword phrase; and (4) a user identification confidence value indicating a likelihood that the speaker is a particular person.

In some examples, the amplitude and/or S/N values may be received with the audio data stream. In other examples, amplitude and/or S/N values may be determined by the voice listener 30 or other components of the intelligent assistant system 20. As described above, the keyword confidence value may be determined by the voice listener 30. Also as described above, the user identification confidence value may be determined by entity tracker 100. In some examples, the user speaking the input may be identified by voice recognition as a known speaker or an unknown speaker, and assigned a corresponding level of confidence.

The S/N ratio may be calculated for the received audio input by comparing a signal level of a user's voice to a level of background noise. In some examples the amplitude of the input may be used to determine a proximity of the user to the corresponding microphone. It will be appreciated that the metrics discussed in the present implementations are provided as examples and are not meant to be limiting.

Each of the received audio data streams also may include a device ID that identifies the particular device or standalone sensor that is providing the data stream. In some examples, after receiving a first set of metrics from a first device or sensor, the aggregator 182 may pause for a predetermined period of time to determine if one or more other devices/sensors also received the keyword or keyword phrase from the same person as the user identified in the first set of metrics. For example, the aggregator 182 may pause for 0.5 seconds, 1.0 seconds, or any other period of time that does not create a negative user experience for the user.

In the present example and as shown in FIG. 22, the aggregator 182 evaluates metrics for audio data streams received from the mobile phone 176, tablet computer 178 and all-in-one intelligent assistant device 180. For each device, the aggregator 182 may combine the 4 metrics into a single selectability score, such as by averaging the 4 metrics. In some examples and prior to combining, each of the metrics may be weighted by empirically-determined weights that reflect the accuracy of a metric in predicting the device/microphone and corresponding audio data stream that will provide the best user experience. By comparing the selectability scores of each of the devices/microphones and their data streams, the aggregator 182 may identify and select the desired device/data stream.

In one example, for each of the 4 metrics, the aggregator 178 may compare the scores of each device/microphone and correspondingly rank the devices/microphone per metric. For example, the aggregator 178 may determine the following scores for the audio data stream received from microphone A of the mobile phone 176: 1) 90% (Amplitude); 2) 90% (S/N); 3) 30% (Keyword confidence); 4) 90% (Speaker ID). Scores for the audio data stream received from microphone B of the tablet computer 178 may be: 1) 80% (Amplitude); 2) 80% (S/N); 3) 80% (Keyword confidence); 4) 80% (Speaker ID). Scores for the audio data stream received from the microphone C of the intelligent assistant device 180 may be: 1) 92% (Amplitude); 2) 88% (S/N); 3) 90% (Keyword confidence); 4) 92% (Speaker ID).

In this example, the rankings of the 3 devices for each of the 4 metrics would be as follows:
 A. Amplitude—1. Intelligent assistant device; 2. Mobile phone; 3. Tablet computer.
 B. S/N Ratio—1. Mobile phone; 2. Intelligent assistant device; 3. Tablet computer.
 C. Keyword Confidence—1. Intelligent assistant device; 2. Tablet computer; 3. Mobile phone.
 D. Speaker ID—1. Intelligent assistant device; 2. Mobile phone; 3. Tablet computer.

Each device may be awarded points based on its ranking in each metric category. For example, a first place ranking=1 point, second place=2 points and third place=3 points. For each device, its points are totaled for the 4 metrics and averaged. The aggregator 182 selects the device (and corresponding data stream) with the lowest average point total. In the present example, the final point totals and rankings are: 1. Intelligent assistant device=>1.25; 2. Mobile phone=>2.0; 3. Tablet computer=>2.75. Thus, the aggregator 178 selects the data stream from the intelligent assistant device 180$n$ for continued analysis by the intelligent assistant system 20. Additionally, and based on the above ranking, the device selector 174 may select the intelligent assistant device 180 to receive the message(s) generated by commitment engine 60 as a result of the analysis.

In some examples, upon selection by the aggregator 182 of the intelligent assistant device 180 as described above, the aggregator also may cause the other two devices to refrain from sending audio data streams that are associated with the same speaker ID (i.e., person) that is associated with the analyzed data stream. In this manner, where the same user provides more natural language input after the initial input, only the selected intelligent assistant device 180 will provide the corresponding audio data to the remote service(s) 170. In some examples, the other two devices may resume sending audio data streams when the same person speaks the keyword or keyword phrase. In these cases, the above-described selection process may be performed again to determine the selected device.

In some examples and as noted above, prior to averaging the awarded points, each point award may be multiplied by an empirically-determined weighted value that reflects the accuracy of a metric in predicting the device and corresponding audio data stream that will provide the best user experience. In some examples, one or more machine learning techniques may be utilized to build models for computing the different metrics.

In some example implementations, the signal amplitude may strongly correlate to a user's distance from the microphone receiving the user's speech. The S/N ratio also may provide a good indicator of the user's distance from the microphone, as a lower noise value may correlate to the user being closer to the microphone. Where the signal amplitude and S/N ratio of the signal are both relatively high, the speaker ID accuracy may correspondingly benefit from the strong signal.

It will be appreciated that the methods and use cases described above are merely examples, and many variations are possible. For example, a subset of the above 4 metrics may be utilized to evaluate a user audio data stream. In other examples, one or more additional metrics also may be utilized.

In some examples, a user who has previously established a conversation with the intelligent assistant system 20 via a selected device among multiple devices may have a brief pause before initiating a next conversation with the same device. The system may compare the duration of the pause to a predetermined time period, and may consider the comparison in selecting a device for the next conversation. For example, where the duration of the pause is less than the predetermined period, such as 5 seconds, the system may include the recently-established speaker ID and the existence of the previous conversation in the device determination analysis as a bias towards selecting the same device for the next conversation.

The examples described above include recognition of an audible keyword to activate one or more functions of the intelligent assistant system. In some examples, functions of the system may be activated by recognition of one or more other signals. Such signals may include, for example, a user gesture captured by a camera, a user eye-gaze, and a face direction of the user.

In some examples, one or more of the above-described techniques for device selection may be utilized to automatically update the selected device based on one or more factors. For example, where a user is communicating with the intelligent assistant system 20 via a first device, as the user changes her location and moves farther away from the first device, the system may correspondingly change the selected device to a second device closer to the user's new location.

In some implementations, imaging data in addition to audio data from one or more image sensors may be utilized to select a device. For example, context data 110 received from entity tracker 100 may include imaging data that may be used to select a device. Examples of imaging data may include video from an RGB camera, infrared images from an IR camera, depth images from a depth camera, thermal images from a thermal camera, etc. For example, an RGB camera may track a user's location within a room. Images from the camera may be used to select the appropriate device/microphone(s) to receive the user's natural language input, and/or to select the appropriate speaker(s) to broadcast a message to the user. In some examples and with reference to the device selection techniques described above, imaging data and related parameters may be included as a metric that is analyzed by the aggregator 182 to determine device selection.

In some examples, captured images of a user may be used to identify which device a user is facing when speaking. In some examples, indicators such as face detection may be used to identify a user. In some examples, captured video may indicate lip movement of a user that may be used to associate a spoken keyword with the user. In an environment with multiple users, such indicators also may identify the particular user who is addressing a device. As such, both voice and physical recognition may be used as parameters to distinguish a user from among the plurality of users.

Other examples of inputs that may be used in selecting a device/microphone and/or speaker include radar signals and lidar signals. In some examples, signals from connected devices may indicate that a user is interacting with the device. In one example, a user may activate a mobile phone via fingerprint recognition. Such an interaction may be a strong indicator that the user is present at the location of the phone.

In some embodiments, the methods and processes described herein may be tied to a computing system of one or more computing devices. In particular, such methods and processes may be implemented as a computer-application program or service, an application-programming interface (API), a library, and/or other computer-program product.

Figure 23:
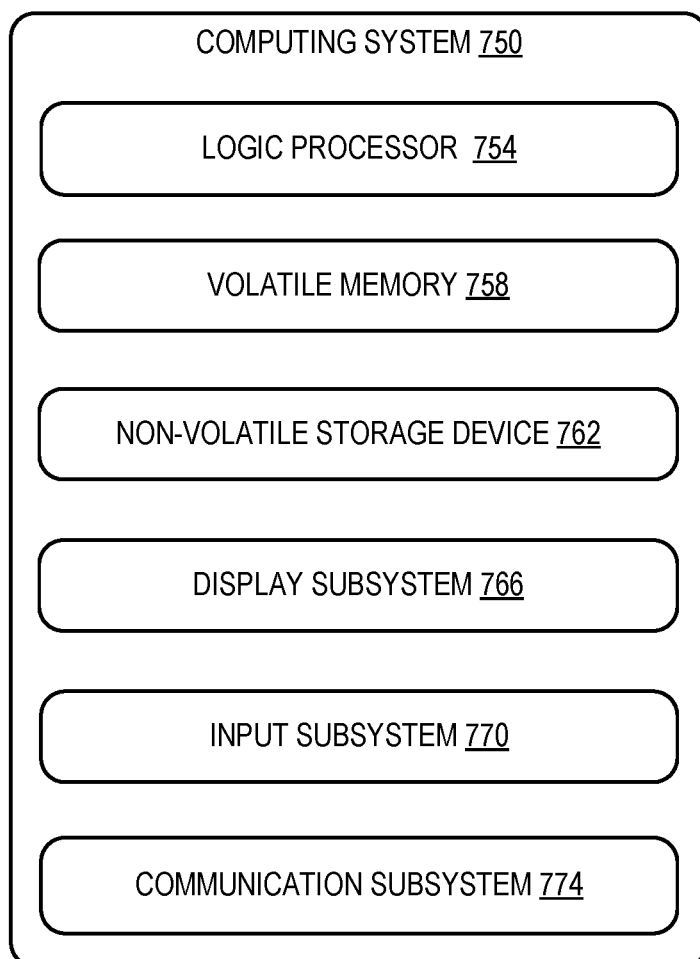
FIG. 23 schematically shows a computing system according to examples of the present disclosure.

FIG. 23 schematically shows a non-limiting embodiment of a computing system 750 that can enact one or more of the methods and processes described above. Computing system 750 is shown in simplified form. Computing system 750 may take the form of one or more personal computers, server computers, tablet computers, home-entertainment computers, network computing devices, gaming devices, mobile computing devices, mobile communication devices (e.g., smartphone), and/or other computing devices.

Computing system 750 includes a logic processor 754, volatile memory 758, and a non-volatile storage device 762. Computing system 600 may optionally include a display subsystem 766, input subsystem 770, communication subsystem 774, and/or other components not shown in FIG. 23.

Logic processor 754 includes one or more physical devices configured to execute instructions. For example, the logic processor may be configured to execute instructions that are part of one or more applications, programs, routines, libraries, objects, components, data structures, or other logical constructs. Such instructions may be implemented to perform a task, implement a data type, transform the state of one or more components, achieve a technical effect, or otherwise arrive at a desired result.

The logic processor 754 may include one or more physical processors (hardware) configured to execute software instructions. Additionally or alternatively, the logic processor may include one or more hardware logic circuits or firmware devices configured to execute hardware-implemented logic or firmware instructions. Processors of the logic processor 754 may be single-core or multi-core, and the instructions executed thereon may be configured for sequential, parallel, and/or distributed processing. Individual components of the logic processor optionally may be distributed among two or more separate devices, which may be remotely located and/or configured for coordinated processing. Aspects of the logic processor 754 may be virtualized and executed by remotely accessible, networked computing devices configured in a cloud-computing configuration. In such a case, these virtualized aspects may be run on different physical logic processors of various different machines.

Volatile memory 758 may include physical devices that include random access memory. Volatile memory 758 is typically utilized by logic processor 754 to temporarily store information during processing of software instructions. It will be appreciated that volatile memory 758 typically does not continue to store instructions when power is cut to the volatile memory.

Non-volatile storage device 762 includes one or more physical devices configured to hold instructions executable by the logic processors to implement the methods and processes described herein. When such methods and processes are implemented, the state of non-volatile storage device 762 may be transformed—e.g., to hold different data.

Non-volatile storage device 762 may include physical devices that are removable and/or built-in. Non-volatile storage device 762 may include optical memory (CD, DVD, HD-DVD, Blu-Ray Disc, etc.), semiconductor memory (ROM, EPROM, EEPROM, FLASH memory, etc.), and/or magnetic memory (hard-disk drive, floppy-disk drive, tape drive, MRAM, etc.), or other mass storage device technology. Non-volatile storage device 762 may include nonvolatile, dynamic, static, read/write, read-only, sequential-access, location-addressable, file-addressable, and/or content-addressable devices. It will be appreciated that non-volatile storage device 762 is configured to hold instructions even when power is cut to the non-volatile storage device.

Aspects of logic processor 754, volatile memory 758, and non-volatile storage device 762 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

The terms "module", "program" and "engine" may be used to describe an aspect of computing system 750 implemented to perform a particular function. In some cases, a module, program or engine may be instantiated via logic processor 754 executing instructions held by non-volatile storage device 762, using portions of volatile memory 758. It will be understood that different modules, programs or engines may be instantiated from the same application, service, code block, object, library, routine, API, function, etc. Likewise, the same module, program or engine may be instantiated by different applications, services, code blocks, objects, routines, APIs, functions, etc. The terms modules, programs and engines encompass individual or groups of executable files, data files, libraries, drivers, scripts, database records, etc.

It will be appreciated that a "service", as used herein, is an application program that may be executable across multiple user sessions. A service may be available to one or more system components, programs, and/or other services. In some implementations, a service may run on one or more server-computing devices.

When included, display subsystem 766 may be used to present a visual representation of data held by non-volatile storage device 762. As the herein described methods and processes change the data held by the non-volatile storage device, and thus transform the state of the non-volatile storage device, the state of display subsystem 766 may likewise be transformed to visually represent changes in the underlying data. Display subsystem 766 may include one or more display devices utilizing virtually any type of technology. Such display devices may be combined with logic processor 754, volatile memory 758, and/or non-volatile storage device 762 in a shared enclosure, or such display devices may be peripheral display devices.

When included, input subsystem 770 may comprise or interface with one or more user-input devices. In some embodiments, the input subsystem may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, color, stereoscopic, and/or depth camera for machine vision and/or gesture recognition; a head tracker, eye tracker, accelerometer, and/or gyroscope for motion detection, gaze detection, and/or intent recognition; electric-field sensing componentry for assessing brain activity; any of the sensors described with respect to the example use cases and environments discussed above; and/or any other suitable sensor.

When included, communication subsystem 774 may be configured to communicatively couple computing system 750 with one or more other computing devices. Communication subsystem 774 may include wired and/or wireless communication devices compatible with one or more different communication protocols. As non-limiting examples, the communication subsystem may be configured for communication via a wireless telephone network, or a wired or wireless local- or wide-area network. In some embodiments, the communication subsystem may allow computing system 750 to send and receive data to and from other devices via a network such as the Internet.

The following paragraphs provide additional support for the claims of the subject application. One aspect provides a computing device, comprising: a logic processor; and a storage device holding instructions executable by the logic processor to: receive image data of an environment including a person; process the image data using a face detection algorithm to produce a first face detection output at a first frequency; determine an identity of the person based on the first face detection output; process the image data using another algorithm that uses less computational resources of the computing device than the face detection algorithm, the other algorithm producing a tracking output at a second frequency greater than the first frequency; track the person within the environment based on the tracking output; and perform one or more of updating the other algorithm using a second face detection output, and updating the face detection algorithm using the tracking output. The computing device may additionally or optionally include, wherein the instructions are executable to process the image data using the other algorithm while not processing the image data using the face detection algorithm. The computing device may additionally or optionally include, wherein the instructions are executable to select the other algorithm based on a battery life condition associated with the computing device. The computing device may additionally or optionally include, wherein the instructions are executable to select the other algorithm based on an allocation of resources of the logic processor to one or more tasks other than processing of the image data. The computing device may additionally or optionally include, wherein the other algorithm is a color tracking algorithm, and wherein the tracking output includes a color histogram. The computing device may additionally or optionally include, wherein the other algorithm is a motion tracking algorithm, and wherein the tracking output includes one or more motion vectors. The computing device may additionally or optionally include, wherein the other algorithm is a first tracking algorithm, and wherein the instructions are executable to process the image data using a second tracking algorithm that uses less computational resources of the computing device than the face detection algorithm, wherein the tracking output of the first tracking algorithm is provided as input to the second tracking algorithm. The computing device may additionally or optionally include, wherein the instructions executable to update the face detection algorithm using the tracking output are executable to update a target region of the image data in which to prioritize the processing of the image data using the face detection algorithm, the target region corresponding to a location of the person tracked by the tracking output. The computing device may additionally or optionally include, wherein the instructions executable to update the other algorithm using the second face detection output are executable to update an association between a region of the image data in which a face of the person is detected and the tracking output. The computing device may additionally or optionally include one or more image sensors integrated in the computing device and being configured to collect the image data, and wherein the computing device is an all-in-one computing device located in the environment. The computing device may additionally or optionally include, wherein the image data is received from one or more image sensors remotely located from the computing device.

Another aspect provides, at a computing device, a method of entity tracking, comprising: receiving image data of an environment including a person; processing the image data using a face detection algorithm to produce a first face detection output at a first frequency; determining an identity of the person based on the first face detection output; processing the image data using another algorithm that uses less computational resources of the computing device than the face detection algorithm, the other algorithm producing a tracking output at a second frequency greater than the first frequency; tracking the person within the environment based on the tracking output; and performing one or more of updating the other algorithm using a second face detection output, and updating the face detection algorithm using the tracking output. The method may additionally or optionally include, wherein the other algorithm is a body shape tracking algorithm, and wherein the tracking output includes a body model. The method may additionally or optionally include, wherein the other algorithm is a gait tracking algorithm, and wherein the tracking output includes gait analysis data. The method may additionally or optionally include, wherein updating the face detection algorithm using the tracking output includes updating a target region of the image data in which to prioritize the processing of the image data using the face detection algorithm, the target region corresponding to a location of the person tracked by the tracking output. The method may additionally or optionally include, wherein updating the other algorithm using the second face detection output includes updating an association between a region of the image data in which a face of the person is detected and the tracking output. The method may additionally or optionally include, wherein the other algorithm is selected from among two or more tracking algorithms configured to produce respective tracking outputs each having a corresponding datatype. The method may additionally or optionally include, wherein the other algorithm is a first tracking algorithm, the method further comprising processing the image data using a second tracking algorithm that uses less computational resources of the computing device than the face detection algorithm, wherein the tracking output of the first tracking algorithm is provided as input to the second tracking algorithm.

Another aspect provides an all-in-one computing device, comprising: one or more image sensors; a logic processor; and a storage device holding instructions executable by the logic processor to: receive image data of an environment including a person from the one or more image sensors; process the image data using a face detection algorithm to produce a first face detection output at a first frequency; determine an identity of the person based on the first face detection output; process the image data using another algorithm that uses less computational resources of the computing device than the face detection algorithm, the other algorithm producing a tracking output at a second frequency greater than the first frequency; track the person within the environment based on the tracking output; and perform one or more of updating the other algorithm using a second face detection output, and updating the face detection algorithm using the tracking output. The all-in-one computing device may additionally or optionally include, wherein the other algorithm is a first tracking algorithm, and wherein the instructions are executable to process the image data using a second tracking algorithm that uses less computational resources of the computing device than the face detection algorithm, wherein the tracking output of the first tracking algorithm is provided as input to the second tracking algorithm.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and non-obvious combinations and sub-combinations of the various processes, systems and configurations, and other features, functions, acts, and/or properties disclosed herein, as well as any and all equivalents thereof.

The invention claimed is:

1. A computing device, comprising:
a logic processor; and
a storage device holding instructions executable by the logic processor to:
receive image data of an environment including a person;
process the image data using a face detection algorithm to produce a first face detection output at a first frequency;
determine an identity of the person based on the first face detection output;
process the image data using another algorithm that uses less computational resources of the computing device than the face detection algorithm, the other algorithm producing a tracking output at a second frequency greater than the first frequency;
track the person within the environment based on the tracking output; and
perform one or more of updating the other algorithm using a second face detection output, and updating the face detection algorithm using the tracking output.

2. The computing device of claim 1, wherein the instructions are executable to process the image data using the other algorithm while not processing the image data using the face detection algorithm.

3. The computing device of claim 1, wherein the instructions are executable to select the other algorithm based on a battery life condition associated with the computing device.

4. The computing device of claim 1, wherein the instructions are executable to select the other algorithm based on an allocation of resources of the logic processor to one or more tasks other than processing of the image data.

5. The computing device of claim 1, wherein the other algorithm is a color tracking algorithm, and wherein the tracking output includes a color histogram.

6. The computing device of claim 1, wherein the other algorithm is a motion tracking algorithm, and wherein the tracking output includes one or more motion vectors.

7. The computing device of claim 1, wherein the other algorithm is a first tracking algorithm, and wherein the instructions are executable to process the image data using a second tracking algorithm that uses less computational resources of the computing device than the face detection algorithm, wherein the tracking output of the first tracking algorithm is provided as input to the second tracking algorithm.

8. The computing device of claim 1, wherein the instructions executable to update the face detection algorithm using the tracking output are executable to update a target region of the image data in which to prioritize the processing of the image data using the face detection algorithm, the target region corresponding to a location of the person tracked by the tracking output.

9. The computing device of claim 1, wherein the instructions executable to update the other algorithm using the second face detection output are executable to update an association between a region of the image data in which a face of the person is detected and the tracking output.

10. The computing device of claim 1, further comprising one or more image sensors integrated in the computing device and being configured to collect the image data, and wherein the computing device is an all-in-one computing device located in the environment.

11. The computing device of claim 1, wherein the image data is received from one or more image sensors remotely located from the computing device.

12. A method of entity tracking at a computing device, comprising:
receiving image data of an environment including a person;
processing the image data using a face detection algorithm to produce a first face detection output at a first frequency;
determining an identity of the person based on the first face detection output;
processing the image data using another algorithm that uses less computational resources of the computing device than the face detection algorithm, the other algorithm producing a tracking output at a second frequency greater than the first frequency;
tracking the person within the environment based on the tracking output; and
performing one or more of updating the other algorithm using a second face detection output, and updating the face detection algorithm using the tracking output.

13. The method of claim 12, wherein the other algorithm is a body shape tracking algorithm, and wherein the tracking output includes a body model.

14. The method of claim 12, wherein the other algorithm is a gait tracking algorithm, and wherein the tracking output includes gait analysis data.

15. The method of claim 12, wherein updating the face detection algorithm using the tracking output includes updating a target region of the image data in which to prioritize the processing of the image data using the face detection algorithm, the target region corresponding to a location of the person tracked by the tracking output.

16. The method of claim 12, wherein updating the other algorithm using the second face detection output includes updating an association between a region of the image data in which a face of the person is detected and the tracking output.

17. The method of claim 12, wherein the other algorithm is selected from among two or more tracking algorithms configured to produce respective tracking outputs each having a corresponding datatype.

18. The method of claim 12, wherein the other algorithm is a first tracking algorithm, the method further comprising processing the image data using a second tracking algorithm that uses less computational resources of the computing device than the face detection algorithm, wherein the tracking output of the first tracking algorithm is provided as input to the second tracking algorithm.

19. An all-in-one computing device, comprising:
one or more image sensors;
a logic processor; and
a storage device holding instructions executable by the logic processor to:
receive image data of an environment including a person from the one or more image sensors;
process the image data using a face detection algorithm to produce a first face detection output at a first frequency;
determine an identity of the person based on the first face detection output;
process the image data using another algorithm that uses less computational resources of the computing device than the face detection algorithm, the other algorithm producing a tracking output at a second frequency greater than the first frequency;
track the person within the environment based on the tracking output; and
perform one or more of updating the other algorithm using a second face detection output, and updating the face detection algorithm using the tracking output.

20. The computing device of claim 19, wherein the other algorithm is a first tracking algorithm, and wherein the instructions are executable to process the image data using a second tracking algorithm that uses less computational resources of the computing device than the face detection algorithm, wherein the tracking output of the first tracking algorithm is provided as input to the second tracking algorithm.

* * * * *